United States Patent
Stary et al.

(10) Patent No.: US 10,485,861 B2
(45) Date of Patent: Nov. 26, 2019

(54) NANOPARTICLE-BASED COMPOSITIONS

(71) Applicants: President and Fellows of Harvard College, Cambridge, MA (US); Massachusetts Institute of Technology, Cambridge, MA (US); The Brigham and Women's Hospital, Inc., Boston, MA (US)

(72) Inventors: Georg Stary, Brookline, MA (US); Aleksandar Filip Radovic-Moreno, State College, PA (US); Pamela A. Basto, Cambridge, MA (US); Michael N. Starnbach, Needham, MA (US); Robert S. Langer, Newton, MA (US); Omid C. Farokhzad, Waban, MA (US); Ulrich Von Andrian, Chestnut Hill, MA (US)

(73) Assignees: President and Fellows of Harvard College, Cambridge, MA (US); Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 14/772,695

(22) PCT Filed: Mar. 14, 2014

(86) PCT No.: PCT/US2014/029000
§ 371 (c)(1),
(2) Date: Sep. 3, 2015

(87) PCT Pub. No.: WO2014/153087
PCT Pub. Date: Sep. 25, 2014

(65) Prior Publication Data
US 2016/0008451 A1    Jan. 14, 2016

Related U.S. Application Data

(60) Provisional application No. 61/783,439, filed on Mar. 14, 2013.

(51) Int. Cl.
*A61K 39/118* (2006.01)
*A61K 45/06* (2006.01)
(Continued)

(52) U.S. Cl.
CPC ........ *A61K 39/118* (2013.01); *A61K 31/4745* (2013.01); *A61K 31/711* (2013.01);
(Continued)

(58) Field of Classification Search
CPC .......... A61K 9/10; A61K 35/74; A61K 39/39; A61K 39/522; A61K 39/55555;
(Continued)

(56) References Cited

U.S. PATENT DOCUMENTS 3,960,757 A    6/1976 Morishita et al.
4,638,045 A    11/1987 Kohn et al.
(Continued)

FOREIGN PATENT DOCUMENTS

WO    WO1997028259    8/1997
WO    WO1998016247    4/1998
(Continued)

OTHER PUBLICATIONS

Alexsandar et al., (ACS Nano, 2012, 6 (5), pp. 4279-4287).*
(Continued)

*Primary Examiner* — Jana A Hines
(74) *Attorney, Agent, or Firm* — McCarter & English, LLP; Maria Laccotripe Zacharakis

(57) ABSTRACT

Provided herein are new compositions including an inactivated pathogen and one or more adjuvant-loaded polymeric
(Continued)

nanoparticles, wherein the adjuvant-loaded nanoparticles are bound to the inactivated pathogen. These compositions are useful for preventing and/or treating diseases caused by the specific pathogens, especially when administered to a subject's mucosal membranes.

7 Claims, 18 Drawing Sheets

(51) Int. Cl.
| | |
|---|---|
| A61K 31/4745 | (2006.01) |
| A61K 31/711 | (2006.01) |
| A61K 39/02 | (2006.01) |
| A61K 39/04 | (2006.01) |
| A61K 39/085 | (2006.01) |
| A61K 39/09 | (2006.01) |
| A61K 39/00 | (2006.01) |

(52) U.S. Cl.
CPC .......... *A61K 39/0208* (2013.01); *A61K 39/04* (2013.01); *A61K 39/085* (2013.01); *A61K 39/092* (2013.01); *A61K 45/06* (2013.01); *A61K 2039/521* (2013.01); *A61K 2039/5252* (2013.01); *A61K 2039/543* (2013.01); *A61K 2039/55555* (2013.01); *A61K 2039/55572* (2013.01); *C12N 2740/16034* (2013.01); *C12N 2760/16134* (2013.01); *C12N 2760/18534* (2013.01); *C12N 2770/16034* (2013.01); *C12N 2770/20034* (2013.01); *Y02A 50/386* (2018.01); *Y02A 50/388* (2018.01); *Y02A 50/403* (2018.01); *Y02A 50/466* (2018.01); *Y02A 50/478* (2018.01); *Y02A 50/48* (2018.01); *Y02A 50/484* (2018.01)

(58) Field of Classification Search
CPC .......... A61K 39/55566; A61K 39/5254; A61K 39/543; A61K 39/118; A61K 39/541; A61K 9/48; A61K 38/20; A61K 38/21; A61P 31/00
See application file for complete search history.

(56) References Cited

U.S. PATENT DOCUMENTS

| | | | |
|---|---|---|---|
| 4,806,621 A | 2/1989 | Kohn et al. | |
| 4,946,929 A | 8/1990 | D'Amore et al. | |
| 5,010,167 A | 4/1991 | Ron et al. | |
| 5,019,379 A | 5/1991 | Domb et al. | |
| 5,399,665 A | 3/1995 | Barrera et al. | |
| 5,512,600 A | 4/1996 | Mikos et al. | |
| 5,514,378 A | 5/1996 | Mikos et al. | |
| 5,543,158 A | 8/1996 | Gref et al. | |
| 5,696,175 A | 12/1997 | Mikos et al. | |
| 5,716,404 A | 2/1998 | Vacanti et al. | |
| 5,736,372 A | 4/1998 | Vacanti et al. | |
| 5,770,417 A | 6/1998 | Vacanti et al. | |
| 5,804,178 A | 9/1998 | Vacanti et al. | |
| 5,837,752 A | 11/1998 | Shastri et al. | |
| 5,902,599 A | 5/1999 | Anseth et al. | |
| 5,922,326 A | 7/1999 | Murphy et al. | |
| 6,095,148 A | 8/2000 | Shastri et al. | |
| 6,123,727 A | 9/2000 | Vacanti et al. | |
| 6,130,082 A | 10/2000 | Majarian et al. | |
| 6,207,646 B1 | 3/2001 | Krieg et al. | |
| 6,506,577 B1 | 1/2003 | Deming et al. | |
| 6,585,980 B1 | 7/2003 | Chan et al. | |
| 6,632,671 B2 | 10/2003 | Unger | |
| 6,632,922 B1 | 10/2003 | Deming et al. | |
| 6,686,446 B2 | 2/2004 | Deming et al. | |
| 6,696,076 B2 | 2/2004 | Tomai et al. | |
| 6,818,732 B2 | 11/2004 | Deming et al. | |
| 7,192,725 B2 | 3/2007 | Chan et al. | |
| 7,223,398 B1 | 5/2007 | Tuck et al. | |
| 7,250,403 B2 | 7/2007 | Van Nest et al. | |
| 7,566,703 B2 | 7/2009 | Krieg et al. | |
| 2003/0104011 A1 | 6/2003 | Rios | |
| 2006/0241076 A1 | 10/2006 | Uhlmann et al. | |
| 2010/0104503 A1 | 4/2010 | Mellman et al. | |
| 2010/0112078 A1 | 5/2010 | Panda et al. | |
| 2010/0129439 A1* | 5/2010 | Alexis .................... A61K 39/00 424/451 |
| 2010/0233251 A1 | 9/2010 | Von Andrian et al. | |
| 2011/0268805 A1 | 11/2011 | Alexis et al. | |
| 2012/0093884 A1 | 4/2012 | Vesikari et al. | |
| 2012/0213812 A1 | 8/2012 | Lipford et al. | |

FOREIGN PATENT DOCUMENTS

| | | |
|---|---|---|
| WO | WO1998055495 | 12/1998 |
| WO | WO1999011275 | 3/1999 |
| WO | WO2000006123 | 2/2000 |
| WO | WO2000061151 | 10/2000 |
| WO | WO2003086280 | 10/2003 |
| WO | WO2005097993 | 10/2005 |
| WO | WO 2006/136448 | 12/2006 |
| WO | WO2007062107 | 5/2007 |
| WO | WO2008033432 | 3/2008 |
| WO | WO2009051837 | 4/2009 |
| WO | WO 2010/120385 | 10/2010 |
| WO | WO2012068295 | 5/2012 |
| WO | WO 2014153087 | 9/2014 |

OTHER PUBLICATIONS

Aleksandar et al., "Bacteria-Targeting Nanoparticles for Managing Infections," retrieved from https://dspace.mit.edu/hanlde/1721.1/79250#fiels-area, retrieved on Aug. 5, 2016, Feb. 2013, 216 pages.
Arbeitsgemeinschaft Dermatologische Forschung: "Annual Meeting of Arbeitsgemeinschaft Dermatologische Forschung in collaboration with Deutsche Dermatologische Gesellschaft," Mar. 2013, 53 pages.
Stacy et al., "A mucosal vaccine against Chlamydia trachomatis generates two waves of protective memory T cells," Science, 348(6241):aaa8205-aaa8205 (Jun. 2015).
Supplementary European Search Report, in European Application No. 14770692, dated Aug. 8, 2016, 5 pages.
Taha et al., "Biodegradable PLGA85/15 nanoparticles as a delivery vehicle for Chlamydia trachomatis recombinant MOMP-187 peptide," Nanotechnology*, 23(32):325101 (May 2012).

Aguado and Lambert, "Controlled-release vaccines—biodegradable polylactide/polyglycolide (PL/PG) microspheres as antigen vehicles" Immunobiology, 184(2-3): 113-25, 1992.

Akagi et al., "Biodegreadable Nanoparticles as Vaccine Adjuvants and Delivery Systems: Regulation of Immune Responses by Nanoparticle-Based Vaccine," Adv Polym Sci. 247:31-64, 2012.

Astete et al., "Synthesis and characterization of PLGA nanoparticles" J. Biomater. Sci. Polymer Edn, vol. 17, No. 3, pp. 247-289 (2006).

Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004).

Ballas et al., "Induction of Nk activity in murine and human cells by CpG motifs in oligodeoxynucleotides and bacterial DNA." J. Immunol. 157:1840-45 (1996).

Barrera et al., "Synthesis and RGD peptide modification of a new biodegradable copolymer: poly(lactic acid-co-lysine)," J. Am. Chem. Soc., 115:11010 (1993).

Beck et al., "A new long-acting injectable microcapsule system for the administration of progesterone," Fertil. Steril. 31:545, 1979.

Benita, et al., "Characterization of drug-loaded poly(d,l-lactide) microspheres," J. Phann. Sci., 73:1721, 1984.

Bonifaz, et al., "Efficient targeting of protein antigen to the dendritic cell receptor DEC-205 in the steady state leads to antigen presentation on major histocompatibility complex class I products and peripheral CD8+ T cell tolerance," J. Exp. Med., 196(12):1627-38, 2002.

(56) References Cited

OTHER PUBLICATIONS

Bonifaz, et al., "In vivo targeting of antigens to maturing dendritic cells via the DEC-205 receptor improves T cell vaccination," J. Exp. Med., 199(6):815-24, 2004.
Boussif et al., "A versatile vector for gene and oligonucleotide transfer into cells in culture and in vivo: polyethylenimine," Proc. Natl. Acad. Sci., USA, 1995, 92:7297 (1995).
Bramwell, et al., "Particulate delivery systems for biodefense subunit vaccines," Adv. Drug Deliv. Rev., 57(9):1247-65, 2005.
Chu et al. CpG oligodeoxynucleotides act as adjuvants that switch on T helper 1 (Th1) immunity J. Exp. Med. 186:1623-1631, 1997.
Cowdery et al. "Bacterial DNA induces NK cells to produce IFN-gamma in vivo and increases the toxicity of lipopolysaccharides," J. Immunol. 156:4570-75 (1996).
Davis et al. "CpG DNA is a potent enhancer of specific immunity in mice immunized with recombinant hepatitis B surface antigen," J. Immunol. 160:870-876 (1998).
Deming et al., "Facile synthesis of block copolypeptides of defined architecture," Nature, 390:386 (1997).
Gref et al., "Biodegradable long-circulating polymeric nanospheres," Science 263: 1600-1603, 1994.
Haensler et al., "Polyamidoamine cascade polymers mediate efficient transfection of cells in culture," Bioconjugate Chem., 4:372 (1993).
Hawiger, et al., "Dendritic cells induce peripheral T cell unresponsiveness under steady state conditions in vivo," J. Exp. Med., 194(6):769-79, 2001.
Heil et al., "Species-Specific Recognition of Single-Stranded RNA via Toll-like Receptor 7 and 8" Science 303(5663), 1526-1529 (2004).
Jiang, et al., "Biodegradable poly(lactic-co-glycolic acid) microparticles for injectable delivery of vaccine antigens," Adv. Drug Deliv. Rev., 57(3):391-410, 2005.
Kabanov et al., "DNA complexes with polycations for the delivery of genetic material into cells," Bioconjugate Chem., 6:7-20 (1995).
Klinman et al. "Contribution of CpG motifs to the immunogenicity of Dna vaccines," J. Immunol. 158:3635-39 (1997).
Knox, et al., "Immunological properties of teichoic acids," Bacteriol. Rev. 37(2):215-57, 1973.
Krieg et al., "CpG motifs in bacterial DNA trigger direct B cell activation," Nature. 374:546-549, 1995.
Krieg et al., "Antiinfective applications of toll-like receptor 9 agonists," Proc Am Thorac Soc. 4(3):289-94, 2007.
Kukowska-Latallo et al., "Efficient transfer of genetic material into mammalian cells using Starburst polyamidoamine dendrimers," Proc. Natl. Acad. Sci., USA, 93:4897-902 (1996).
Kwon et al., "Pseudopoly(amino acids): a study of the synthesis and characterization of poly(trans-4-hydroxy-N-acyl-L-proline esters)," Macromolecules, 22:3250-3255, 1989.
Langer, "Selected advances in drug delivery and tissue engineering," J. Control. Release, 62:7-11, 1999.
Langer, "Biomaterials in drug delivery and tissue engineering: one laboratory's experience," Acc. Chem. Res., 33:94-101, 2000.
Lim et al., "A Self-Destroying Polycationic Polymer: biodegradable Poly(4-hydroxy-L-proline ester)", J. Am. Chem. Soc., 121:5633-5639, 1999.
Lim et al., "Cationic hyperbranched poly(amino ester): a novel class of DNA condensing molecule with cationic surface, biodegradable three-dimensional structure, and tertiary amine groups in the interior," J. Am. Chem. Soc., 123:2460-1, 2001.
Lipford et al. CpG-containing synthetic oligonucleotides promote B and cytotoxic T cell 30 responses to protein antigen: a new class of vaccine adjuvants. Eur. J. Immunol. 1997. 27:2340-2344.
Lipford et al., "Bacterial DNA as immune cell activator," Trends Microbial. 1998. 6:496-500.
Malyala, et al., "Enhancing the therapeutic efficacy of CpG oligonucleotides using biodegradable microparticles" Advanced Drug Delivery Reviews 61: 218-225 (2009).

Martimprey et al., "Polymer nanocarriers for the delivery of small fragments of nucleic acids: Oligonucleotides and siRNA" European Journal of Pharmaceutics and Biopharmaceutics 71:490-504 (2009).
Mathiowitz, et al., "Morphology of polyanhydride microsphere delivery systems," J. Scanning Microscopy 4:329-40, 1990.
McCluskie et al., "Mucosal immunization with DNA vaccines," Microbes Infect. 1(9):685-98 1999.
Meldal, et al, "Cu-catalyzed azide-alkyne cycloaddition," Chem. Rev. 108(8), 2952-3015, 2008.
Mellman and Steinman, "Dendritic cells: specialized and regulated antigen processing machines," Cell 106(3):255-8, 2001.
Mellman, "Antigen processing and presentation by dendritic cells: cell biological mechanisms," Adv. Exp. Med. Biol. 560:63-7, 2005.
Mestecky, "The common mucosal immune system and current strategies for induction of immune responses in external secretions," Journal of Clinical Immunology, 7:265-276, 1987.
Ogra et al., "Vaccination strategies for mucosal immune responses," Clin Microbiol Rev. 14(2):430-45, 2001.
Papisov, 2001, ACS Symposium Series, 786:301.
Pisetsky, "The immunologic properties of DNA ," J. Immunol. 156:421-423, 1996.
Putnam et al., "Poly(4-hydroxy-l-proline ester): Low-Temperature Polycondensation and Plasmid DNA Complexation," Macromolecules, 32:3658-3662, 1999.
Reis et al., "Nanoencapsulation I. Methods for preparation of drug-loaded polymeric nanoparticles" Nanomedicine 2:8-21 (2006).
Roman et al. "Immunostimulatory DNA sequences function as T helper-I-promoting adjuvants," Nat. Med. 3:849-854, 1997.
Rosenthal et al., "Challenges for vaccination against sexually-transmitted diseases: induction and long-term maintenance of mucosal immune responses in the female genital tract," Semin Immunol. 9(5):303-14, 1997.
Sato et al. "Immunostimulatory DNA sequences necessary for effective intradermal gene immunization," Science 273:352-354, 1996.
Schmidt et al., "Clinical setbacks for toll-like receptor 9 agonists in cancer," Nat. Biotechnol. 25(8):825-6, 2007.
Shabarova et al, "DNA-like duplexes with repetitions: efficient template-guided polycondensation of decadeoxyribonucleotide imidazolide," FEBS Letters, 154 288, (1983).
Sharpless et al., "A stepwise huisgen cycloaddition process: copper(I)-catalyzed regioselective "ligation" of azides and terminal alkynes," Angew. Chem. Int. Ed. 41(14), 2596, (2002).
Shimada et al., "In vivo augmentation of natural killer cell activity with a deoxyribonucleic acid fraction of BCG," Jpn. J. Cancer Res. 77:808-816, 1986.
Summerton, Ann. N.Y. Acad. Sci., 1058:1-14, 2005.
Tang et al., "In vitro gene delivery by degraded polyamidoamine dendrimers," Bioconjugate Chem., 7:703-14, 1996.
Tse, et al., "Evaluation of different buffers on plasmid DNA encapsulation into PLGA microparticles," International Journal of Pharmaceutics, 370 (1-2), 33-40 (2009).
Uhrich et al., "Polymeric systems for controlled drug release," Chem. Rev., 99:3181-98,1999.
Wang et al., "A novel biodegradable gene carrier based on polyphosphoester," J. Am. Chem. Soc., 123:9480-1, 2001.
Yamamoto et al., "Unique palindromic sequences in synthetic oligonucleotides are required to induce IFN [correction of INF] and augment IFN-mediated [correction of INF] natural killer activity," J. Immunol. 148:4072-76, 1992.
Zauner et al., "Polylysine-based transfection systems utilizing receptor-mediated delivery", Adv. Drug Del. Rev., 30:97-113, 1998.
Zhou et al., "Preparation of poly(L-serine ester): a structural analog of conventional poly(L-serine)," Macromolecules, 23:3399-3406, 1990.
Akin, D. et al. Bacteria-mediated delivery of nanoparticles and cargo into cells. Nature Nanotechnology 2:441-449 (2007).
Brunham, R C & Rey-Ladino, J. Immunology of Chlamydia infection: Implications for a Chlamydia trachomatis vaccine. Nature Reviews Immunology 5:149-161 (2005).
Chen, F., Zhou, J., Luo, F. L., Mohammed, A. B. & Zhang, X. L. Aptamer from whole-bacterium SELEX as new therapeutic reagent

(56) References Cited

OTHER PUBLICATIONS against virulent *Mycobacterium tuberculosis*. Biochemical and Biophysical Research Communications 357:743-748 (2007).

Chung, Y. C., Wang, H. L., Chen, Y. M. & Li, S. L. Effect of Abiotic Factors on the Antibacterial Activity of Chitosan Against Waterborne Pathogens. Bioresour Technol 88:179-184 (2003).

Dillen, K. et al. Adhesion of PLGA or Eudragit/PLGA Nanoparticles to *Staphylococcus* and Pseudomonas. Int J Pharm 349:234-240 (2008).

Gu, H. W., Ho, P. L., Tong, E., Wang, L. & Xu, B. Presenting vancomycin on nanoparticles to enhance antimicrobial activities. Nano Letters 3:1261-1263 (2003).

Igietseme, J. U., Black, C. M. & Caldwell, H. D. Chlamydia vaccines—Strategies and status. Biodrugs 16:19-35 (2002).

Igietseme, J. U., Eko, F. O. & Black, C. M. Chlamydia vaccines: recent developments and the role of adjuvants in future formulations. Expert Review of Vaccines 10:1585-1596 (2011).

International Preliminary Report on Patentability and Written Opinion; PCT/US2014/29000; dated Sep. 24, 2015; 11 pp.

International Search Report; PCT/US2014/29000; dated Jul. 21, 2014; 2 pp.

Kamaly, N., Xiao, Z., Valencia, P. M., Radovic-Moreno, A. F. & Farokhzad, O. C. Targeted polymeric therapeutic nanoparticles: design, development and clinical translation. Chem Soc Rev 41, 2971-3010, doi:10.1039/c2cs15344k (2012).

Kell, A. J. et al. Vancomycin-modified nanoparticles for efficient targeting and preconcentration of Gram-positive and Gram-negative bacteria. ACS Nano 2, 1777-1788 (2008).

Kolishetti, N. et al. Engineering of self-assembled nanoparticle platform for precisely controlled combination drug therapy. Proceedings of the National Academy of Sciences of the United States of America 107, 17939-17944, doi:10.1073/pnas.1011368107 (2010).

Leptihn, S. et al. Single molecule resolution of the antimicrobial action of quantum dot-labeled sushi peptide on live bacteria. BMC Biol 7, 22, doi:10.1186/1741-7007-7-22 (2009).

Liu, L. H. et al. Self-assembled cationic peptide nanoparticles as an efficient antimicrobial agent. Nature Nanotechnology 4, 457-463, doi:Doi 10.1038/Nnano.2009.153 (2009).

Nederberg, F. et al. Biodegradable nanostructures with selective lysis of microbial membranes. Nat Chem 3, 409-414 (2011).

Radovic-Moreno et al.; "Surface Charge-Switching Polymeric nanoparticles for Bacterial Cell Wall-Targeted Deliver of Antibiotics"; ACS Nano vol. 6, No. 5; pp. 4279-4287; 2012; 9 pp.

Umamaheshwari, R. B. & Jain, N. K. Receptor mediated targeting of lectin conjugated gliadin nanoparticles in the treatment of Helicobacter pylori. J Drug Target 11, 415-423; discussion 423-414, doi:10.1080/1061186031000164771 (2003).

Zasloff, M. Antimicrobial peptides of multicellular organisms Nature 415, 389-395, doi:10.1038/415389a (2002).

Zhao, X. J. et al. A rapid bioassay for single bacterial cell quantitation using bioconjugated nanoparticles. Proc Natl Acad Sci U S A 101, 15027-15032, doi:Doi 10.1073/Pnas.040486101 (2004).

Arbeitsgemeinschaft Dermatologische Forschung, "40th Annual Meeting of the Arbeitsgemeinschaft Dermatologische Forschung in collaboration with the Deutsche Dermatologische Gesellschaft (DDG)," Feb. 26, 2013. Retrieved from the Internet: <URL: http://www.adf-online.de/wp-content/uploads/2013-ADF-Programm-Inhalt.pdf>, [retrieved on Aug. 8, 2016], 53 pages.

Radovic-Moreno, "Bacteria-targeting nanoparticles for managing infections," Nov. 9, 2012. Doctoral dissertation, Massachusetts Institute of Technology. Retrieved from the Internet: <URL: https://dspace.mit.edu/handle/1721.1/79250#files-area>, [retrieved on Aug. 5, 2016], 215 pages.

Stary et al., "A mucosal vaccine against Chlamydia trachomatis generates two waves of protective memory T cells," Science, 348(6241):aaa8205, 15 pages, Jun. 19, 2015.

Taha et al., "Biodegradable PLGA85/15 nanoparticles as a delivery vehicle for Chlamydia trachomatis recombinant MOMP-187 peptide," Nanotechnology, 23(32):325101, Epub Jul. 23, 2012.

European Search Report in Application No. 14770692.3, dated Aug. 18, 2016, 4 pages.

Moon et al., "Antigen-Displaying Lipid-Envelped PLGA Nanoparticles as Delivery Agents for a Plasmodium vivax Malaria Vaccine," PLOS ONE, 7(2):e31472-1 (Feb. 2012).

Office Action in European Application No. 14770692.3, dated Jul. 31, 2017, 8 pages.

Bergsson et al. "In vitro inactivation of Chlamydia trachomatis by fatty acids and monoglycerides." Antimicrobial agents and chemotherapy, 1998, 42.9: 2290-2294.

Brunham, "A Chlamydia vaccine on the horizon," Science, Jun. 19, 2015, 348(6241):1322-1323, DOI: 10.1126/science.aac6528.

Lu et al., "GM-CSF transgene-based adjuvant allows the establishment of protective mucosal immunity following vaccination with inactivated Chlamydia trachomatis." The Journal of Immunology, 2002, 169.11: 6324-6331.

Medical University of Vienna, "New and innovative approach for successful vaccination against Chlamydia infections," ScienceDaily, Jun. 25, 2018, [retrieved on Oct. 15, 2018], retrieved from: URL<www.sciencedaily.com/releases/2015/06/150625081304.htm>.

Office Action in Israeli Application No. 241534, dated Aug. 7, 2018, 8 pages (with English translation).

Rey-Ladino et al., "A live and inactivated Chlamydia trachomatis mouse pneumonitis strain induces the maturation of dendritic cells that are phenotypically and immunologically distinct." Infection and immunity, 2005, 73.3: 1568-1577.

Summons to Attend Oral Proceedings in European Application No. 14770692.3, dated Jul. 25, 2018, 8 pages.

\* cited by examiner

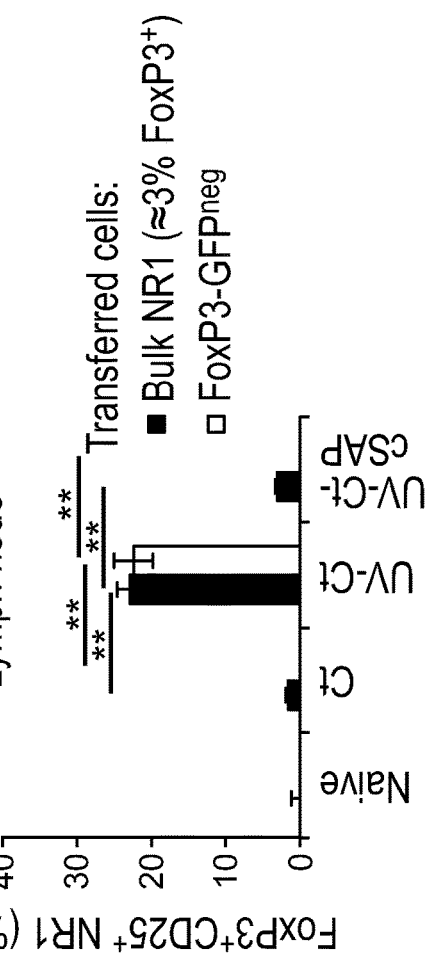
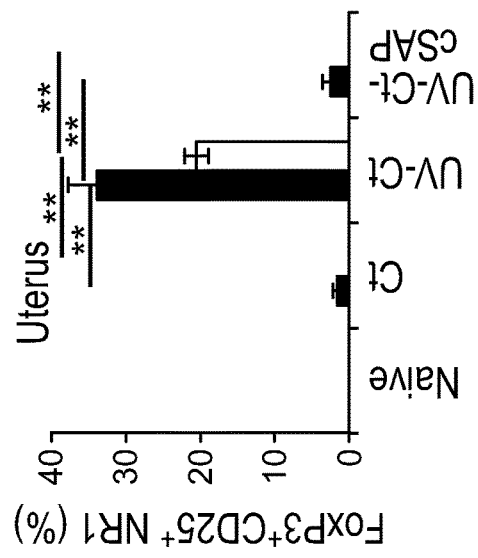
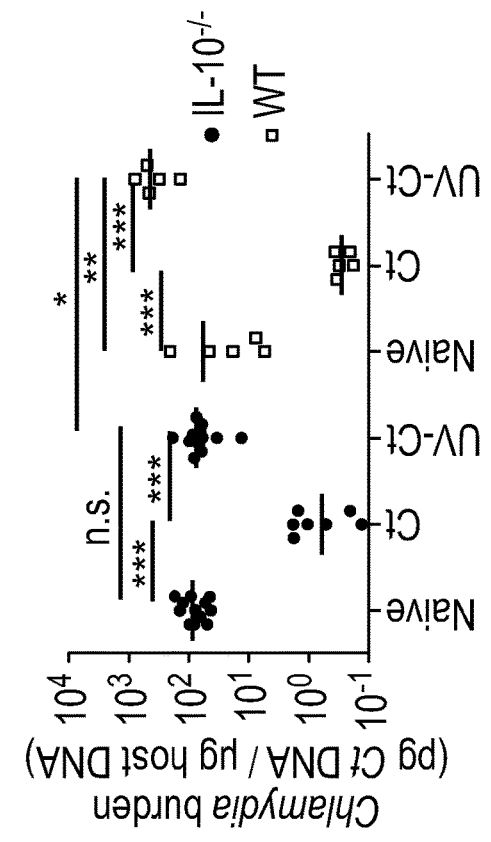
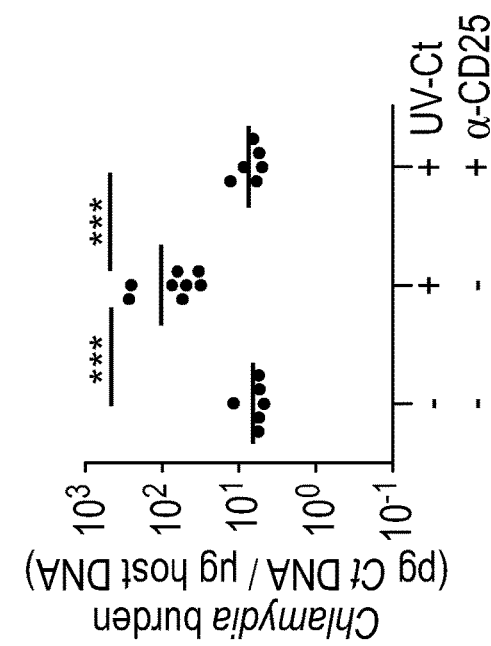

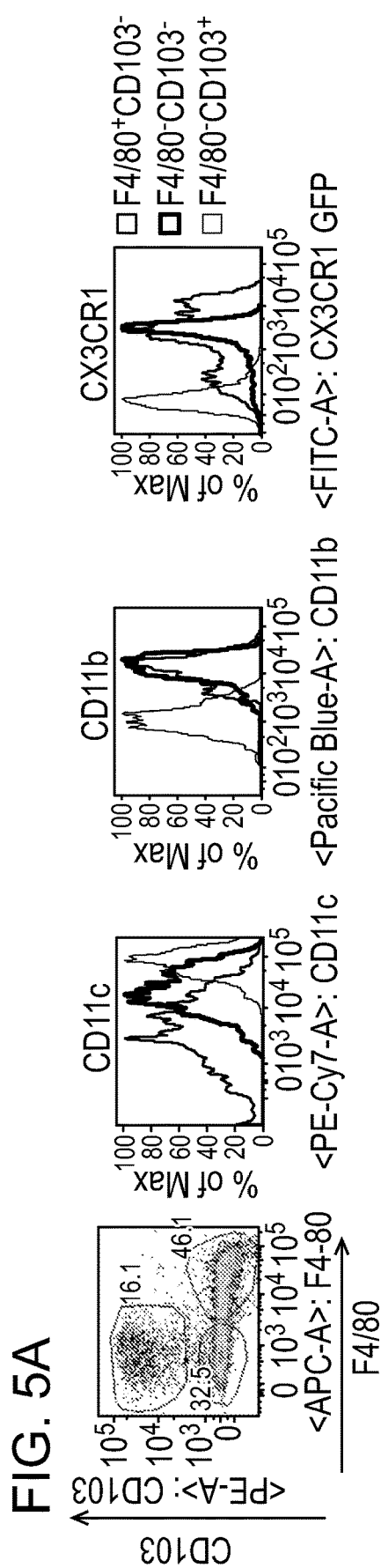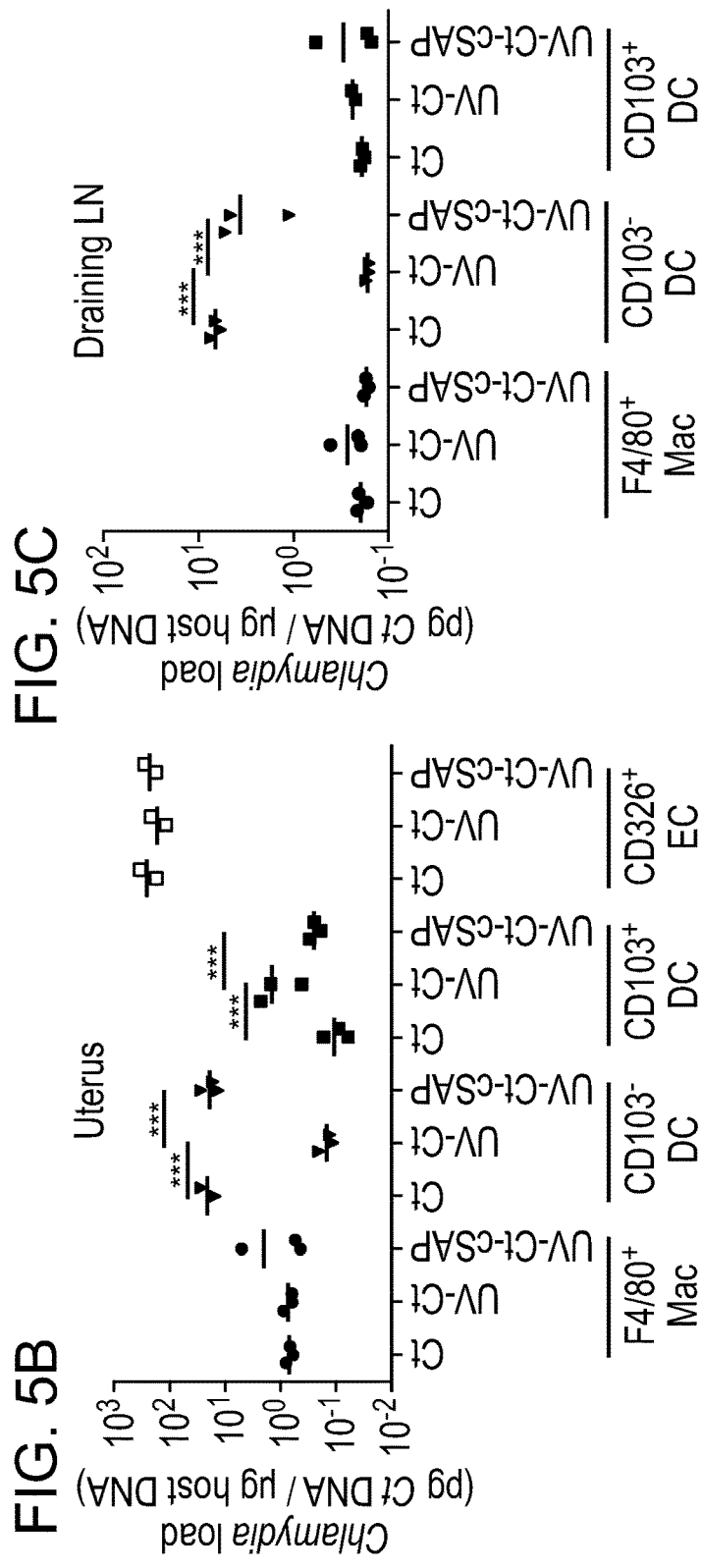
FIG. 5A
FIG. 5B
FIG. 5C

NANOPARTICLE-BASED COMPOSITIONS

CROSS-REFERENCE TO RELATED APPLICATIONS

This application is a 371 of PCT Application No. PCT/US2014/029000, filed on Mar. 14, 2014, which claims priority to U.S. Patent Application No. 61/783,439, filed on Mar. 14, 2013, the entire contents of both of which are hereby incorporated herein by reference.

STATEMENT AS TO FEDERALLY SPONSORED RESEARCH

This invention was made with Government support under NIH/RO1 AI069259 and NIH/RO1 AI072252, awarded by the National Institutes of Health. The Government has certain rights in the invention.

TECHNICAL FIELD

This invention relates to compositions and adjuvant compositions comprising nanoparticles.

BACKGROUND

The mucosal membranes are one of the largest organs in the body, and comprise the linings of the gastrointestinal, urogenital, and respiratory tracts. These mucosal membranes, while located in the body, are actually physical barriers between the external environment and the sterile internal body cavity known as the systemic environment. Thus, an important function of the mucosal membranes is to keep invading pathogens out of the sterile body cavity. Indeed, a vast majority of human pathogens, including bacteria, viruses, parasites and fungi, initiate infections at the mucosal surfaces (Ogra et al., Clin Microbiol Rev. 14(2):430-45, 2001).

Mucosal immunity is important because stimulation of the mucosal immune response can result in the production of protective B cells and T cells in both mucosal and systemic environments so that infections are stopped before the pathogens enter into the interior body cavity (see, e.g., McCluskie et al., Microbes Infect. 1(9):685-98; 1999; Rosenthal et al., Semin Immunol. 9(5):303-14, 1997). Despite its important role, very few vaccines specifically target the mucosal immune system.

Vaccinations can be either passive or active. Canonically, active vaccinations involve the exposure of an individual's immune system to one or more foreign molecules that elicit an endogenous immune response resulting in the activation of antigen-specific naive lymphocytes that subsequently leads to antibody-secreting B cells or antigen-specific effector and memory T cells. This approach can result in long-lived protective immunity that can be boosted from time to time by renewed exposure to the same antigenic material. The prospect of longevity of a successful immune response to active vaccination makes this strategy more desirable in most clinical settings than passive vaccination whereby a recipient is injected with preformed antibodies or with antigen-specific effector lymphocytes, which can confer rapid protection, but typically do not establish persistent immunity.

SUMMARY

The present disclosure is based, at least in part, on the development of new compositions including one or more adjuvant-loaded polymeric nanoparticles attached to an inactivated pathogen. For example, the new compositions include an inactivated pathogen, e.g., a bacterium, such as a *Chlamydia trachomatis*, *Francisella tularensis*, *Mycobacterium tuberculosis*, *Streptococcus pneumoniae*, *Listeria monocytogenes*, *Vibrio cholera*, *Shigella sonnei*, *Shigella flexneri*, or *Salmonella typhimurium*, or a virus, such as a human respiratory syncytial virus (RSV), an Influenza virus, human immunodeficiency virus (HIV), or a Hepatitis C virus, and one or more polymeric nanoparticles that are loaded with one or more adjuvants, such as a Toll-like receptor agonist, e.g., the imidazoquinoline resiquimod (R-848), monophosphoryl lipid A, or an unmethylated CpG oligodeoxynucleotide, or an endosomal membrane targeting agent, e.g., the Endo-Porter peptide. The polymeric nanoparticles can be formed by biodegradable polymers, e.g., poly(lactic-co-glycolic acid)-block-poly(L-histidine)-block-poly(ethylene glycol) (PLGA-PLH-PEG) triblock copolymers. One or more of the adjuvant-loaded nanoparticles are bound to each of the inactivated pathogens. These compositions are useful as vaccines for preventing and/or treating diseases caused by the specific pathogens, especially when administered to a subject's mucosal membranes.

Provided herein are also methods for stimulating in a subject a mucosal immune response against a pathogen, e.g., a bacterium, virus, parasite, or fungus, by administering to the subject the new vaccine compositions described herein through mucosal administration, e.g., by an ocular, intranasal, oral, buccal, sublingual, tonsilar, by inhalation, e.g., pulmonary or bronchial, gastric, intestinal, rectal, vaginal, or urinary tract route.

In some embodiments, the one or more adjuvant-loaded polymeric nanoparticles are surface charged and attached to the inactivated pathogen through electrostatic attraction. In some embodiments, the one or more adjuvant-loaded polymeric nanoparticles are attached to the inactivated pathogen through a linker, e.g., an attachment mechanism such as a monoclonal antibody, aptamer, antibiotic, lectin, or antimicrobial peptide that binds specifically to a surface molecule on the inactivated pathogen.

For example, a *Chlamydia trachomatis* vaccine composition including an inactivated *Chlamydia trachomatis* attached to one or more R848-loaded polymeric nanoparticles was made and evaluated in mouse models. While inactivated *Chlamydia trachomatis* alone induce immune tolerance, the new *Chlamydia trachomatis* vaccine compositions, when administered through a mucosal route, e.g., intranasally or intrauterinely, were effective in preventing subsequent *Chlamydia trachomatis* infection. Currently there are no vaccines available for use in humans against *Chlamydia trachomatis* infection. Thus, these new *Chlamydia trachomatis* vaccine compositions are promising new prophylactic and therapeutic vaccines against *Chlamydia trachomatis* infection in humans.

In general, in one aspect the disclosure features methods of stimulating a mucosal immune response against one or more different types of pathogen, e.g., *Chlamydia trachomatis* or *Francisella tularensis* in a subject in need thereof. The methods include administering to the subject a composition that includes an inactivated form of the pathogen, and one or more adjuvant-loaded polymeric nanoparticles, wherein the one or more adjuvant-loaded polymeric nanoparticles are each attached to the inactivated pathogen.

In these methods, the pathogen can be a bacterium, virus, parasite, and/or fungus, and the compositions can be administered to the subject through one or more mucosal routes, e.g., an ocular, intranasal, oral, buccal, sublingual, tonsilar, pulmonary, gastric, intestinal, rectal, vaginal, and/or urinary tract route.

In some implementations of these methods, the one or more adjuvant-loaded polymeric nanoparticles can include an adjuvant that targets an endosomal membrane, and/or the adjuvant-loaded polymeric nanoparticles can include a Toll-like receptor agonist, e.g., R848, monophosphoryl lipid A, or an unmethylated CpG oligodeoxynucleotide.

In certain embodiments the one or more adjuvant-loaded polymeric nanoparticles can be made of biodegradable polymers, such as poly(lactic-co-glycolic acid)-block-poly(L-histidine)-block-poly(ethylene glycol) (PLGA-PLH-PEG) triblock copolymers. In some embodiments the one or more adjuvant-loaded polymeric nanoparticles are attached to the inactivated pathogen through electrostatic attraction. In other embodiments the one or more adjuvant-loaded polymeric nanoparticles are attached to the inactivated pathogen through one or more linkers, e.g., an attachment mechanism such as a monoclonal antibody, an aptamer, an antibiotic, a lectin, and/or an antimicrobial peptide that binds specifically to a surface molecular of the inactivated pathogen.

In some embodiments, disclosed herein are methods for stimulating in a subject a mucosal immune response against bacteria selected from the group consisting of *Actinomyces, Anabaena, Bacillus, Bacteroides, Bdellovibrio, Bordetella, Borrelia, Brucella, Campylobacter, Caulobacter, Chlamydia, Chlorobium, Chromatium, Clostridium, Corynebacterium, Cytophaga, Deinococcus, Enterococcus, Escherichia, Francisella, Halobacterium, Heliobacter, Haemophilus, Hyphomicrobium, Legionella, Leptspirosis, Listeria, Meningococcus* A, B, and C, *Methanobacterium, Micrococcus, Mycobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus, Treponema, Vibrio*, and *Yersinia*. In some embodiments, methods for stimulating in a subject a mucosal immune response against *Chlamydia trachomatis* are provided. In some embodiments, methods for stimulating in a subject a mucosal immune response against *Francisella tularensis* are provided. In some embodiments, methods for stimulating in a subject a mucosal immune response against *Mycobacterium tuberculosis* are provided.

In some embodiments, disclosed herein are methods for stimulating in a subject a mucosal immune response against viruses selected from the group consisting of Adenoviridae, Arenaviridae, Arterivirus, Astroviridae, Baculoviridae, Badnavirus, Bamaviridae, Bimaviridae, Bromoviridae, Bunyaviridae, Caliciviridae, Capillovirus, Carlavirus, Caulimovirus, Circoviridae, Closterovirus, Comoviridae, Coronaviridae, Corticoviridae, Cystoviridae, Deltavirus, Dianthovirus, Enamovirus, Flaviviridae, Filoviridae, Flaviviridae, Hepadnaviridae, Herpesviridae, Hypoviridae, Iridoviridae, Leviviridae, Lipothrixviridae, Microviridae, Orthomyxoviridae, Papillomaviridae, Papovaviridae, Paramyxoviridae, Parvoviridae, Picornaviridae, Polyomaviridae, Poxviridae, Reoviridae, Retroviridae, Rhabdoviridae, Togaviridae, and Totiviridae. In some embodiments, methods for stimulating in a subject a mucosal immune response against human respiratory syncytial viruses are provided. In some embodiments, methods for stimulating in a subject a mucosal immune response against SARS coronaviruses are provided. In some embodiments, methods for stimulating in a subject a mucosal immune response against Noroviruses are provided. In some embodiments, methods for stimulating in a subject a mucosal immune response against human immunodeficiency viruses are provided.

In another general aspect, the disclosure includes compositions that include one or more different types of inactivated pathogens, e.g., *Chlamydia trachomatis* or *Francisella tularensis*; and one or more adjuvant-loaded polymeric nanoparticles, wherein the one or more adjuvant-loaded polymeric nanoparticles are each attached to the inactivated pathogen through an attachment mechanism. In these compositions the inactivated pathogen can be an inactivated bacterium, an inactivated virus, an inactivated parasite, and/or an inactivated fungus. For example, the inactivated pathogen can be an inactivated bacterium selected from the group consisting of *Chlamydia trachomatis, Francisella tularensis, Mycobacterium tuberculosis, Streptococcus pneumoniae, Listeria monocytogenes, Vibrio cholera, Shigella sonnei, Shigella flexneri*, and/or *Salmonella typhimurium*. In some embodiments, the compositions disclosed herein consist of, or consist essentially of, one or more different types of inactivated pathogens, e.g., *Chlamydia trachomatis* or *Francisella tularensis*; and one or more adjuvant-loaded polymeric nanoparticles, wherein the one or more adjuvant-loaded polymeric nanoparticles are each attached to the inactivated pathogen through an attachment mechanism.

In some implementations, the one or more adjuvant-loaded polymeric nanoparticles include an adjuvant that targets an endosomal membrane and/or a Toll-like receptor agonist. For example, the Toll-like receptor agonist can be R848 or an unmethylated CpG oligodeoxynucleotide.

In various implementations, the one or more adjuvant-loaded polymeric nanoparticles can be made of biodegradable polymers, e.g., poly(lactic-co-glycolic acid)-block-poly(L-histidine)-block-poly(ethylene glycol) (PLGA-PLH-PEG) triblock copolymers. In certain embodiments, the one or more adjuvant-loaded polymeric nanoparticles are attached to the inactivated pathogen through electrostatic attraction. In other embodiments, the one or more adjuvant-loaded polymeric nanoparticles are attached to the inactivated pathogen through a linker, e.g., an attachment mechanism such as one or more of a monoclonal antibody, an aptamer, an antibiotic, a lectin, or an antimicrobial peptide that binds specifically to a surface molecular of the inactivated pathogen.

The compositions can be designed in a form suitable for mucosal administration, e.g., via an ocular, intranasal, oral, buccal, sublingual, tonsilar, pulmonary, gastric, intestinal, rectal, vaginal, or urinary tract route as described in further detail herein.

In some embodiments, the compositions disclosed herein include inactivated bacteria selected from the group consisting of *Actinomyces, Anabaena, Bacillus, Bacteroides, Bdellovibrio, Bordetella, Borrelia, Brucella, Campylobacter, Caulobacter, Chlamydia, Chlorobium, Chromatium, Clostridium, Corynebacterium, Cytophaga, Deinococcus, Enterococcus, Escherichia, Francisella, Halobacterium, Heliobacter, Haemophilus, Hyphomicrobium, Legionella, Leptspirosis, Listeria, Meningococcus* A, B, and C, *Methanobacterium, Micrococcus, Mycobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus, Treponema, Vibrio*, and *Yersinia*. In some embodiments, the compositions disclosed herein include inactivated *Chlamydia trachomatis*. In some embodiments, the compositions disclosed herein include inactivated *Francisella tularensis*. In some embodiments, the compositions disclosed herein include inactivated *Mycobacterium tuberculosis*.

In some embodiments, the compositions disclosed herein include inactivated viruses selected from the group consisting of Adenoviridae, Arenaviridae, Arterivirus, Astroviridae, Baculoviridae, Badnavirus, Bamaviridae, Bimaviridae, Bromoviridae, Bunyaviridae, Caliciviridae, Capillovirus, Carlavirus, Caulimovirus, Circoviridae, Closterovirus, Comoviridae, Coronaviridae, Corticoviridae, Cystoviridae, Deltavirus, Dianthovirus, Enamovirus, Flaviviridae, Filoviridae, Flaviviridae, Hepadnaviridae, Herpesviridae, Hypoviridae, Iridoviridae, Leviviridae, Lipothrixviridae, Microviridae, Orthomyxoviridae, Papillomaviridae, Papovaviridae, Paramyxoviridae, Parvoviridae, Picornaviridae, Polyomaviridae, Poxviridae, Reoviridae, Retroviridae, Rhabdoviridae, Togaviridae, and Totiviridae. In some embodiments, the compositions disclosed herein include inactivated human respiratory syncytial viruses. In some embodiments, the compositions disclosed herein include inactivated SARS coronaviruses. In some embodiments, the compositions disclosed herein include inactivated Noroviruses. In some embodiments, the compositions disclosed herein include inactivated human immunodeficiency viruses.

In some embodiments, the disclosure includes compositions that include inactivated *Chlamydia trachomatis*; and one or more adjuvant-loaded polymeric nanoparticles, wherein the one or more adjuvant-loaded polymeric nanoparticles are each attached to the inactivated *Chlamydia trachomatis*. In some implementations, the one or more adjuvant-loaded polymeric nanoparticles include an adjuvant that targets an endosomal membrane and/or a Toll-like receptor agonist. For example, the adjuvant can be one or more of R848, unmethylated CpG oligodeoxynucleotide, and monophosphoryl lipid A. In some embodiments, the adjuvant is R848. In various implementations, the one or more adjuvant-loaded polymeric nanoparticles can be made of biodegradable polymers, e.g., poly(lactic-co-glycolic acid)-block-poly(L-histidine)-block-poly(ethylene glycol) (PLGA-PLH-PEG) triblock copolymers. In certain embodiments, the one or more adjuvant-loaded polymeric nanoparticles are attached to the inactivated *Chlamydia trachomatis* through electrostatic attraction. In other embodiments, the one or more adjuvant-loaded polymeric nanoparticles are attached to the inactivated *Chlamydia trachomatis* through a linker, e.g., an attachment mechanism such as one or more of a monoclonal antibody, an aptamer, an antibiotic, a lectin, or an antimicrobial peptide that binds specifically to a surface molecular of the inactivated pathogen. The compositions can be designed in a form suitable for mucosal administration, e.g., via an ocular, intranasal, oral, buccal, sublingual, tonsilar, pulmonary, gastric, intestinal, rectal, vaginal, or urinary tract route. In some embodiments, methods for stimulating in a subject a mucosal immune response against *Chlamydia trachomatis* by administering the compositions described herein are provided.

In some embodiments, the disclosure includes compositions that include inactivated *Francisella tularensis*; and one or more adjuvant-loaded polymeric nanoparticles, wherein the one or more adjuvant-loaded polymeric nanoparticles are each attached to the inactivated *Francisella tularensis*. In some implementations, the one or more adjuvant-loaded polymeric nanoparticles include an adjuvant that targets an endosomal membrane and/or a Toll-like receptor agonist. For example, the adjuvant can be one or more of R848, unmethylated CpG oligodeoxynucleotide, and monophosphoryl lipid A. In some embodiments, the adjuvant is R848. In various implementations, the one or more adjuvant-loaded polymeric nanoparticles can be made of biodegradable polymers, e.g., poly(lactic-co-glycolic acid)-block-poly(L-histidine)-block-poly(ethylene glycol) (PLGA-PLH-PEG) triblock copolymers. In certain embodiments, the one or more adjuvant-loaded polymeric nanoparticles are attached to the inactivated *Francisella tularensis* through electrostatic attraction. In other embodiments, the one or more adjuvant-loaded polymeric nanoparticles are attached to the inactivated *Francisella tularensis* through a linker, e.g., an attachment mechanism such as one or more of a monoclonal antibody, an aptamer, an antibiotic, a lectin, or an antimicrobial peptide that binds specifically to a surface molecular of the inactivated pathogen. The compositions can be designed in a form suitable for mucosal administration, e.g., via an ocular, intranasal, oral, buccal, sublingual, tonsilar, pulmonary, gastric, intestinal, rectal, vaginal, or urinary tract route. In some embodiments, methods for stimulating in a subject a mucosal immune response against *Francisella tularensis* by administering the compositions described herein are provided.

In some embodiments, the disclosure includes compositions that include inactivated *Mycobacterium tuberculosis*; and one or more adjuvant-loaded polymeric nanoparticles, wherein the one or more adjuvant-loaded polymeric nanoparticles are each attached to the inactivated *Mycobacterium tuberculosis*. In some implementations, the one or more adjuvant-loaded polymeric nanoparticles include an adjuvant that targets an endosomal membrane and/or a Toll-like receptor agonist. For example, the adjuvant can be one or more of R848, unmethylated CpG oligodeoxynucleotide, and monophosphoryl lipid A. In some embodiments, the adjuvant is monophosphoryl lipid A. In various implementations, the one or more adjuvant-loaded polymeric nanoparticles can be made of biodegradable polymers, e.g., poly(lactic-co-glycolic acid)-block-poly(L-histidine)-block-poly(ethylene glycol) (PLGA-PLH-PEG) triblock copolymers. In certain embodiments, the one or more adjuvant-loaded polymeric nanoparticles are attached to the inactivated *Mycobacterium tuberculosis* through electrostatic attraction. In other embodiments, the one or more adjuvant-loaded polymeric nanoparticles are attached to the inactivated *Mycobacterium tuberculosis* through a linker, e.g., an attachment mechanism such as one or more of a monoclonal antibody, an aptamer, an antibiotic, a lectin, or an antimicrobial peptide that binds specifically to a surface molecular of the inactivated pathogen. The compositions can be designed in a form suitable for mucosal administration, e.g., via an ocular, intranasal, oral, buccal, sublingual, tonsilar, pulmonary, gastric, intestinal, rectal, vaginal, or urinary tract route. In some embodiments, methods for stimulating in a subject a mucosal immune response against *Mycobacterium tuberculosis* by administering the compositions described herein are provided.

In some embodiments, the disclosure includes compositions that include inactivated human respiratory syncytial viruses (RSV); and one or more adjuvant-loaded polymeric nanoparticles, wherein the one or more adjuvant-loaded polymeric nanoparticles are each attached to the inactivated human respiratory syncytial viruses. In some implementations, the one or more adjuvant-loaded polymeric nanoparticles include an adjuvant that targets an endosomal membrane and/or a Toll-like receptor agonist. For example, the adjuvant can be one or more of R848, unmethylated CpG oligodeoxynucleotide, and monophosphoryl lipid A. In some embodiments, the adjuvant is R848. In various implementations, the one or more adjuvant-loaded polymeric nanoparticles can be made of biodegradable polymers, e.g., poly(lactic-co-glycolic acid)-block-poly(L-histidine)-block-poly(ethylene glycol) (PLGA-PLH-PEG) triblock copolymers. In certain embodiments, the one or more adjuvant-loaded polymeric nanoparticles are attached to the inactivated human respiratory syncytial viruses through electrostatic attraction. In other embodiments, the one or more adjuvant-loaded polymeric nanoparticles are attached to the inactivated human respiratory syncytial viruses through a linker, e.g., an attachment mechanism such as one or more of a monoclonal antibody, an aptamer, an antibiotic, a lectin, or an antimicrobial peptide that binds specifically to a surface molecular of the inactivated pathogen. The compositions can be designed in a form suitable for mucosal administration, e.g., via an ocular, intranasal, oral, buccal, sublingual, tonsilar, pulmonary, gastric, intestinal, rectal, vaginal, or urinary tract route. In some embodiments, methods for stimulating in a subject a mucosal immune response against human respiratory syncytial viruses by administering the compositions described herein are provided.

In some embodiments, the disclosure includes compositions that include inactivated SARS coronaviruses; and one or more adjuvant-loaded polymeric nanoparticles, wherein the one or more adjuvant-loaded polymeric nanoparticles are each attached to the inactivated SARS coronaviruses. In some implementations, the one or more adjuvant-loaded polymeric nanoparticles include an adjuvant that targets an endosomal membrane and/or a Toll-like receptor agonist. For example, the adjuvant can be one or more of R848, unmethylated CpG oligodeoxynucleotide, and monophosphoryl lipid A. In some embodiments, the adjuvant is unmethylated CpG oligodeoxynucleotide. In various implementations, the one or more adjuvant-loaded polymeric nanoparticles can be made of biodegradable polymers, e.g., poly(lactic-co-glycolic acid)-block-poly(L-histidine)-block-poly(ethylene glycol) (PLGA-PLH-PEG) triblock copolymers. In certain embodiments, the one or more adjuvant-loaded polymeric nanoparticles are attached to the inactivated SARS coronaviruses through electrostatic attraction. In other embodiments, the one or more adjuvant-loaded polymeric nanoparticles are attached to the inactivated SARS coronaviruses through a linker, e.g., an attachment mechanism such as one or more of a monoclonal antibody, an aptamer, an antibiotic, a lectin, or an antimicrobial peptide that binds specifically to a surface molecular of the inactivated pathogen. The compositions can be designed in a form suitable for mucosal administration, e.g., via an ocular, intranasal, oral, buccal, sublingual, tonsilar, pulmonary, gastric, intestinal, rectal, vaginal, or urinary tract route. In some embodiments, methods for stimulating in a subject a mucosal immune response against SARS coronaviruses by administering the compositions described herein are provided.

In some embodiments, the disclosure includes compositions that include inactivated Noroviruses; and one or more adjuvant-loaded polymeric nanoparticles, wherein the one or more adjuvant-loaded polymeric nanoparticles are each attached to the inactivated Noroviruses. In some implementations, the one or more adjuvant-loaded polymeric nanoparticles include an adjuvant that targets an endosomal membrane and/or a Toll-like receptor agonist. For example, the adjuvant can be one or more of R848, unmethylated CpG oligodeoxynucleotide, and monophosphoryl lipid A. In some embodiments, the adjuvant is unmethylated CpG oligodeoxynucleotide. In various implementations, the one or more adjuvant-loaded polymeric nanoparticles can be made of biodegradable polymers, e.g., poly(lactic-co-glycolic acid)-block-poly(L-histidine)-block-poly(ethylene glycol) (PLGA-PLH-PEG) triblock copolymers. In certain embodiments, the one or more adjuvant-loaded polymeric nanoparticles are attached to the inactivated Noroviruses through electrostatic attraction. In other embodiments, the one or more adjuvant-loaded polymeric nanoparticles are attached to the inactivated Noroviruses through a linker, e.g., an attachment mechanism such as one or more of a monoclonal antibody, an aptamer, an antibiotic, a lectin, or an antimicrobial peptide that binds specifically to a surface molecular of the inactivated pathogen. The compositions can be designed in a form suitable for mucosal administration, e.g., via an ocular, intranasal, oral, buccal, sublingual, tonsilar, pulmonary, gastric, intestinal, rectal, vaginal, or urinary tract route. In some embodiments, methods for stimulating in a subject a mucosal immune response against Noroviruses by administering the compositions described herein are provided.

In some embodiments, the disclosure includes compositions that include inactivated human immunodeficiency viruses; and one or more adjuvant-loaded polymeric nanoparticles, wherein the one or more adjuvant-loaded polymeric nanoparticles are each attached to the inactivated human immunodeficiency viruses. In some implementations, the one or more adjuvant-loaded polymeric nanoparticles include an adjuvant that targets an endosomal membrane and/or a Toll-like receptor agonist. For example, the adjuvant can be one or more of R848, unmethylated CpG oligodeoxynucleotide, and monophosphoryl lipid A. In some embodiments, the adjuvant is monophosphoryl lipid A. In various implementations, the one or more adjuvant-loaded polymeric nanoparticles can be made of biodegradable polymers, e.g., poly(lactic-co-glycolic acid)-block-poly(L-histidine)-block-poly(ethylene glycol) (PLGA-PLH-PEG) triblock copolymers. In certain embodiments, the one or more adjuvant-loaded polymeric nanoparticles are attached to the inactivated human immunodeficiency viruses through electrostatic attraction. In other embodiments, the one or more adjuvant-loaded polymeric nanoparticles are attached to the inactivated human immunodeficiency viruses through a linker, e.g., an attachment mechanism such as one or more of a monoclonal antibody, an aptamer, an antibiotic, a lectin, or an antimicrobial peptide that binds specifically to a surface molecular of the inactivated pathogen. The compositions can be designed in a form suitable for mucosal administration, e.g., via an ocular, intranasal, oral, buccal, sublingual, tonsilar, pulmonary, gastric, intestinal, rectal, vaginal, or urinary tract route. In some embodiments, methods for stimulating in a subject a mucosal immune response against human immunodeficiency viruses by administering the compositions described herein are provided.

A "pathogen" as used herein is an infectious agent that causes diseases in its host. A pathogen can be a bacterium, virus, parasite, fungus, or other microbial infectious agent.

As used herein, a "nanoparticle" is a particle in the range of between 500 nm to less than 0.5 nm, e.g., having a diameter that is between 50 and 500 nm.

As used herein, the term "adjuvant" refers to an immunological adjuvant. By this is meant a compound or composition that is able to enhance or facilitate the immune system's response to a pathogen, thereby inducing an immune response or series of immune responses in the subject. The adjuvant can facilitate the effect of the compositions, for example, by forming depots (prolonging the half-life of the composition), provide additional T-cell help, and/or stimulate cytokine production.

As used herein, a "subject" is an animal, e.g., a mammal, e.g., a human, monkey, dog, cat, horse, cow, pig, goat, rabbit, or mouse.

As used herein, "treatment" can be prophylactic or therapeutic. Prophylactic treatment can be used to treat a subject at a risk of developing disease from an infectious pathogen. An individual traveling to or living in an area of endemic infectious disease may be considered to be at risk and a candidate for prophylactic vaccination against the particular infectious pathogen. Therapeutic treatment with vaccines can be used to initiate or enhance a subject's immune response to a contracted pathogen.

As generally used herein, an "effective amount" is the amount that is sufficient to induce a protective immune response in the treated subject. The actual effective amounts of vaccine can vary according to the specific pathogen and adjuvant being utilized, the particular vaccine composition formulated, the mode of administration, and the age, weight, condition of the subject being vaccinated, as well as the route of administration and the disease or disorder.

As used herein, "immunostimulatory" means that a substance has a stimulating effect on the immune system. Such substances can be readily identified using standard assays which indicate various aspects of the immune response, such as cytokine secretion, antibody production, NK cell activation and T cell proliferation. See, e.g., WO 97/28259; WO 98/16247; WO 99/11275; Krieg et al. (1995) Nature 374:546-549; Yamamoto et al. (1992) J. Immunol. 148:4072-76; Ballas et al. (1996) J. Immunol. 157:1840-45; Klinman et al. (1997) J. Immunol. 158:3635-39; Sato et al. (1996) Science 273:352-354; Pisetsky (1996) J. Immunol. 156:421-423; Shimada et al. (1986) Jpn. J. Cancer Res. 77:808-816; Cowdery et al. (1996) J. Immunol. 156:4570-75; Roman et al. (1997) Nat. Med. 3:849-854; Lipford et al. (1997a) Eur. J. Immunol. 27:2340-44; WO 98/55495 and WO 00/61151. Accordingly, these and other methods can be used to identify, test and/or confirm immunostimulatory substances, such as immunostimulatory nucleotides, e immunostimulatory isolated nucleic acids.

As used herein, "couple" or "coupled" or "couples" (and the like) means to chemically associate one entity (for example a moiety) with another. In some implementations, the coupling is covalent, meaning that the coupling occurs in the context of the presence of a covalent bond between the two entities. In non-covalent implementations, the non-covalent coupling is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. In certain implementations, encapsulation is a form of coupling.

As used herein "encapsulate" means to enclose within a synthetic nanoparticle, preferably enclose completely within a synthetic nanoparticle. Most or all of a substance that is encapsulated is not exposed to the local environment external to the synthetic nanoparticle. Encapsulation is distinct from absorption, which places most or all of a substance on a surface of a synthetic nanoparticle, and leaves the substance exposed to the local environment external to the synthetic nanoparticle.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 1C-1D are bar graphs showing that the UV-Ct induced immune tolerance is mediated by FoxP3$^+$ Treg cells.

FIG. 1E is a dot plot showing that treatment with anti-CD25 monoclonal antibody overcomes UV-Ct induced immune tolerance, indicating that CD4$^+$ FoxP3$^+$ Treg cells play a critical role in mediating UV-Ct induced immune tolerance.

FIG. 1F is a dot plot showing IL-10 deficiency abrogated the inactivated *Chlamydia* induced immune tolerance, confirming that Treg-secreted IL-10 plays a critical role in the inactivated *Chlamydia* induced immune tolerance.

FIG. 5A is a set of flow cytometry graphs showing that F4/80$^+$ CD103$^-$ macrophages express high level of CD11b and CX3CR1 but low level of CD11c; F4/80$^-$ CD103$^-$ dendritic cells express high level of CD11c, CD11b, and CX3CR1; F4/80$^-$ CD103$^+$ dendritic cells express low level of CD11b and CX3 CR1, but high level of CD11c.

FIGS. 5B and 5C are a set of dot plots showing CD103$^-$ dendritic cells had a significantly higher *Chlamydia* loads than F4/80$^+$ macrophages and CD103$^+$ dendritic cells in both uteri (5B) and lymph nodes (5C), indicating CD103$^-$ dendritic cells play important roles in recognizing and presenting *Chlamydia*.

Figure 1A:
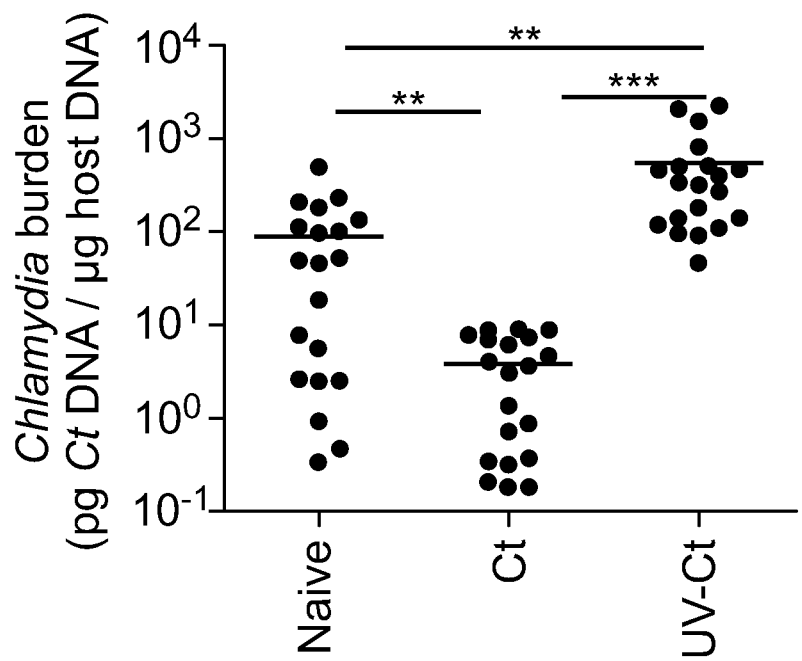
FIG. 1A is a dot plot showing intrauterine immunization with UV-inactivated Ct (UV-Ct) resulted in enhanced susceptibility to subsequent live *Chlamydia* challenge, indicating immune tolerance is induced by UV-Ct.

For all figures, *=p<0.05, =p<0.01, *=p<0.001.

DETAILED DESCRIPTION

The present disclosure is based, at least in part, on the development of new vaccine compositions comprising one or more adjuvant-loaded polymeric nanoparticles attached to an inactivated pathogen. For example, the new vaccine compositions comprise an inactivated pathogen, e.g., a bacterium, such as a *Chlamydia trachomatis, Francisella tularensis, Mycobacterium tuberculosis, Streptococcus pneumoniae, Listeria monocytogenes, Vibrio cholera, Shigella sonnei, Shigella flexneri*, or *Salmonella typhimurium*, or a virus, such as an Influenza virus, a human respiratory syncytial virus (RSV), human immunodeficiency virus (HIV), Hepatitis C virus, and one or more polymeric nanoparticles that are loaded with adjuvants, such as a Toll-like receptor agonist, e.g., the imidazoquinoline resiquimod (R-848), monophosphoryl lipid A, or an unmethylated CpG oligodeoxynucleotide, or an endosomal membrane targeting agent, e.g., the Endo-Porter peptide. One or more of the adjuvant-loaded nanoparticles are bound to each of the inactivated pathogens. These vaccine compositions are useful for preventing and/or treating diseases caused by the specific pathogens, especially when administered to a subject's mucosal membranes.

The vaccine compositions disclosed herein include one or more adjuvant-loaded nanoparticles attached to each of the inactivated whole pathogens, e.g., via an attachment mechanism. This attachment mechanism can be an electrostatic attraction, covalent coupling, or a hydrophobic interaction. The adjuvants can be a dendritic cell targeting molecule, for example, a Toll-like receptor agonist, e.g., R-848, which is recognized as a potent synthetic agonist of TLR7/TLR8, or an unmethylated CpG oligodeoxynucleotide, which is immunostimulatory agonist of TLR-9, or monophosphoryl lipid A, which is immunostimulatory agonist of TLR-4, or an endosomal membrane targeting agent, e.g., the Endo-Porter peptide.

A vast majority of vaccines available today target the systemic immune system and block disease progression after the pathogens have crossed the mucosal barrier and entered into the normally sterile systemic environment. The vaccine compositions disclosed herein can target the mucosal membranes and stimulate mucosal immunity in an immunized subject that protects the subject from infection by an active form of the inactivated pathogens included in the vaccine. These vaccine compositions achieve immune protection either by preventing initial colonization and replication of the pathogens or by blocking further infection progression. Thus, these vaccine compositions are both prophylactic and therapeutic.

Inactivated Pathogens

A "pathogen" as used herein is an infectious agent that causes diseases in its host. A pathogen can be a bacterium, virus, parasite, fungus, or other microbial infectious agent. Many vaccines against pathogens comprise live or attenuated microorganisms. However, live or attenuated vaccines can sometimes cause infectious pathologies, especially when administered to immune-compromised recipients. Other vaccines utilize one or more purified components of pathogen lysates, such as one or more surface carbohydrates or recombinant pathogen-derived proteins. However, incomplete protection can be seen in this type of vaccines due to partial presentation of pathogenic antigens. Those pathogenic antigens not included in the vaccines can still cause infectious pathologies in an immunized individual.

The vaccine compositions disclosed herein include one or more inactivated whole pathogens, for example, inactivated bacteria, inactivated viruses, inactivated parasites, or inactivated fungi. Recipients of the vaccine compositions disclosed herein are presented with a full spectrum of pathogenic antigens of a particular pathogen, and thus gain complete immune protection against that pathogen.

Whole pathogens can be inactivated by a physical or chemical treatment known in the art, for example, by exposure to UV light, elevated temperature, fixation, ionizing radiation, paraformaldehyde, formalin, hydroxylamine, phenol, polysorbate, and the like. The type of inactivation method can be chosen with a view to retain the immunogenicity of the whole pathogen.

Bacterial pathogens cause bacterial diseases such as Anthrax, Bacterial Meningitis, Botulism, Brucellosis, Cat Scratch Disease, Cholera, Diphtheria, Epidemic Typhus, Gonorrhea, Impetigo, Leprosy (Hansen's Disease), Listeriosis, Rheumatic Fever; Nocardiosis, Pertussis (Whooping Cough), Plague, Pneumococcal pneumonia, Psittacosis, Q fever, Rocky Mountain Spotted Fever (RMSF), *Salmonellosis*, Scarlet Fever, Shigellosis, Syphilis, Tetanus, Trachoma, Tuberculosis, Tularemia, Typhoid Fever, Typhus and Urinary Tract Infections.

One or more inactivated whole bacteria can be used as pathogens in the vaccine compositions disclosed herein and can be derived from any of the following bacterial genera: *Actinomyces, Anabaena, Bacillus* (e.g. *Bacillus anthracis*), *Bacteroides, Bdellovibrio, Bordetella, Borrelia, Brucella, Campylobacter, Caulobacter, Chlamydia, Chlorobium, Chromatium, Clostridium, Corynebacterium, Cytophaga, Deinococcus, Enterococcus, Escherichia, Francisella* (e.g. *Francisella tularensis*), *Halobacterium, Heliobacter, Haemophilus* (e.g., *Hemophilus influenza* type B), *Hyphomicrobium, Legionella, Leptspirosis, Listeria, Meningococcus* A, B, and C, *Methanobacterium, Micrococcus, Mycobacterium* (e.g. *Mycobacterium tuberculosis*), *Mycoplasma, Myxococcus, Neisseria, Nitrobacter, Oscillatoria, Prochloron, Proteus, Pseudomonas* (e.g. *Pseudomonas pneumonia*), *Phodospirillum, Rickettsia, Salmonella, Shigella, Spirillum, Spirochaeta, Staphylococcus, Streptococcus* (e.g. *Streptococcus pneumonia*), *Streptomyces, Sulfolobus, Thermoplasma, Thiobacillus, Treponema, Vibrio* (e.g. *Vibrio cholera*), and *Yersinia*.

Viral pathogens cause viral diseases such as AIDS, AIDS-related complex, chickenpox, common cold-Influenza (Flu), dengue fever, foot and mouth disease, hepatitis, herpes simplex, HPV, Lassa fever, measles, mumps, poliomyelitis, rabies, SARS, Smallpox, viral encephalitis, viral gastroenteritis, viral meningitis, viral pneumonia, West Nile disease and Yellow fever.

One or more inactivated viruses can be used as pathogens in the vaccine compositions disclosed herein and can be derived from any of the following viral families: Adenoviridae, Arenaviridae, Arterivirus, Astroviridae, Baculoviridae, Badnavirus, Bamaviridae, Bimaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Flaviviridae, Filoviridae (e.g., Marburg virus and Ebola virus (e.g., Zaire, Reston, Ivory Coast, or Sudan strain)), Flaviviridae (e.g., Hepatitis C virus, Dengue virus 1, Dengue virus 2, Dengue virus 3, and Dengue virus 4), Hepadnaviridae, Herpesviridae (e.g., Human herpes virus I, 3, 4, S, and 6, and Cytomegalovirus), Hypoviridae, Iridoviridae, Leviviridae, Lipothrixviridae, Microviridae, Orthomyxoviridae (e.g., Influenza virus A and B and C), Papillomaviridae, Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Polyomaviridae, Poxviridae (e.g., vaccinia and smallpox virus), Reoviridae (e.g., rotavirus), Retroviridae (e.g., lentivirus, such as human immunodeficiency virus HIV I and HIV 2), Rhabdoviridae (for example, rabies virus, measles virus, respiratory syncytial virus, etc.), Togaviridae (for example, rubella virus, dengue virus, etc.), and Totiviridae.

Viral-based vaccines can also be made using virus-like particles or pseudotyped viruses that contain antigenic viral proteins, e.g., RSV, HIV, or Norovirus.

Parasitic pathogens cause parasitic diseases such as parasitic diseases such as African trypanosomiasis, Amebiasis, Ascariasis, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolopsiasis, Filariasis, Free-living amebic infection, Giardiasis, Gnathostomiasis, Hymenolepiasis, Isosporiasis, Kala-azar, Leishmaniasis, Malaria, Metagonimiasis, Myiasis, Onchocerciasis, Pediculosis, Pinworm Infection, Scabies, Schistosomiasis, Taeniasis, Toxocariasis, Toxoplasmosis, Trichinellosis, Trichinosis, Trichuriasis, Trichomoniasis and Trypanosomiasis.

One or more inactivated parasites can be used as pathogens in the vaccine compositions disclosed herein and can be derived from: e.g., *Ascaris lumbricoides, Babesia microti, Babesia duncani, Brugia malayi, Brugia timori, Clonorchis sinensis, Cryptosporidium, Diphyllobothrium, Dracunculus medinensis, Echinococcus granulosus, Entamoeba histolytica, Enterobius vermicularis, Fasciola hepatica, Fasciola gigantica, Fasciolopsis buski, Gardia lamblia, Gnathostoma, Hymenolepis, Isospora belli, Leishmania, Mansonella, Metagonimus, Naegleria fowleri, Onchocerca volvulus, Plasmodium Jalciparum, Sarcoptes scabiei, Schistosoma mansoni, Taenia solium, Toxocara, Toxoplasma gondii, Trichinella spiralis, Trichuris trichiura, Trichomonas vaginalis, Trypanosoma brucei, Trypanosoma cruzi, Toxoplasma gondii, Trichomonas vaginalis,* or *Wuchereria bancrofti.*

Pathogenic fungi cause fungal diseases such as Aspergillosis, Blastomycosis, Candidiasis, Coccidioidomycosis, Cryptococcosis, Histoplasmosis and Tinea pedis, in a host. One or more inactivated fungi can be used as pathogens in the vaccine compositions disclosed herein and can be derived from the fungal genera, e.g., *Aspergillus, Blastomyces, Candida, Coccidioides, Cryptococcus, Histoplasma, Pneumocystis, Stachybotrys, Trichophyton.*

Polymeric Nanoparticles

The vaccine and adjuvant compositions disclosed herein include one or more adjuvant-loaded nanoparticles or nanocarriers. The polymer that forms the nanoparticles can be any biodegradable or non-biodegradable synthetic or natural polymer. Preferably, the polymer is a biodegradable polymer. Examples of useful biodegradable polymers include polylactic acid (PLA), poly(glycolic acid) (PGA), or poly(lactic-co-glycolic acid) (PLGA). These polymers have an established safety record and can be used in human subjects (Jiang, et al., Adv. Drug Deliv. Rev., 57(3):391-410, 2005; Aguado and Lambert, Immunobiology, 184(2-3): 113-25, 1992; Bramwell, et al., Adv. Drug Deliv. Rev., 57(9):1247-65, 2005). Other amphiphilic poly(amino acid) nanoparticles, amphiphilic polysaccharide nanoparticles, or polyion nanoparticles can be used in the vaccine composition disclosed herein (see, Akagi et al., Adv Polym Sci. 247:31-64, 2012).

The foregoing polymers can be used alone, as physical mixtures, or by forming copolymers. In certain embodiments, the nanoparticles are formed by a mixture of poly(lactic-co-glycolic acid)-block-poly(L-histidine)-block-poly(ethylene glycol) (PLGA-PLH-PEG) triblock copolymer; PLGA-PEG diblock copolymer, and PLA. These copolymers can be synthesized using standard techniques. For example, the copolymer PLGA-PLH-PEG can be synthesized using a block end-grafting strategy.

A linear structure PLGA-PLH-PEG can provide the nanoparticles several characteristics compatible with extended circulation and charge-mediated targeting. First, the PLH segment becomes positively charged under acidic conditions, yielding an overall positive potential on the nanoparticle surface, facilitating interactions with negatively charged pathogens and producing strong multivalent electrostatic mediated binding. Second, the PLGA segment can form a solid core matrix without having the destabilizing force of the PLH at acidic pH. Third, the PLH segment rises to near the nanoparticle surface during polymer self-assembly, due to its intrinsic hydrophilicity under typical formulation conditions as well as its close association with the PEG, which would preferentially rise to the surface due to its relative hydrophilicity. This is significant, because it increases cationic charges at the nanoparticle surface. Third, having the PEG portion at the distal end of the polymer facilitates nanoparticle colloidal stability and circulation time at physiologic pH (Radovic-Moreno, et al., ACS Nano 6: 4279-4287, 2012; Gref et al., Science 263: 1600-1603, 1994).

In some embodiments, natural polymers can be used. Examples of natural polymers include alginate and other polysaccharides, collagen, albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Other suitable biodegradable polymers include, but are not limited to, poly(hydroxy acids), such as polymers and copolymers of lactic acid and glycolic acid, polyanhydrides, poly(ortho)esters, polyesters, polyurethanes, poly(butic acid), poly(valeric acid), poly(caprolactone), poly(hydroxyalkanoates), and poly(lactide-co-caprolactone).

The polymer can be a bioadhesive polymer that is hydrophilic or hydrophobic. Hydrophilic polymers include CARBOPOL™ (a high molecular weight, crosslinked, acrylic acid-based polymers manufactured by Noveon), polycarbophil, cellulose esters, and dextran.

These polymers can be obtained from sources such as Sigma Chemical Co., St. Louis, Mo.; Polysciences, Warrenton, Pa.; Aldrich, Milwaukee, Wis.; Fluka, Ronkonkoma, N.Y.; and BioRad, Richmond, Calif., or can be synthesized from monomers obtained from these or other suppliers using standard techniques.

A wide variety of polymers and methods for forming polymeric matrices therefrom are known conventionally. In general, a polymeric matrix comprises one or more polymers. Polymers can be natural or unnatural (synthetic) polymers. Polymers can be homopolymers or copolymers comprising two or more monomers. In terms of sequence, copolymers can be random, block, or comprise a combination of random and block sequences. Typically, polymers in accordance with the present invention are organic polymers.

Examples of polymers suitable for use in the present invention include, but are not limited to polyethylenes, polycarbonates (e.g. poly(1,3-dioxan-2one)), polyanhydrides (e.g. poly(sebacic anhydride)), polypropylfumarates, polyamides (e.g., polycaprolactam), polyacetals, polyethers, polyesters (e.g., polylactide, polyglycolide, polylactide-co-glycolide, polycaprolactone, polyhydroxyacid (e.g. poly(β-hydroxyalkanoate))), poly(orthoesters), polycyanoacrylates, polyvinyl alcohols, polyurethanes, polyphosphazenes, polyacrylates, polymethacrylates, polyureas, polystyrenes, and polyamines, polylysine, polylysine-PEG copolymers, and poly(ethyleneimine), poly(ethylene imine)-PEG copolymers.

In some implementations, polymers in accordance with the present invention include polymers that have been approved for use in humans by the U.S. Food and Drug Administration (FDA) under 21 C.F.R. § 177.2600, including but not limited to polyesters (e.g., polylactic acid, poly(lactic-co-glycolic acid), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates.

In some implementations, polymers can be hydrophilic. For example, polymers can comprise anionic groups (e.g., phosphate group, sulfate group, carboxylate group); cationic groups (e.g., quaternary amine group); or polar groups (e.g., hydroxyl group, thiol group, amine group). In some implementations, polymers can be hydrophobic. Selection of the hydrophilicity or hydrophobicity of the polymer can have an impact on the nature of materials that are incorporated (e.g., coupled) within the synthetic nanoparticle.

In some implementations, polymers can be modified with one or more moieties and/or functional groups. A variety of moieties or functional groups can be used in accordance with the present invention. In some implementations, polymers can be modified with polyethylene glycol (PEG), with a carbohydrate, and/or with acyclic polyacetals derived from polysaccharides (Papisov, 2001, ACS Symposium Series, 786:301). Certain implementations can be made using the general teachings of U.S. Pat. No. 5,543,158 to Gref et al., or WO publication WO2009/051837 by Von Andrian et al.

In some implementations, polymers can be modified with a lipid or fatty acid group. In some implementations, a fatty acid group can be one or more of butyric, caproic, caprylic, capric, lauric, myristic, palmitic, stearic, arachidic, behenic, or lignoceric acid. In some implementations, a fatty acid group can be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some implementations, polymers can be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some implementations, exemplary polyesters include, for example, polyhydroxyacids; PEG copolymers and copolymers of lactide and glycolide (e.g., PLA-PEG copolymers, PGA-PEG copolymers, PLGA-PEG copolymers, and derivatives thereof. In some implementations, polyesters include, for example, poly(caprolactone), poly(caprolactone)-PEG copolymers, poly(L-lactide-co-L-lysine), poly(serine ester), poly(4-hydroxy-L-proline ester), poly[α-(4-aminobutyl)-L-glycolic acid], and derivatives thereof. The degradation rate of PLGA can be adjusted by altering the lactic acid:glycolic acid ratio. In some implementations, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

In some implementations, polymers can be one or more acrylic polymers. In certain implementations, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer can comprise fully-polymerized copolymers of acrylic and methacrylic acid esters with a low content of quaternary ammonium groups.

In some implementations, polymers can be cationic polymers. In general, cationic polymers are able to condense and/or protect negatively charged strands of nucleic acids (e.g., DNA, or derivatives thereof) Amine-containing polymers such as poly(lysine) (Zauner et al., 1998, Adv. Drug Del. Rev., 30:97; and Kabanov et al., 1995, Bioconjugate Chem., 6:7), poly(ethylene imine) (PEI; Boussif et al., 1995, Proc. Natl. Acad. Sci., USA, 1995, 92:7297), and poly (amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372) are positively-charged at physiological pH, form ion pairs with nucleic acids, and mediate transfection in a variety of cell lines.

In some implementations, polymers can be degradable polyesters bearing cationic side chains (Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633).

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181). More generally, a variety of methods for synthesizing certain suitable polymers are described in Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732.

In some implementations, polymers can be linear or branched polymers. In some implementations, polymers can be dendrimers. In some implementations, polymers can be substantially cross-linked to one another. In some implementations, polymers can be substantially free of cross-links. In some implementations, polymers can be used in accordance with the present invention without undergoing a cross-linking step. It is further to be understood that inventive synthetic nanoparticles can comprise block copolymers, graft copolymers, blends, mixtures, and/or adducts of any of the foregoing and other polymers. Those skilled in the art will recognize that the polymers listed herein represent an exemplary, not comprehensive, list of polymers that can be of use in accordance with the present invention.

In some implementations, synthetic nanoparticles can optionally comprise one or more amphiphilic entities. In some implementations, an amphiphilic entity can promote the production of synthetic nanoparticles with increased stability, improved uniformity, or increased viscosity. In some implementations, amphiphilic entities can be associated with the interior surface of a lipid membrane (e.g., lipid bilayer, lipid monolayer, etc.). Many amphiphilic entities known in the art are suitable for use in making synthetic nanoparticles in accordance with the present invention. Such amphiphilic entities include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. An amphiphilic entity component can be a mixture of different amphiphilic entities. Those skilled in the art will recognize that this is an exemplary, not comprehensive, list of substances with surfactant activity. Any amphiphilic entity can be used in the production of synthetic nanoparticles to be used in accordance with the present invention.

In some implementations, synthetic nanoparticles can optionally comprise one or more carbohydrates. Carbohydrates can be natural or synthetic. A carbohydrate can be a derivatized natural carbohydrate. In certain implementations, a carbohydrate comprises monosaccharide or disaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain implementations, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan. In implementations, the inventive synthetic nanoparticles do not comprise (or specifically exclude) carbohydrates, such as a polysaccharide. In certain implementations, the carbohydrate can comprise a carbohydrate derivative such as a sugar alcohol, including but not limited to mannitol, sorbitol, xylitol, erythritol, maltitol, and lactitol.

Adjuvants

The vaccine and adjuvant compositions disclosed herein include adjuvant-loaded nanoparticles. One or more adjuvants can be encapsulated or otherwise entrapped in the nanoparticles, or can be associated with the surface of the nanoparticles.

As used herein, the term "adjuvant" refers to an immunological adjuvant. By this is meant a compound or composition that is able to enhance or facilitate the immune system's response to a pathogen, thereby inducing an immune response or series of immune responses in the subject. The adjuvant can facilitate the effect of the vaccine compositions, for example, by forming depots (prolonging the half-life of the vaccine), provide additional T-cell help, and/or stimulate cytokine production.

Dendritic cells are the most potent antigen-presenting cells in the body and are responsible for initiating all pathogen-specific immune responses by binding to the pathogenic antigens. Dendritic cells also communicate to T cells about the nature of the pathogen encountered through chemotactic signals, and induce proper T cell response. Thus, targeting dendritic cells can enhance the delivery and presentation of pathogenic antigens and control the nature of the immune responses induced by the vaccination.

In response to the different types of pathogens encountered, dendritic cells utilize different surface receptors to bind to the exposed pathogenic antigens. During migration, dendritic cells undergo a process of maturation in which they lose phagocytic capacity and develop an increased ability to communicate with T-cells in the lymph nodes. This maturation process is dependent on signaling from pathogen-associated molecular pattern (PAMP) molecules through pattern recognition receptors, such as the members of the Toll-like receptor family (TLR). PAMPs target the TLR on the surface of the dendritic cell and signal internally, thereby potentially increasing dendritic cell antigen uptake, maturation, and T-cell stimulatory capacity. TLR agonists therefore are potent dendritic cell activators and can be included in the vaccine compositions describe herein, e.g., CpG oligodeoxynucleotides (bacterial), double-stranded RNAs (viral), lipopolysaccharides (bacterial), peptidoglycans (bacterial), lipoarabinomannins (bacterial), zymosans (yeast), mycoplasmal lipoproteins such as MALP-2 (bacterial), flagellins (bacterial), poly(inosinic-cytidylic) acids (bacterial), lipoteichoic acids (bacterial) or imidazoquinolines (synthetic).

R848 (Resiquimod) is a guanosine derivative of imidazoquinoline and is an agonist for TLR7 and TLR8. R848 is an effective adjuvant that activates dendritic cells and B cells to produce cytokines optimal for T helper 1 (Th1) cell immunity and antibody production. Thus, R848 can be included as an adjuvant in the vaccine compositions disclosed herein to augment both humoral and cell mediated immune responses. Methods of using this adjuvant are described in detail in the examples below.

TLR9 specifically recognizes unmethylated CpG motifs, hallmark of microbial DNA, which can be mimicked by synthetic oligodeoxynucleotides containing CpG motifs. TLR9 stimulation by CpG DNA or CpG oligodeoxynucleotides triggers intracellular signaling leading to the activation of macrophages, dendritic cells and B cells, and the production of cytokines, chemokines, and immunoglobulins. Subsequently, cytokines produced by dendritic cells, such as IL-12, induce the differentiation of naive T cells into Th1 and cytotoxic T-cells (CTL). Studies have shown that CpG oligodeoxynucleotides as vaccine adjuvants can potentiate immune protection against a variety of viral, bacterial, and parasitic diseases, for example, hepatitis B (Krieg et al., Proc Am Thorac Soc. 4(3):289-94, 2007; Schmidt et al., Nat. Biotechnol. 25(8):825-6, 2007). Thus unmethylated CpG oligodeoxynucleotides can be included as adjuvants in the vaccine compositions disclosed herein to augment both humoral and cell mediated immune responses.

Lipid A, the biologically active portion of the gram-negative bacterial cell wall constituent lipopolysaccharide (LPS), is known to possess strong immunostimulatory properties and has been evaluated as an adjuvant for promoting immune responses. TLR4 was identified as the signaling receptor for lipid A. Monophosphoryl lipid A (MPLA) comprises the lipid A portion of Salmonella minnesota LPS. LPS and MPLA induce similar cytokine profiles, but MPLA is less toxic. Combining MPLA with other immunostimulants can facilitate eliciting an effective immune response.

In specific implementations, the inventive compositions incorporate a ligand for Toll-like receptor (TLR)-9, such as immunostimulatory DNA molecules comprising CpGs, which induce type I interferon secretion, and stimulate T and B cell activation leading to increased antibody production and cytotoxic T cell responses (Krieg et al., CpG motifs in bacterial DNA trigger direct B cell activation. Nature. 1995. 374:546-549; Chu et al. CpG oligodeoxynucleotides act as adjuvants that switch on T helper 1 (Th1) immunity. J. Exp. Med. 1997. 186:1623-1631; Lipford et al. CpG-containing synthetic oligonucleotides promote B and cytotoxic T cell responses to protein antigen: a new class of vaccine adjuvants. Eur. J. Immunol. 1997. 27:2340-2344; Roman et al "Immunostimulatory DNA sequences function as T helper-1-promoting adjuvants," Nat. Med. 1997. 3:849-854; Davis et al. CpG DNA is a potent enhancer of specific immunity in mice immunized with recombinant hepatitis B surface antigen. J. Immunol. 1998. 160:870-876; Lipford et al., "Bacterial DNA as immune cell activator," Trends Microbiol. 1998. 6:496-500; U.S. Pat. No. 6,207,646 to Krieg et al.; U.S. Pat. No. 7,223,398 to Tuck et al.; U.S. Pat. No. 7,250,403 to Van Nest et al.; or U.S. Pat. No. 7,566,703 to Krieg et al.

Dendritic cell targeting molecules can also include monoclonal or polyclonal antibodies or fragments thereof that recognize and bind to epitopes displayed on the surface of dendritic cells. For example, lectin DEC-205, a dendritic cell surface epitope, has been targeted by an anti-DEC205 recombinant antibody in mice, and boosted both humoral and cellular responses to an antigen attached to the heavy chain of the antibody (Hawiger, et al., J. Exp. Med., 194 (6):769-79, 2001; Bonifaz, et al., J. Exp. Med., 196(12): 1627-38, 2002; Bonifaz, et al., J. Exp. Med., 199(6):815-24, 2004). A variety of other endocytic receptors, including a mannose-specific lectin (mannose receptor) and IgG Fc receptors, have also been targeted in this way with similar enhancement of antigen presentation efficiency. Other suitable receptors that can be targeted include, but are not limited to, DC-SIGN, 33D1, SIGLEC-H, DCIR, CD11c, heat shock protein receptors, and scavenger receptors.

Many receptors used for targeting vaccines to dendritic cells, such as lectin DEC-205, have the property of delivering antigens to late endosomes where immunogenic peptides are formed and loaded onto MHC class II molecules (which are needed for CD4 T cell and antibody responses) (Mellman, Adv. Exp. Med. Biol. 560:63-7, 2005; Mellman and Steinman, Cell 106(3):255-8, 2001). Effective vaccination, however, often requires the production of CD8 cytotoxic T cell response, which occurs only when antigen is present in the cytoplasm. Dendritic cells effect this function by cross-presentation, where exogenous antigens escape endocytic vesicles and enter the cytoplasm where they are cleaved into peptides by the proteosome, imported into the endoplasmic reticulum, and loaded onto newly synthesized MHC class I molecules (which are required for stimulation of CD8 T cells). Efficiency of cross presentation can be artificially enhanced by limited disruption of endosome-lysosome membranes during antigen uptake. Endosomal membrane disrupting agents therefore can serve as effective adjuvants, and can include, e.g., small molecule drugs, peptides, polypeptides, including elastin, and synthetic agents that disrupt intracellular pH or vesicular membranes. In certain embodiments, the endosome-disrupting agent is a low pH-activated, amphipathic, pore-forming peptide, e.g., the Endo-Porter peptide (Endo-Porter; GeneTools, Philomath, Oreg.) (Summerton, Ann. N.Y. Acad. Sci., 1058:1-14, 2005). Thus Endo-Porter peptide can be included as adjuvants in the vaccine compositions disclosed herein to augment cross-presentation of pathogenic antigens.

Various adjuvants are described, for example, in PCT WO2012/068295. Such adjuvants can include, but are not limited to, stimulators of pattern recognition receptors, such as RIG-1 and NOD-like receptors (NLR), mineral salts, such as alum, alum combined with monphosphoryl lipid (MPL) A of Enterobacteria, such as Escherichia coli, Salmonella minnesota, Salmonella typhimurium, or Shigella flexneri or specifically with MPL® (AS04), MPL A of above-mentioned bacteria separately, saponins, such as QS-21, Quil-A, ISCOMs, ISCOMATRIX™, emulsions such as MF59™, Montanide® ISA 51 and ISA 720, AS02 (QS21+ squalene+ MPL®), liposomes and liposomal formulations such as AS01, synthesized or specifically prepared microparticles and microcarriers such as bacteria-derived outer membrane vesicles (OMV) of N. gonorrheae, Chlamydia trachomatis, and others, or chitosan particles, depot-forming agents, such as Pluronic® block co-polymers, specifically modified or prepared peptides, such as muramyl dipeptide, aminoalkyl glucosaminide 4-phosphates, such as RC529, or proteins, such as bacterial toxoids or toxin fragments.

In addition to the Toll-Like Receptors noted above, adjuvants can include agonists for pattern recognition receptors (PRR), including, but not limited to Toll-Like Receptors (TLRs), specifically TLRs 2, 3, 4, 5, 7, 8, 9 and/or combinations thereof. In other implementations, adjuvants comprise agonists for Toll-Like Receptors 3, agonists for Toll-Like Receptors 7 and 8, or agonists for Toll-Like Receptor 9; adenine derivatives such as those disclosed in U.S. Pat. No. 6,329,381 (Sumitomo Pharmaceutical Company); immunostimulatory DNA; or immunostimulatory RNA. In specific implementations, the inventive compositions incorporate as adjuvants compounds that are agonists for toll-like receptors (TLRs) 7 & 8 ("TLR 7/8 agonists"). Of utility are the TLR 7/8 agonist compounds disclosed in U.S. Pat. No. 6,696,076 to Tomai et al., including but not limited to, imidazoquinoline amines, imidazopyridine amines, 6,7-fused cycloalkylimidazopyridine amines, and 1,2-bridged imidazoquinoline amines.

In specific implementations, an adjuvant can be an agonist for the surface molecule CD40. In certain implementations, to stimulate immunity rather than tolerance, an inventive composition incorporates an adjuvant that promotes DC maturation (needed for priming of naive T cells) and the production of cytokines, such as type I interferons, which promote antibody immune responses. In implementations, adjuvants can also include immunostimulatory RNA molecules, such as, but not limited to, dsRNA or poly I:C (a TLR3 stimulant), and/or those disclosed in F. Heil et al., "Species-Specific Recognition of Single-Stranded RNA via Toll-like Receptor 7 and 8" Science 303(5663), 1526-1529 (2004); J. Vollmer et al., "Immune modulation by chemically modified ribonucleosides and oligoribonucleotides" WO 2008033432 A2; A. Forsbach et al., "Immunostimulatory oligoribonucleotides containing specific sequence motif(s) and targeting the Toll-like receptor 8 pathway" WO 2007062107 A2; E. Uhlmann et al., "Modified oligoribonucleotide analogs with enhanced immunostimulatory activity" U.S. Pat. Appl. Publ. US 2006/0241076; G. Lipford et al., "Immunostimulatory viral RNA oligonucleotides and use for treating cancer and infections" WO 2005097993 A2; G. Lipford et al., "Immunostimulatory G,U-containing oligoribonucleotides, compositions, and screening methods" WO 2003086280 A2. In some implementations, an adjuvant can be a TLR-4 agonist, such as bacterial lipopolysaccharide (LPS), VSV-G, and/or HMGB-1. In some implementations, adjuvants can comprise TLR-5 agonists, such as flagellin, or portions or derivatives thereof, including but not limited to those disclosed in U.S. Pat. Nos. 6,130,082, 6,585,980, and 7,192,725.

In some implementations, adjuvants can be proinflammatory stimuli released from necrotic cells (e.g., urate crystals). In some implementations, adjuvants can be activated components of the complement cascade (e.g., CD21, CD35, etc.). In some implementations, adjuvants can be activated components of immune complexes. The adjuvants can also include complement receptor agonists, such as a molecule that binds to CD21 or CD35. In some implementations, the complement receptor agonist induces endogenous complement opsonization of the synthetic nanoparticle. In some implementations, adjuvants are cytokines, which are small proteins or biological factors (in the range of 5 kD-20 kD) that are released by cells and have specific effects on cell-cell interaction, communication and behavior of other cells. In some implementations, the cytokine receptor agonist is a small molecule, antibody, fusion protein, or aptamer.

In various implementations, at least a portion of the dose of adjuvant can be coupled to synthetic nanoparticles, e.g., all of the dose of adjuvant can be coupled to synthetic nanoparticles. In other implementations, at least a portion of the dose of the adjuvant is not coupled to the synthetic nanoparticles. In certain implementations, the dose of adjuvant comprises two or more types of adjuvants. For instance, and without limitation, adjuvants that act on different TLR receptors can be combined. As an example, in an implementation a TLR 7/8 agonist can be combined with a TLR 9 agonist. In another implementation, a TLR 7/8 agonist can be combined with a TLR 4 agonist. In yet another implementation, a TLR 9 agonist can be combined with a TLR 3 agonist.

In some other embodiments, the adjuvant can include one or more of the following: glycolipid alpha-galactosylceramide; oil emulsions (e.g., Freund's adjuvant); saponin formulations; virosomes and viral-like particles; bacterial and microbial derivatives including, but not limited to carbohydrates such as lipopolysaccharide (LPS); immunostimulatory oligonucleotides; ADP-ribosylating toxins and detoxified derivatives; alum; BCG; mineral-containing compositions (e.g., mineral salts, such as aluminum salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants can also include immunomodulators such as cytokines, interleukins (e.g., IL-1, IL-2, IL-4, IL-5, IL-6, IL-7, IL-12, etc.), interferons (e.g., interferon-γ), macrophage colony stimulating factor, and tumor necrosis factor; and co-stimulatory molecules, such as those of the B7 family.

Methods for Assembling Adjuvant-Loaded Nanoparticles

Many known processes can be used to form the adjuvant-loaded nanoparticles. For example, adjuvant-loaded nanoparticles can be formed by solvent evaporation techniques (as described in Mathiowitz, et al., J. Scanning Microscopy 4:329, 1990; Beck et al., Fertil. Steril. 31:545, 1979; Benita, et al., J. Pharm. Sci., 73:1721, 1984; and U.S. Pat. No. 3,960,757). The one or more polymers are dissolved in a volatile organic solvent, such as methylene chloride. Adjuvants can be added to the solution, and the mixture is suspended in an aqueous solution that contains a surface active agent such as poly(vinyl alcohol). The resulting emulsion is stirred until most of the organic solvent is evaporated, leaving solid nanoparticles.

In other examples, adjuvant-loaded nanoparticles can be formed by using phase inversion wherein a polymer is dissolved in a solvent, fine particles of the adjuvant are mixed or dissolved in the polymer solution, and the mixture is poured into a strong non-solvent for the polymer, to spontaneously produce, under favorable conditions, polymeric microspheres, wherein the polymer is either coated with the particles or the particles are dispersed in the polymer.

Certain adjuvants can be coupled non-covalently to the nanoparticles, such as by adsorption. For example, adsorption of nucleic acids to the surface of a nanoparticle can be accomplished by salt formation. When using this method, the nanoparticle is prepared in such a manner that the nanoparticle comprises a material that introduces a charge to the nanoparticle. Often the use of a charged surfactant, e.g., a cationic surfactant that is used to adsorb the negatively charged nucleic acids during the nanoparticle preparation, is sufficient to provide surface charge to the nanoparticle. Contacting the charged nanoparticles with a solution of nucleic acids causes adsorption of the nucleic acids. This method is described in the patent application in Published International Patent Application WO 00/06123 of O'Hagen et al.

Some adjuvants can be encapsulated by the nanoparticles. For example, encapsulation of nucleic acids, such as unmethylated CpG oligodeoxynucleotides, can be accomplished by dissolving the nucleic acids in an aqueous buffer and then using this solution in the single or double emulsion process to form nanoparticles by self-assembly. This process is described in Tse, et al *International Journal of Pharmaceutics,* 370 (1-2), 33 (2009). In addition, various materials can be encapsulated into synthetic nanoparticles using a variety of methods including but not limited to C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly (Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006).

Other methods suitable for encapsulating materials, such as nucleic acids, into synthetic nanoparticles can be used, including without limitation methods disclosed in U.S. Pat. No. 6,632,671 to Unger issued Oct. 14, 2003; H. Martimprey et al., "Polymer nanocarriers for the delivery of small fragments of nucleic acids: Oligonucleotides and siRNA" European Journal of Pharmaceutics and Biopharmaceutics 71:490-504 (2009); or P. Malyala, et al., "Enhancing the therapeutic efficacy of CpG oligonucleotides using biodegradable microparticles" Advanced Drug Delivery Reviews 61: 218-225 (2009).

Covalent coupling can be accomplished by a variety of methods, e.g., as described in *Bioconjugate Techniques, 2$^{nd}$* edition, Elsevier (2008) by Hermanson. One method that is useful for coupling nucleic acids to polymers or nanoparticles carrying amine functional groups is to activate the 5' phosphate of the nucleic acid with 1-(3-dimethylamino) propyl-3-ethylcarbodiimide methiodide (EDC) and imidazole and then reacting the activated nucleic acid with the amine substituted polymer or nanoparticle (Shabarova et al, *FEBS Letters,* 154 288, (1983)). A schematic of this process is shown below for surface amine functionalized nanoparticles.

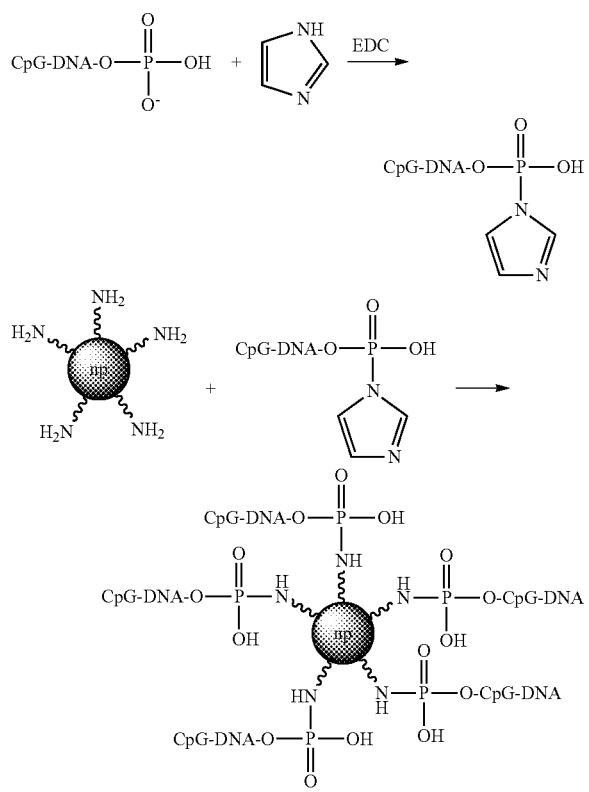

In certain embodiments, covalent coupling can be made via a covalent linker. For example, the covalent linker can be or comprise an amide linker, a disulfide linker, a thioether linker, a hydrazone linker, a hydrazide linker, an imine or oxime linker, a urea or thiourea linker, an amidine linker, an amine linker, and a sulfonamide linker.

An amide linker is formed via an amide bond between an amine on one element with the carboxylic acid group of a second element such as the nanoparticle. The amide bond in the linker can be made using any of the conventional amide bond forming reactions with suitably protected amino acids or antigens or adjuvants and activated carboxylic acid such N-hydroxysuccinimide-activated ester.

A disulfide linker is made via the formation of a disulfide (S—S) bond between two sulfur atoms of the form, for instance, of $R_1$—S—S—$R_2$. A disulfide bond can be formed by thiol exchange of an antigen or adjuvant containing thiol/mercaptan group (—SH) with another activated thiol group on an element containing thiol/mercaptan groups with an element containing an activated thiol group.

A triazole linker, e.g., a 1,2,3-triazole of the form

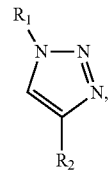

wherein $R_1$ and $R_2$ can be any chemical entities, can be made by the 1,3-dipolar cycloaddition reaction of an azide attached to a first element with a terminal alkyne attached to a second element. The 1,3-dipolar cycloaddition reaction is performed with or without a catalyst, preferably with Cu(I)-catalyst, which links the two elements through a 1,2,3-triazole function. This chemistry is described in Sharpless et al., Angew. Chem. Int. Ed. 41(14), 2596, (2002) and Meldal, et al, Chem. Rev., 2008, 108(8), 2952-3015 and is often referred to as a "click reaction" or CuAAC.

A thioether linker is made by the formation of a sulfur-carbon (thioether) bond in the form, for instance, of $R_1$—S—$R_2$. Thioether can be made by either alkylation of a thiol/mercaptan (—SH) group on one component such as the element with an alkylating group such as halide or epoxide on a second element. Thioether linkers can also be formed by Michael addition of a thiol/mercaptan group on one element to an electron-deficient alkene group on a second element such as a polymer containing a maleimide group as the Michael acceptor. In another way, thioether linkers can be prepared by the radical thiol-ene reaction of a thiol/mercaptan group on one element with an alkene group on a second element such as a polymer or nanoparticle.

A hydrazone linker is made by the reaction of a hydrazide group on one element with an aldehyde/ketone group on the second element.

A hydrazide linker is formed by the reaction of a hydrazine group on one element with a carboxylic acid group on the second element. Such reaction is generally performed using chemistry similar to the formation of amide bond where the carboxylic acid is activated with an activating reagent.

An imine or oxime linker is formed by the reaction of an amine or N-alkoxyamine (or aminooxy) group on one element with an aldehyde or ketone group on a second element.

A urea or thiourea linker is prepared by the reaction of an amine group on one element with an isocyanate or thioisocyanate group on a second element.

An amidine linker is prepared by the reaction of an amine group on one element with an imidoester group on a second element.

An amine linker is made by the alkylation reaction of an amine group on one element with an alkylating group such as halide, epoxide, or sulfonate ester group on the second element. Alternatively, an amine linker can also be made by reductive amination of an amine group on one element with an aldehyde or ketone group on the second element with a suitable reducing reagent such as sodium cyanoborohydride or sodium triacetoxyborohydride.

A sulfonamide linker is made by the reaction of an amine group on one element with a sulfonyl halide (such as sulfonyl chloride) group on a second element.

Various adjuvants can also be coupled via non-covalent coupling methods. For examples, a negative charged adjuvant can be coupled to a positively charged carrier through electrostatic adsorption. An adjuvant containing a metal ligand can also be coupled to a carrier containing a metal complex via a metal-ligand complex.

In certain embodiments, adjuvants can be attached to a polymer, for example polylactic acid-block-polyethylene glycol, prior to the assembly of a synthetic nanoparticle or a synthetic nanoparticle can be formed with reactive or activatable groups on its surface. In the latter case, the adjuvant can be prepared with a group that is compatible with the attachment chemistry that is presented by the synthetic nanoparticles' surface. In other implementations, a peptide adjuvant can be attached to virus-like particles (VLPs) or liposomes using a suitable linker.

In certain embodiments, the linker can be a homobifunctional or heterobifunctional reagent as described in Hermanson 2008. For example, a VLP or liposome synthetic nanoparticle containing a carboxylic group on the surface can be treated with a homobifunctional linker, adipic dihydrazide (ADH), in the presence of EDC to form the corresponding synthetic nanoparticle with the ADH linker. The resulting ADH linked synthetic nanoparticle is then conjugated with a peptide antigen containing an acid group via the other end of the ADH linker on NC to produce the corresponding VLP or liposome peptide conjugate.

Attachment Mechanisms

One or more adjuvant-loaded nanoparticles can be attached to each inactivated pathogen through a variety of attachment mechanisms including, but not limited to, electrostatic attractions, covalent coupling directly or through a linker, or hydrophobic interactions.

In some embodiments, the inactivated pathogens are attached to adjuvant-loaded nanoparticles through electrostatic attractions. Most protozoans, bacteria, and viruses have a negative surface charge at physiologic pH (Robert A. Freitas Jr., Nanomedicine, Volume IIA: Biocompatibility, Landes Bioscience, Georgetown, T X, 2003). For example, Gram-negative bacteria have an outer membrane composed of lipopolysaccharides, which impart a strongly negative charge to their surface. Almost all Gram-positive bacteria cell walls are made up of thick peptidoglycan layer, which is rich in negatively charged Teichoic acids (Knox, et al., Bacteriol. Rev. 37(2):215, 1973). Cationic nanoparticles can be used to effectively target those negatively charged pathogens through electrostatic attractions (Liu et al., Nature Nanotechnology 4, 457-463, 2009).

In some embodiments, nanoparticles formed by PLGA-PLH-PEG have sufficiently strong cationic charges on their surface that they can bind to negatively charged inactivated pathogen through electrostatic attractions.

In some embodiments, the inactivated pathogens can be attached to adjuvant-loaded nanoparticles through a linker conjugated on the nanoparticle surface. The linker can be a monoclonal antibody that binds specifically to a surface antigen of the inactivated pathogen, e.g. monoclonal antibody that targets *E. coli* 0157 surface antigen (Zhao et al., Proc Natl Acad Sci USA. 101(42):15027-32, 2004). The linker can be an aptamer that binds specifically to a surface target of the inactivated pathogen, e.g., aptamer NK2 that binds to virulent strain *M. tuberculosis* (H37Rv) with high affinity and specificity (Chen et al., Biochem Biophys Res Commun. 8; 357(3):743-8, 2007). The linker can be an antibiotic, e.g., vancomycin, which binds specifically to a surface target of the inactivated pathogen (Kell et al., ACS Nano 2: 1777-1788, 2008). The linker can be a lectin that binds specifically to a surface polysaccharide of the inactivated pathogen, e.g., Ulex Europaeus Agglutinin I (UEA I) or Conconavalin A (Con A) lectins that binds to carbohydrate receptors of *H. pylori* strains (Umamaheshwari et al., J Drug Target. 11(7):415-23, 2003). The linker can also be an antimicrobial peptide, e.g., Sushi 1, which binds specifically to a surface target of the inactivated pathogen (Leptihn et al., BMC Biol 7: 22, 2009). Other linkers described herein can also be used.

In some embodiments, the inactivated pathogens attach to adjuvant-loaded nanoparticles through a pair of binding partners that form highly specific, non-covalent interactions with each another. Suitable binding pairs are well known in the art, for example, biotin and avidin, biotin and streptavidin, biotin and neutravidin, glutathione-S-transferase and glutathione, maltose-binding protein and amylase, and maltose-binding protein and maltose.

Methods of Using the Vaccine Compositions

The vaccine compositions disclosed herein are useful as prophylactic vaccines, which confer immune protection in a subject against subsequent infection by the specific pathogens contained in the vaccine. For example, the pathogen can be bacterium, such as a *Chlamydia trachomatis, Francisella tularensis, Mycobacterium tuberculosis, Streptococcus pneumoniae, Listeria monocytogenes, Vibrio cholera, Shigella sonnei, Shigella flexneri*, or *Salmonella typhimurium*; or a virus, such as an Influenza virus, human immunodeficiency virus (HIV), Hepatitis C virus. Subjects at a risk of developing disease from an infectious pathogen can be treated prophylactically with the vaccine compositions disclosed herein. An individual traveling to or living in an area of endemic infectious disease may be considered to be at risk and a candidate for prophylactic vaccination against the particular infectious pathogen. Preventative treatment can be applied to any number of pathogen-related diseases where there is a known relationship between the particular disease and a particular risk factor, such as geographical location or work environment.

The vaccine compositions are also useful as therapeutic vaccines, which can be used to initiate or enhance a subject's immune response to a contracted pathogen. Subjects having contracted an infectious pathogen can be treated therapeutically with the vaccine compositions disclosed herein.

The ability of these vaccine compositions to elicit T-cell mediated mucosal immune responses makes these compositions especially useful for preventing and treating infectious diseases caused by bacteria, viruses, parasites, fungi, or other microbial pathogens that enter a subject through the mucosal membranes.

The desired outcome of a prophylactic or therapeutic immune response may vary according to the disease, according to principles well known in the art. For example, an immune response against a pathogen may inhibit or prevent colonization and replication of the pathogen, effecting protective immunity and the absence or reduction of any disease symptoms. However, a vaccine against pathogens may be considered effective if it reduces the number, severity, or duration of symptoms; if it reduces the number of individuals in a population with symptoms; or even if it merely reduces the transmission of an infectious pathogen. Treatment may be effected in a single dose or repeated at intervals. The appropriate dosage depends on various parameters understood by skilled artisans such as the vaccine composition itself, the route of administration or the condition of the subject to be vaccinated (weight, age and the like).

Administration In general, vaccines can be administered by a variety of routes including, but not limited to: oral, inhalation (nasal, bronchial, or pulmonary), intravenous, intraperitoneal, intramuscular, transdermal, subcutaneous, topical, sublingual, vaginal, or rectal means.

The vaccine compositions and methods of preventing or treating infections disclosed herein are particularly effective through mucosal administration to the oral/alimentary, respiratory, or genitourinary tracts. For example, the vaccine compositions can be administered through an ocular, intranasal, oral, buccal, sublingual, tonsilar, bronchial, pulmonary, gastric, intestinal, rectal, vaginal, or urinary tract route. In some embodiments, the vaccine compositions can be administered by intranasal vaccination. Methods of intranasal vaccination include administration of a droplet, spray, or dry powdered form of the vaccine, e.g., nebulized or aerosolized vaccine composition, into the nasopharynx of the individual to be immunized. Alternative administration routes include intravaginal and intrarectal administration, and suppositories for rectal or vaginal administration can be utilized. The vaccine compositions can be administered by the vaginal route, and pharmaceutically acceptable excipients for vaginal administration can be used, including emulsifiers, polymers such as CARBOPOL®, and other known stabilizers of vaginal creams and suppositories. The vaccine compositions can be administered by the rectal route, and waxes and polymers known in the art for forming rectal suppositories can be included. In some embodiments, the vaccine composition can be administered orally or through other gastrointestinal route. Enteric formulations such as gastro resistant capsules and granules for oral administration are suitable for such administration.

Targeting the vaccine compositions directly to mucosal membranes greatly facilitates the ability of the vaccine compositions to induce mucosal immunity. Mucosal immunity is essential for protection against infections by pathogens before they cross the mucosal barrier. Moreover, mucosal vaccination through one route, such as intranasal vaccination, may induce mucosal immunity not only in that mucosal site, but also in distant mucosal sites such as the genital mucosa (Mestecky, Journal of Clinical Immunology, 7:265-276, 1987). Besides its superiority in inducing mucosal immune responses, another attractive advantage of the mucosal vaccination relies on its ability to also induce good systemic immunity. Mucosal administration also bypasses the painful injections and the associated negative effect on patients, especially when boosts are required to sustain a vigorous immunity.

Administration of the vaccine compositions can be accomplished by any acceptable method that allows an effective amount of the vaccine to reach its target. Penetrants appropriate for mucosal administration can be included in the vaccine compositions, for example, detergents, bile salts, or fusidic acid derivatives. The particular mode selected will depend upon factors such as the particular composition, the severity of the state of the subject being treated, and the dosage required to induce an effective immune response in the subject. As generally used herein, an "effective amount" is the amount that is sufficient to induce an immune response in the treated subject. The actual effective amounts of vaccine can vary according to the specific pathogen and adjuvant being utilized, the particular vaccine composition formulated, the mode of administration, and the age, weight, condition of the individual being vaccinated, as well as the route of administration and the disease or disorder.

EXAMPLES

The invention is further described in the following examples, which do not limit the scope of the invention described in the claims.

Example 1. Immunization with Inactivated *Chlamydia trachomatis* Induces Regulatory T Cell-Mediated Immune Tolerance Bacteria of the genus *Chlamydia* cause a plethora of ocular, genital and respiratory diseases, such as conjunctivitis and blinding trachoma, non-gonococcal urethritis, cervicitis, pelvic inflammatory disease, ectopic pregnancy, tubal factor infertility, and interstitial pneumonia (Igietseme et al., Expert Review of Vaccines 10:1585-1596, 2011). *Chlamydia trachomatis* (thereafter "*Chlamydia*" or "Ct") is an obligate intracellular pathogen that alternates in its life cycle between an infectious elementary body (EB) and a metabolically active reticulate body (RB). Currently there are no vaccines available for use in humans against *Chlamydia trachomatis* infection (Igietseme et al., Expert Review of Vaccines 10:1585-1596, 2011).

A vaccine based on inactivated *Chlamydia* was first examined for its immune protective effect. Live pathogenic *Chlamydia* elementary bodies were inactivated by exposure to UV light for 30 minutes. The inactivated *Chlamydia* bacteria were isolated by infecting McCoy cells to exclude actively proliferating *Chlamydia*.

Mice were intrauterinely immunized with infectious or UV-inactivated *Chlamydia*. Intrauterine inoculation was performed using the Non-Surgical Embryo Transfer Device (NSET, ParaTechs) following the accompanying instructions. Mice were briefly restrained while a single small plastic "speculum" was inserted into the vagina. This allowed a special micropipette tip (on a regular pipette) to be positioned for precise delivery of 10-20 μl of the *Chlamydia* bacteria across the cervix.

Four weeks after immunization, the immunized mice and naïve control mice were challenged intrauterinely with $10^6$ Infectious Unit (IFU) of live *Chlamydia*. Six days later, uteri were harvested from all challenged mice and RNA samples were prepared from uteri. Quantitative PCR (qPCR) was performed to detect and determine the amount of *Chlamydia* 16s RNA relative to the amount of mouse glyceraldehyde-3-phosphate dehydrogenase (GAPDH). Normalized amount of *Chlamydia* 16s rRNA was calculated for each mouse of four independent experiments and presented as *Chlamydia* load in FIG. 1A. Intrauterine immunization with infectious *Chlamydia* resulted in reduced *Chlamydia* load and immune protection against subsequent intrauterine challenge by live *Chlamydia* (FIG. 1A). Intrauterine immunization with UV-inactivated *Chlamydia* (UV-Ct), however, resulted in enhanced susceptibility to subsequent live *Chlamydia* challenge, indicating immune tolerance had been induced by UV-inactivated *Chlamydia* (FIG. 1A). This suggests inactivated bacteria alone do not induce protection, but rather immune tolerance.

Figure 1B:
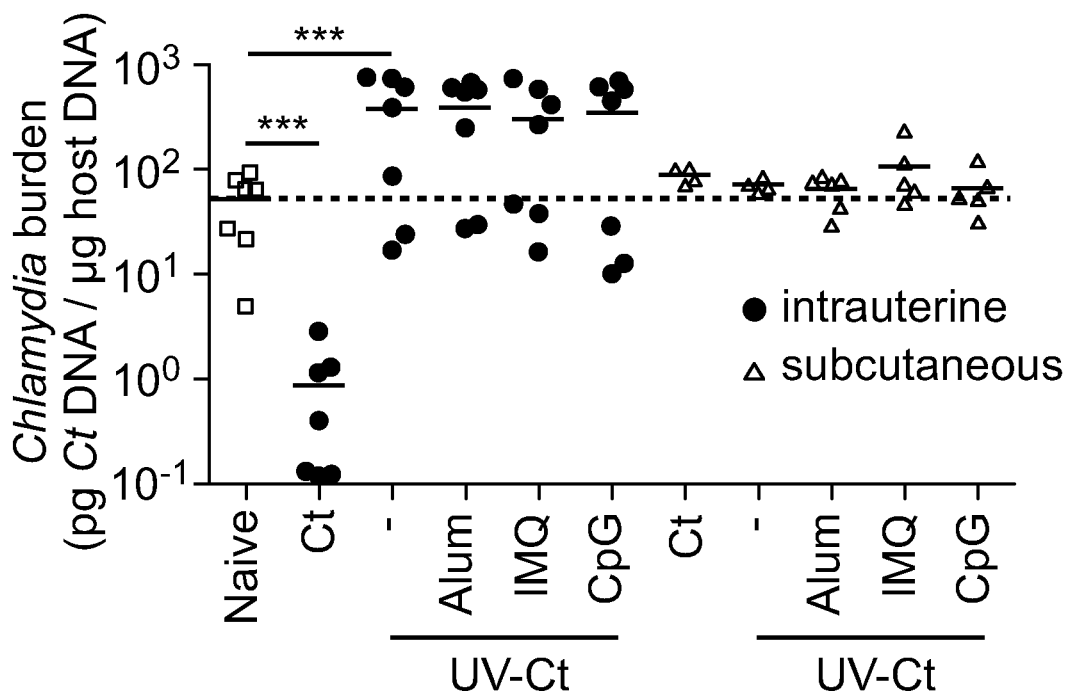
FIG. 1B is a dot plot showing that co-administration of adjuvants does not overcome UV-Ct induced immune tolerance.

Next, different types of adjuvants were co-administered with UV-inactivated *Chlamydia* to see if they can overcome the immune tolerance induced by the inactivated *Chlamydia*. Mice were intrauterinely immunized with infectious *Chlamydia*, UV-inactivated *Chlamydia*, or UV-inactivated *Chlamydia* with one of the following adjuvants: aluminum hydroxide (Alum); imiquimod (IMQ); or CpG oligodeoxynucleotide type C (CpG). Four weeks after immunization, the immunized mice and naïve controls mice were challenged either intrauterinely or subcutaneously with live *Chlamydia* as described above. *Chlamydia* loads were measured by qPCR on Day 6 after the challenge, and data from a representative experiment were shown in FIG. 1B. Intrauterine immunization with UV-inactivated *Chlamydia* again resulted in immune tolerance and co-administration of adjuvants does not overcome the immune tolerance effect (FIG. 1B). Subcutaneous immunization with UV-inactivated *Chlamydia* did not provide protection or tolerance for subsequent genital *Chlamydia* challenge even when co-administered with Alum, IMQ, or CpG (FIG. 1B).

The specific T cell type mediating the immune tolerance was investigated by using *Chlamydia*-specific TCR transgenic mice. Wild-type $CD90.1^+$ transgenic $CD4^+$ T cells (NR1 cells) were transferred into $CD90.2^+$ host mice. One day later, the recipient mice were inoculated intrauterinely with $10^6$ IFU of infectious or UV-inactivated *Chlamydia*. At Day 4 following the infection, draining lymph nodes were harvested and cells were prepared for flow cytometry. The transferred $CD90.1^+$ $CD4^+$ T cells were analyzed for intracellular FoxP3 expression, which is a marker for regulatory T (Treg) cells. A significant increase of FoxP3-expressing $CD25^{hi}$ NR1 cells was observed in the uterus and the draining LN following UV-Ct immunization (FIGS. 1C-1D). These $FoxP3^+$ cells were generated by conversion rather than proliferation because transfer of $eGFP^-$ NR1 cells, isolated by FACS, yielded similar numbers of Tregs (FIGS. 1C-1D). These data suggest that UV-Ct immunization leads to the induction of $FoxP3^+$ Tregs and may explain why this vaccine approach is ineffective and induces immune tolerance.

CD25 is an established marker for $CD4^+$ $FoxP3^+$ Treg cells in mice. To determine if Tregs were responsible for tolerance, Treg cells were depleted by anti-CD25 monoclonal antibody treatments three days before and after *Chlamydia* challenge in mice previously vaccinated with UV-Ct. *Chlamydia* load was examined as described above. Specifically, mice were intrauterinely immunized with $10^6$ IFU of UV-inactivated *Chlamydia*. Four weeks later, immunized mice and naïve controls mice were challenged with $10^6$ IFU of infectious *Chlamydia*. Three days before the challenge and three days after the challenge, the immunized mice were treated with an anti-CD25 monoclonal antibody (PC61.5) or control IgG (500 mg). *Chlamydia* loads were measured by qPCR on Day 6 after the challenge. Depletion of Tregs reduced the *Chlamydia* levels in the genital tract relative to control IgG-treated mice (FIG. 1E), indicating that $CD4^+$ $FoxP3^+$ Treg cells play a critical role in mediating the inactivated *Chlamydia* induced immune tolerance.

When activated, Treg cells secrete large amounts of interleukin-10 (IL-10). Therefore, the role of IL-10 in in the inactivated *Chlamydia* induced immune tolerance was examined. Wild type or IL-10-/- mice were immunized intrauterinely with infectious or UV-inactivated *Chlamydia*. Challenged with live *Chlamydia* and determination of *Chlamydia* loads were performed as described above. IL-10 deficiency abrogated the inactivated *Chlamydia* induced immune tolerance (FIG. 1F), confirming that Treg-secreted IL-10 plays a critical role in the inactivated *Chlamydia* induced immune tolerance.

These results indicate that UV-Ct vaccination stimulates tolerance through the induction of *Chlamydia*-specific $CD4^+$ Tregs in an IL-10-dependent fashion.

Figure 2A:
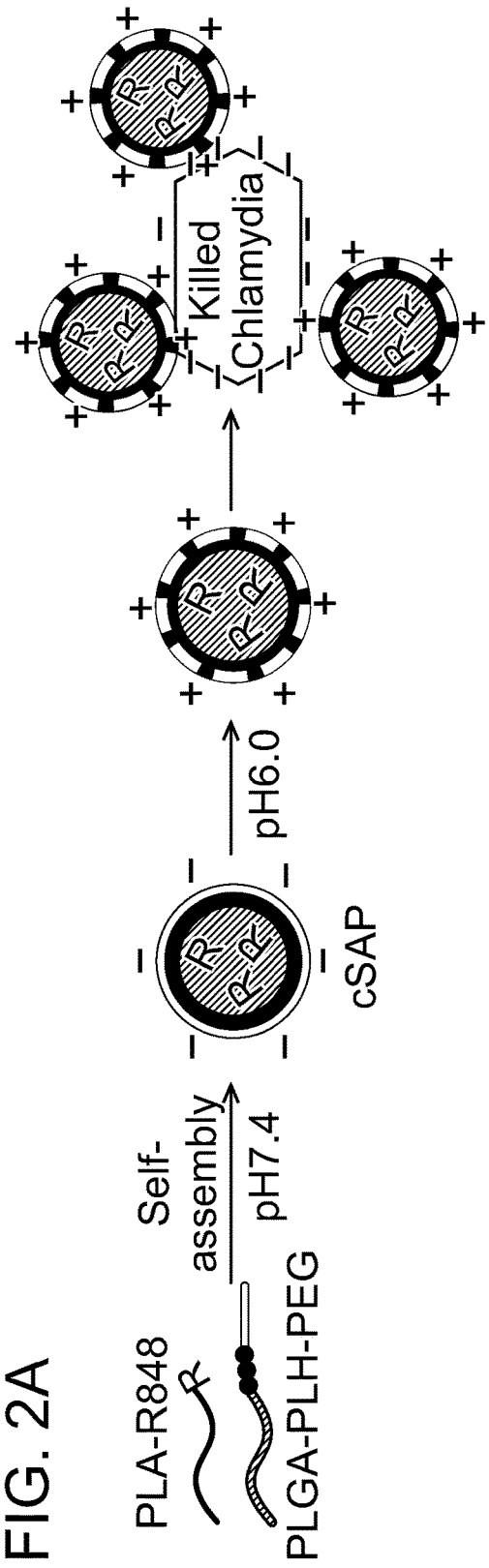
FIG. 2A is a schematic drawing illustrating that the surface charge-switching synthetic adjuvant particles (cSAP) bind to inactivated *Chlamydia trachomatis*.

Example 2. Generation and Evaluation of *Chlamydia trachomatis* Vaccine Compositions Vaccine compositions including UV-inactivated *Chlamydia* attached to adjuvant-loaded polymeric nanoparticles were prepared and evaluated. The TLR7 agonist R848 was used as an example of the suitable adjuvants that can be included in the vaccine composition. R848 was covalently linked to PLA, and assembled into nanoparticles that were slightly negatively charged and surface PEGylated at physiologic pH 7.4. Lowering the pH to 6 activates the surface-switching mechanism, resulting in positive surface charges of the nanoparticles and subsequent binding to negatively charged *Chlamydia* (FIG. 2A).

Polymer Synthesis

Poly(L-histidine) (PLH) was custom synthesized by GenScript (Piscataway, N.J.) to contain an N-terminal lysine and C-terminal cysteine with 20 histidine residues in between (N- to C-terminus sequence: $KH_{20}C$). This $KH_{20}C$ peptide (0.01 mmol) was mixed with 0.01 mmol orthopyridyl-modified methoxy poly(ethylene glycol) (mPEG-OPSS, purchased from Laysan Bio, Arab, Ala.) in water to generate PLH-PEG diblock copolymer, which was purified by dialysis using Slide-A-Lyzer 2,000 MWCO dialysis cassettes (Thermo Scientific) and lyophilized to dry product.

Separately, 5 µmol poly(lactic-co-glycolic acid)-COOH (PLGA-COOH) with an inherent viscosity of 0.67 (purchased from LACTEL Absorbables) was activated by 0.246 mmol 1-ethyl-3-(3-dimethylaminopropyl)carbodiimide (EDC) and 0.295 mmol N-Hydroxysuccinimide (NHS) in 2 mL dichloromethane. PLGA-NHS was precipitated by $-20°$ C. methanol, and dried in a vacuum at 50° C. Dried PLGA-NHS (104.9 mg) was then coupled to 24.8 mg PLH-PEG diblock copolymer (synthesized as described above) by reaction for at least 24 hours in DMSO to generate a PLGA-PLH-PEG triblock copolymer. The PLGA-PEG diblock copolymer was purchased from Boehringer Ingelheim GmbH.

The R848-PLA (polylactic acid) was synthesized by ring opening polymerization. R-848, (100 mg, $3.18 \times 10^{-4}$ moles, from InVivogen), D/L lactide (5.6 gm, $3.89 \times 10^{-2}$ moles, from Sigma Aldrich) and anhydrous sodium sulfate (4.0 gm) were dried under vacuum at 50° C. for 8 hours and subsequently toluene (100 mL) was added. The reaction was stirred in an oil bath set at 120° C. and then tin ethylhexanoate (75 mg, 60 µL) was added. Heating was then continued under argon for 16 hours. The reaction was stopped by adding water and subsequently with additional toluene (200 mL). The toluene solution was then washed in turn with 10% sodium chloride solution containing 5% hydrochloric acid (200 mL) followed by saturated sodium bicarbonate (200 mL). The solution was dried over magnesium sulfate, filtered and evaporated under vacuum to give 3.59 grams of polylactic acid-R-848 conjugate. A portion of the polymer was hydrolyzed in base and examined by HPLC for R-848 content. By comparison to a standard curve of R-848 concentration with the HPLC response, it was determined that the polymer contained 5.6 mg of R-848 per gram of polymer. The molecular weight of the polymer was determined by GPC to be about 27,000 (see US Patent Application Publication No. 20110268805).

R848-Loaded Polymeric Nanoparticle Preparation

R848-loaded nanoparticles were prepared by emulsifying a polymer-containing organic phase into an aqueous phase, as previously described (Kamaly et al., Chem. Soc. Rev., 41: 2971-3010, 2012). The organic phase was prepared by mixing the following three polymers: (1) poly(lactic-coglycolic acid)-block-poly(L-histidine)-block-poly(ethylene glycol) (PLGA-PLH-PEG) triblock co-polymers (40 wt %), (2) PLGA-PEG diblock copolymers (20 wt %), and (3) poly(lactic acid)-R848 conjugates (PLA-R848) (40 wt %). The PLGA-PEG copolymers were added to improve stability of the organic phase. Forming conjugates of active ingredients with biodegradable polymers improves encapsulation and controls the release of active ingredients from PLGA- or PLA-based nanoparticles (Kolishetti et al., Proc. Natl. Acad. Sci. USA., 107:17939-17944, 2010).

Vaccine Formulation

In a typical formulation, nanoparticles designed to attach to *Chlamydia* bacteria were prepared by mixing 5.33 mg of PLH-containing polymer with 2.66 mg of PLGA-PEG and 5.33 mg of R848-PLA conjugate together in 400 µL of a 15/85 DMSO/ethyl acetate solution. Control nanoparticles that were not positively charged were formulated in a similar manner, only using 8.0 mg of PLGA-PEG and 5.33 mg of R848-PLA. For nanoparticles that did not contain R848-PLA, an equal amount of PLGA was used (inherent viscosity of 0.67, LACTEL absorbables). The polymer-containing organic solution was sonicated into 2 mL of pure water using a probe tip sonicator (Misonix Sonicator S-4000, Farmingdale, N.Y.) for 30 second in continuous mode at 40% amplitude, and then diluted into 8 mL of pure water under magnetic stirring in a fume hood. The solvent was allowed to evaporate for at least 2 hours, at which point the nanoparticles were collected and purified by repeated ultrafiltration using Amicon Ultra-4 100,000 NMWL cutoff filters (Millipore, Billerica, Mass.).

The polymeric nanoparticles (40 wt % PLGA-PLH-PEG, 40 wt % PLA-R848, 20 wt % PLGA-PEG) (0.67 mg/dose) were incubated with 107 IFU per dose of UV-inactivated *Chlamydia* in a dilute salt solution at pH 6.0. At this pH, the nanoparticles yield a positive surface charge (zeta potential 20.7±1.0 mV) and can bind to the surface of the negatively charged UV-inactivated bacteria (zeta potential −12.9±0.6 mV), forming the desired *Chlamydia*-nanoparticle conjugates (FIG. 2A). As a control formulation, a formulation containing: (1) PLGA-PEG (60 wt %) and (2) PLA-R848 conjugate (40 wt %), was prepared and processed with the same steps as above.

Figure 2B:
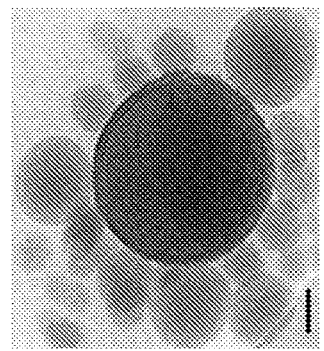
FIG. 2B is a cryo-TEM (cryogenic transmission electron microscope) image showing the binding of R848-loaded nanoparticles to the surface of inactivated *Chlamydia trachomatis*.
Figure 2C:
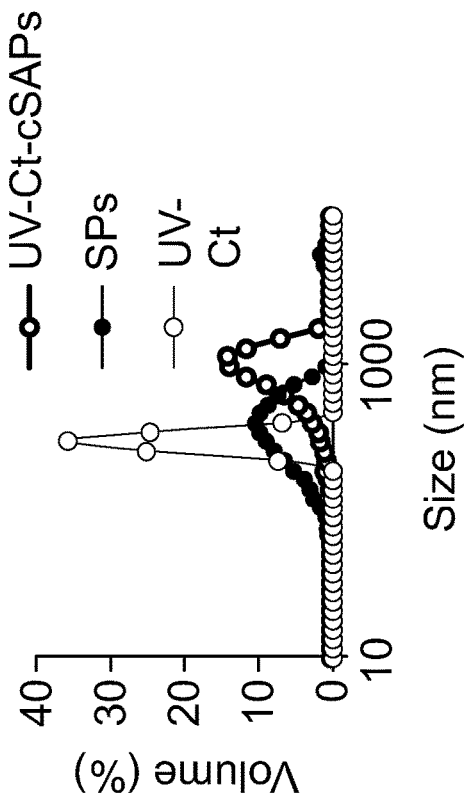
FIG. 2C is a dynamic light scattering graph confirming the binding of nanoparticles to inactivated *Chlamydia trachomatis*.

The binding of R848-loaded nanoparticles (also called "charge-switching synthetic adjuvant particles" (cSAPs)) to inactivated *Chlamydia* was examined by atomic force microscopy. FIG. 2B is a cryo-TEM (cryogenic transmission electron microscope) image showing the binding of R848-loaded nanoparticles to the surface of inactivated *Chlamydia trachomatis* in low pH conditions, e.g., at pH 6. Dynamic light scattering confirms the binding of R848-loaded nanoparticles to inactivated *Chlamydia* bacteria by revealing size differences of UV-Ct-cSAP constructs compared to UV-Ct or cSAPs alone (FIG. 2C).

Figure 2E:
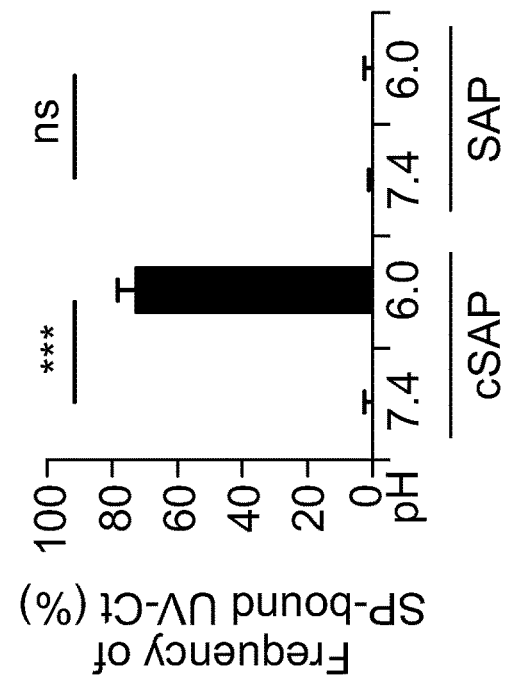
FIGS. 2D-2E are a set of flow cytometry graphs and corresponding histograms showing the binding of BacLight-stained UV-Ct with either Alexa Fluor 488-labeled cSAP or control particles lacking the PLH group (SAP) at pH of 7.4 and 6.0
Figure 2D:
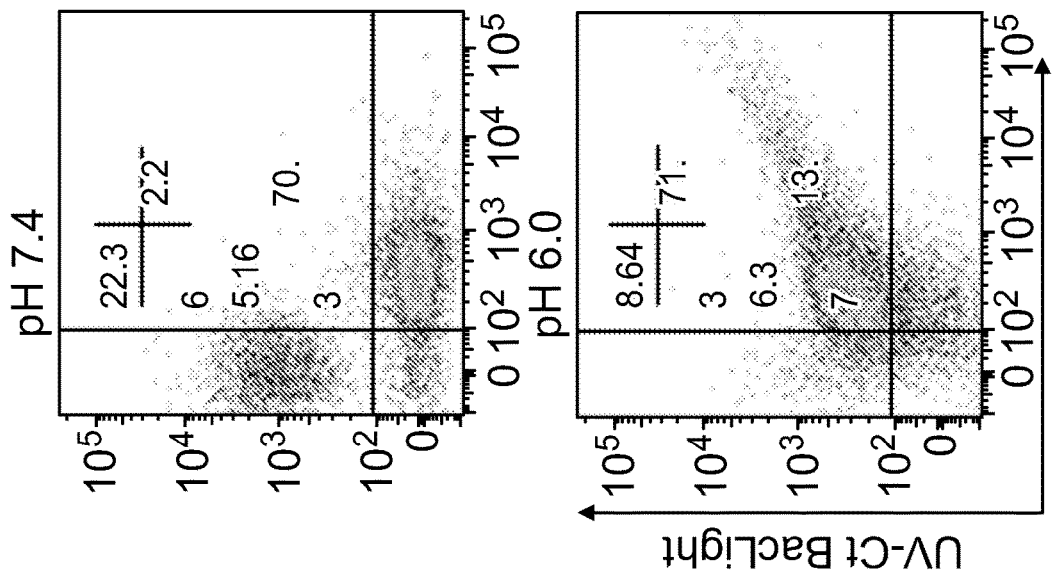

UV inactivated *Chlamydia* (UV-Ct) were stained with a BacLight staining kit and then incubated with Alexa Fluor 488 labeled cSAP or control particles lacking the PLH group (SAP) at pH of 7.4 and 6.0. Flow cytometry was used to examine binding between UV-Ct and cSAP or SAP. UV-Ct binds to cSAPs only at pH 6, not at pH 7.4 (FIGS. 2D-2E).

Evaluation of the Vaccine Compositions

Figure 2F:
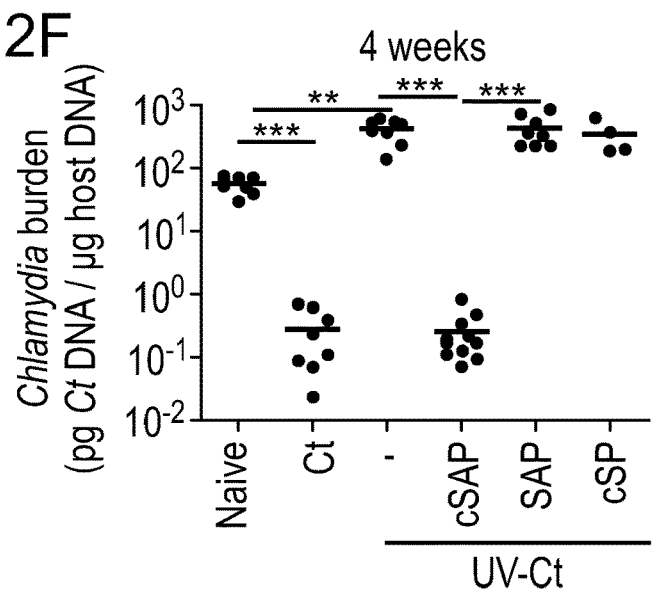
FIG. 2F is a dot plot showing immunization with a vaccine composition including UV-Ct-cSAPs protects the mice against subsequent live *Chlamydia* challenges.
Figure 2G:
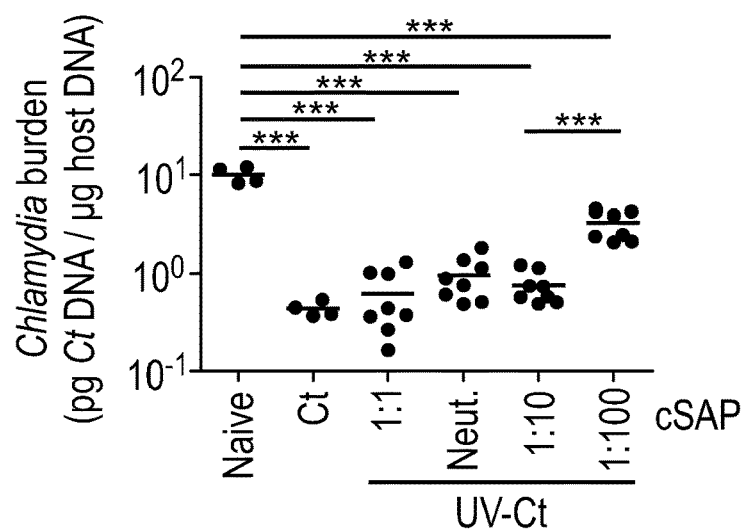
FIG. 2G is a dot plot showing titration or neutralization of the R848-loaded cSAP before attachment to UV-Ct does not change the immune protective property of the vaccine composition.

Immune protective effect of a vaccine composition including UV-inactivated *Chlamydia* attached to R848-loaded nanoparticles was examined Mice were intrauterinely immunized with 10⁶ IFU of infectious *Chlamydia*, or a vaccine composition including UV-inactivated *Chlamydia* (UV-Ct), UV-Ct attached to R848-loaded nanoparticles, UV-Ct attached to empty nanoparticles, or UV-Ct mixed with R848. Four weeks after immunization, immunized mice and naïve control mice were challenged with 10⁶ IFU of live *Chlamydia*. *Chlamydia* loads were measured by qPCR on Day 6 after the challenge Immunization with a vaccine composition including UV-inactivated *Chlamydia* attached to R848-loaded nanoparticles, but not the other compositions, protects the mice against subsequent live *Chlamydia* challenges (FIG. 2F). In certain conditions, R848-loaded nanoparticles were neutralized with sodium hydroxide (NaOH) before attached to UV-inactivated *Chlamydia*. In some other conditions, R848-loaded nanoparticles were diluted 1:10 or 1:100 fold before attached to UV-inactivated *Chlamydia*. A 1:10 titration or neutralization of the R848-loaded nanoparticles before attachment to UV-inactivated *Chlamydia* does not change the immune protective property of the vaccine composition (FIG. 2G).

Figure 2H:
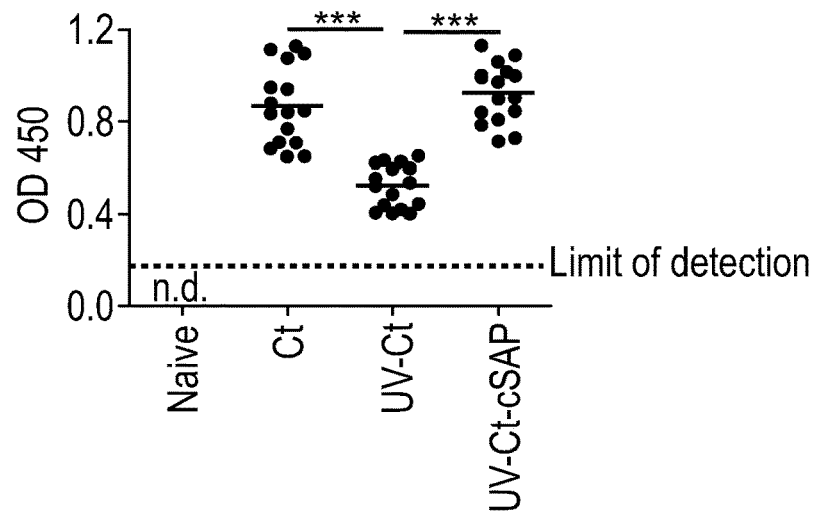
FIG. 2H is a dot plot showing IgG induction by a vaccine composition including UV-Ct-cSAPs. The data were pooled from two independent experiments. n.d.=not detected.

Induction of anti-*Chlamydia* IgG in the serum by live *Chlamydia*, UV-inactivated *Chlamydia*, and UV-Ct-cSAP were determined by ELISA. Data were presented in FIG. 2H as optical densities (OD) for serum from individual mice. UV-Ct-cSAP was able to induce IgG in mice at the similar level as live *Chlamydia* (FIG. 2H).

Figure 3A:
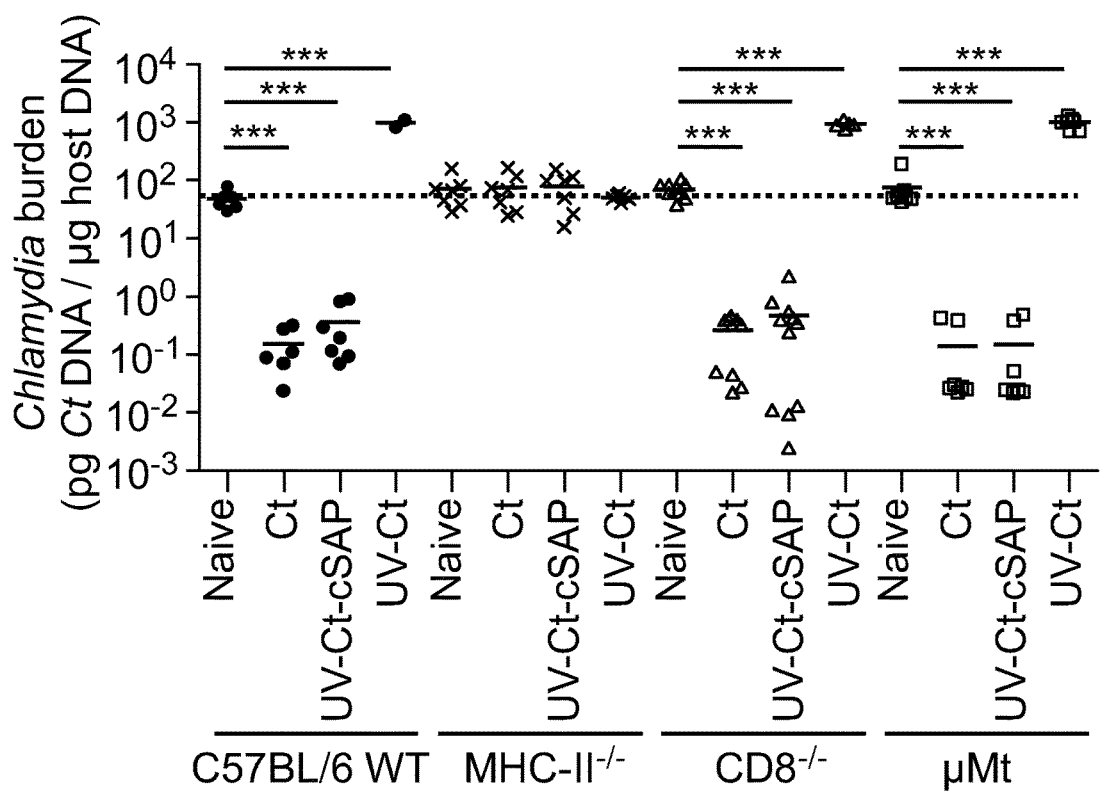
FIGS. 3A-3D are a set of dot plots showing that the protective immunity stimulated by the new *Chlamydia trachomatis* vaccine composition is mediated by CD4$^+$ T cells.
Figure 3B:
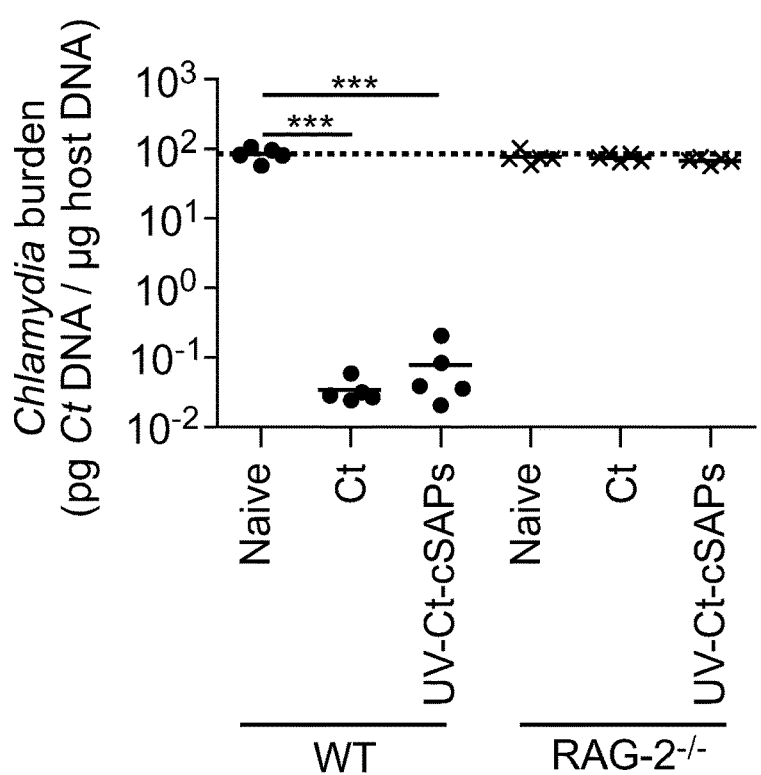
Figure 3C:
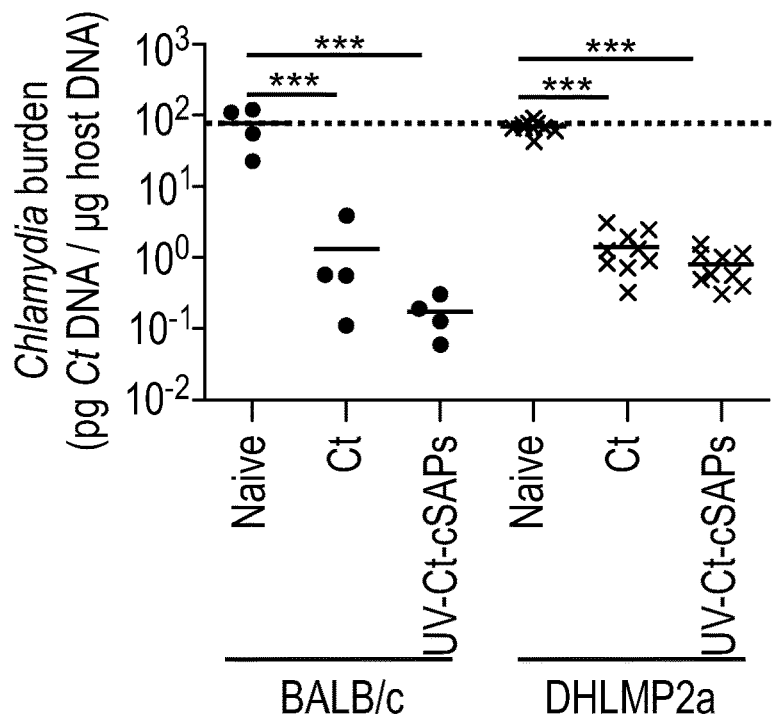

Example 3. *Chlamydia trachomatis* Vaccine Compositions Induced Protective Immunity is Mediated by CD4⁺ T Cells To examine the effector cells that mediate the protective immunity, C57BL/6 wild type, DHLMP2a⁻/⁻ (antibody-deficient), µMt (B cell-deficient), CD8⁻/⁻, MHC class II⁻/⁻ (lack antigen recognition by CD4⁺ T cells) and RAG-2⁻/⁻ mice (lack T and B lymphocytes) were immunized with the new vaccine composition including R848-loaded nanoparticles attached to UV-inactivated *Chlamydia*, and challenged one month later in the genital tract with infectious *Chlamydia*. Protective immunity against subsequent *Chlamydia* infection was preserved in the DHLMP2a⁻/⁻ (antibody-deficient), µMt (B cell-deficient), and CD8⁻/⁻ mice; but lost in MHC class II⁻/⁻ (lack antigen recognition by CD4⁺ T cells) and RAG-2⁻/⁻ (lack T and B lymphocytes) mice (FIG. 3A-3C). These findings indicate that CD4⁺ T cells may play an important role in mediating the protective immunity stimulated by new vaccine composition including R848-loaded nanoparticles attached to UV-inactivated *Chlamydia*.

To confirm that CD4⁺ T cell mediate the protective immunity stimulated by the new vaccine composition, mice were immunized with infectious *Chlamydia* (Ct), UV-inactivated *Chlamydia* (UV-Ct), or the new vaccine composition (UV-Ct-cSAPs). Four weeks later, CD4⁺ or CD8⁺ T cells, or T-cell depleted lymphocytes were isolated from the immunized mice or control mice and transferred to naïve mice. One day after the transfer, recipient mice were challenged with 10⁶ IFU of live *Chlamydia* and the uteri from those mice were harvested 6 days after the challenge. *Chlamydia* loads were determined as described above in Example 1.

Figure 3D:
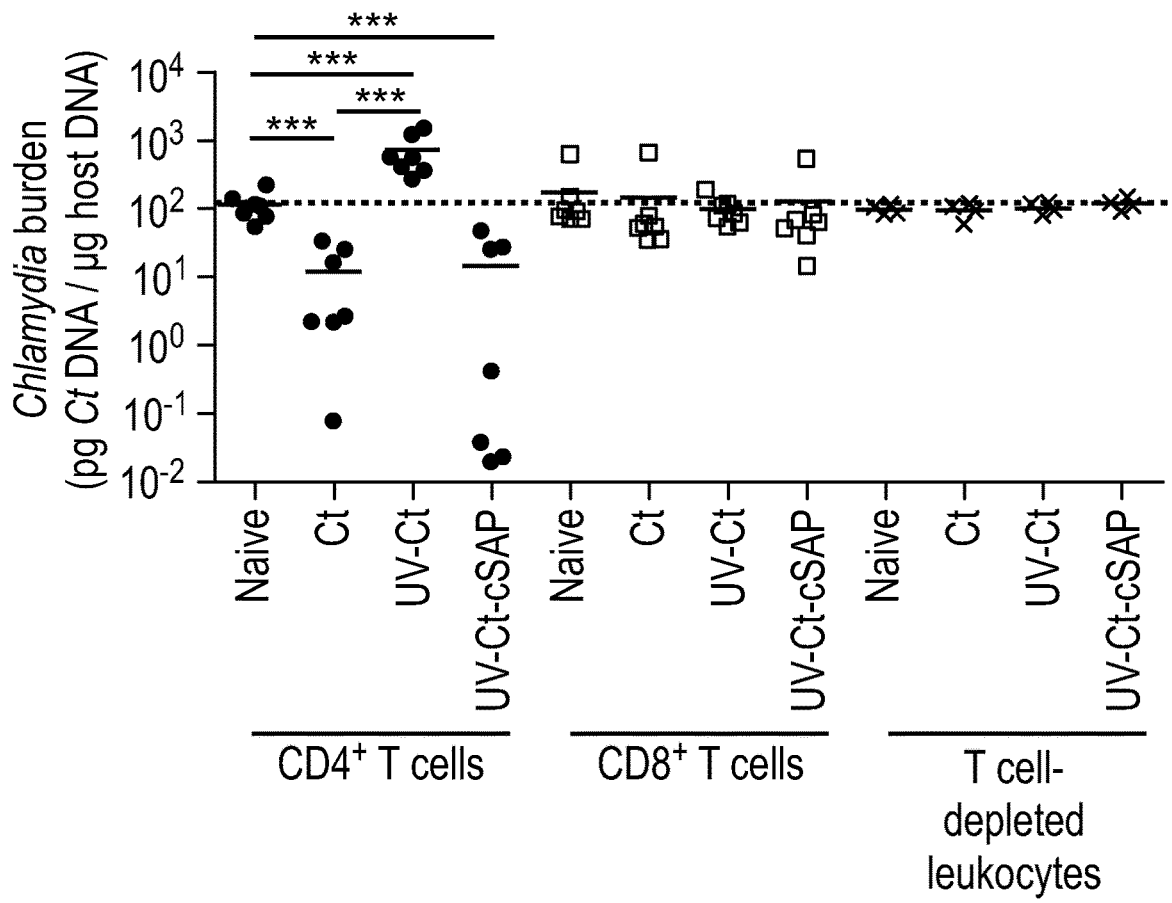

Protective immunity against subsequent *Chlamydia* challenge was observed in recipient mice that were transferred with CD4⁺ T cells obtained from mice immunized with infectious *Chlamydia* or the new vaccine composition, but not in other recipient mice (FIG. 3D). Transfer of CD4⁺ T cells from mice that had been immunized with inactivated *Chlamydia* alone, conferred enhanced susceptibility to subsequent *Chlamydia* challenge, confirming that immune tolerance also depends on CD4⁺ T cells (FIG. 3D). Thus FIG. 3D shows that protective immunity was mediated by CD4⁺ T cells, not CD8⁺ T cells or other lymphocytes.

Figure 4A:
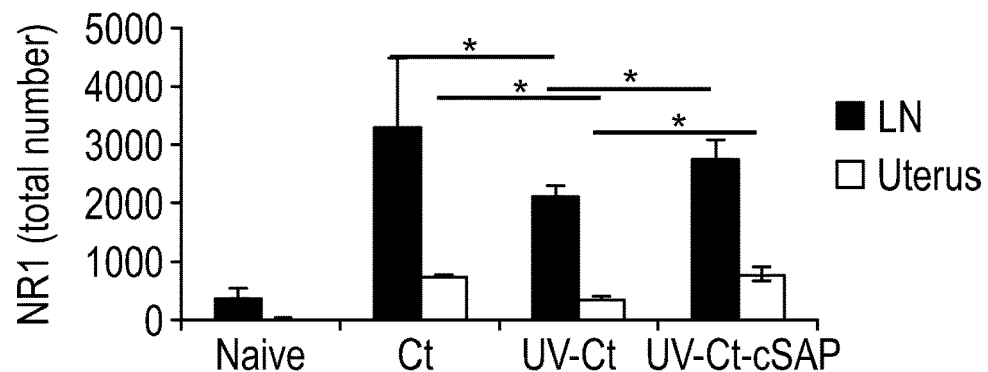
FIG. 4A is a bar graph showing significantly more *Chlamydia*-specific transgenic CD4$^+$ T cells were present in lymph nodes of the mice challenged with the new vaccine composition (UV-Ct-cSAPs) or infectious *Chlamydia* (Ct) when compared with mice immunized with UV-inactivated *Chlamydia* (UV-Ct) or the uninfected control mice (Naive).

Induction of *Chlamydia*-specific CD4+ T cells by the new vaccine composition was examined using *Chlamydia*-specific T cell receptor (TCR) transgenic mice. Wild-type CD90.1+ transgenic CD4+ T cells (NR1 cells) were labeled with a fluorescent dye carboxyfluorescein diacetate succinimidyl ester (CFSE) and transferred into CD90.2 host mice one day before immunization. Recipient mice were intrauterinely challenged with $10^6$ IFU of infectious *Chlamydia* (Ct), UV-inactivated *Chlamydia* (UV-Ct), or the new vaccine composition (UV-Ct-cSAPs). At Day 4 following the challenge, the draining lymph nodes and uteri were harvested from the recipient mice and analyzed by flow cytometry. The absolute number of *Chlamydia*-specific transgenic CD4+ T cells in the lymph node and uterus was enumerated. Significantly more NR1 cells accumulated in the uterus and the draining LNs of the mice challenged with infectious *Chlamydia* or the new vaccine composition when compared with mice challenged with UV-inactivated *Chlamydia* (FIG. 4A).

Figure 4B:
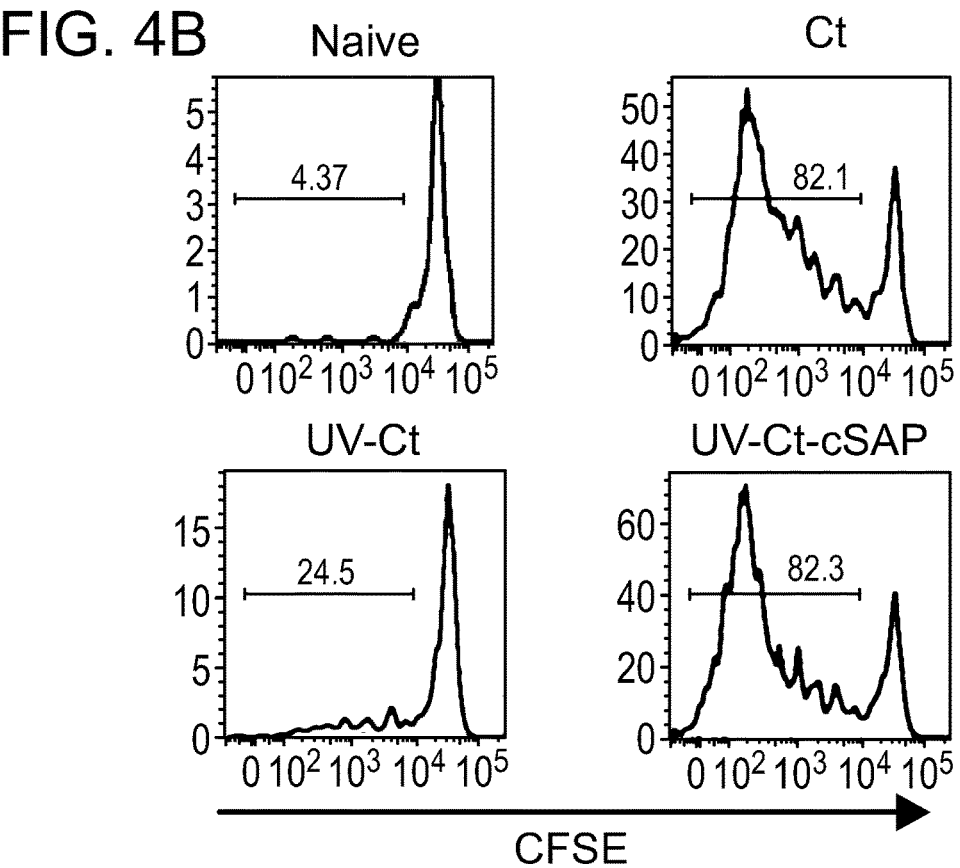
FIG. 4B is a set of flow cytometry graphs showing that the number of *Chlamydia*-specific CD90.1$^+$ CD4$^+$ T cells in mice immunized with Ct or UV-Ct-cSAPs greatly exceeded those in the uninfected mice or mice immunized with UV-Ct, indicating Ct and UV-Ct-cSAPs, but not UV-Ct induce *Chlamydia*-specific CD4$^+$ T cell proliferation.

Proliferation of *Chlamydia*-specific transgenic CD90.1+ CD4+ T cells from the lymph nodes was analyzed for CFSE dilution by flow cytometry. CD90.1+ CD4+ T cells retained high levels of CFSE after transfer into uninfected mice, showing that those CD90.1+ CD4+ T cells did not proliferate in the absence of infection (FIG. 4B). Mice infected with UV-inactivated *Chlamydia* (UV-Ct) have comparable levels of *Chlamydia*-specific CD4+ T cells as the control mice, indicating no stimulation of *Chlamydia*-specific CD4+ T in those mice as well (FIG. 4B). On the other hand, the number of CD90.1+ CD4+ T cells in mice challenged with infectious *Chlamydia* (Ct) or the new vaccine composition (UV-Ct-cSAPs) greatly exceeded those in the uninfected control mice or mice challenged with UV-Ct (FIG. 4B). These findings indicate that the new vaccine composition induced *Chlamydia*-specific CD4+ T cells proliferation in a similar manner as live *Chlamydia*.

CD90.1+ transgenic CD4+ T cells were isolated from lymph nodes on Day 4 following immunization, re-stimulated in vitro by T cell stimulators phorbol 12-myristate 13-acetate (PMA) and ionomycin, and stained for intracellular TNF-α, IFN-γ, and IL-2 production. The number of CD90.1+ CD4+ T cells producing all three cytokines were significantly higher in mice immunized with the new vaccine composition or infectious *Chlamydia* when compared with mice immunized with UV-inactivated *Chlamydia* or the control mice (FIG. 4C), indicating the new vaccine composition induced active *Chlamydia*-specific T cell response in a similar manner as live *Chlamydia*.

Figure 4C:
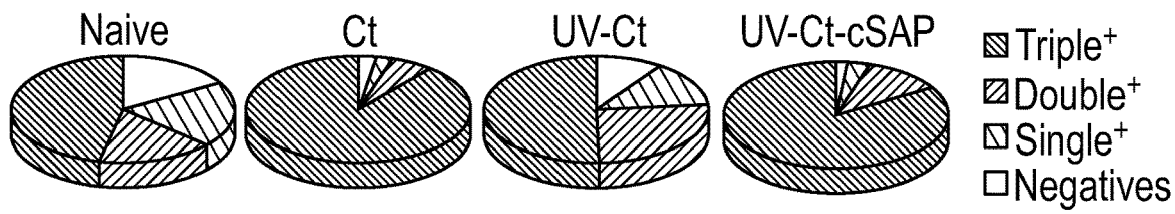
FIG. 4C is a set of pie charts showing that the number of CD90.1$^+$ CD4$^+$ T cells producing all three cytokines (TNF-α, IFN-γ, and IL-2) was significantly higher in mice immunized with Ct or UV-Ct-cSAPs when compared with mice immunized with UV-Ct or the uninfected control mice.

These data show vaccination with UV-Ct-cSAP resulted in NR1 cells proliferation (FIG. 4B) and accumulation in the uterus and the draining LNs (FIG. 4A), which produced cytokines TNF-α, IFN-γ, and IL-2 indistinguishably from mice infected with live *Chlamydia* (FIG. 4C). Therefore, direct linkage of adjuvants to inactivated bacteria promotes a multi-functional antigen-specific cellular immune response that protects the mucosa against subsequent bacterium infection.

Example 4. CD103− Dendritic Cells of the Uterus Induce *Chlamydia*-Specific T Cells CD45+ MHC-II+ antigen presenting cells were sorted into three subsets according to F4/80 and CD103 expression: F4/80+ CD103− macrophages, F4/80− CD103− dendritic cells, and F4/80− CD103+ dendritic cells, and analyzed for CD11c, CD11b, and CX3CR1 expression. F4/80+ CD103− macrophages showed high CD11b and CX3CR1 expression, but low CD11c expression; F4/80− CD103− dendritic cells showed high CD11c, CD11b, and CX3CR1 expression; F4/80− CD103+ dendritic cells showed low CD11b and CX3CR1, but high CD11c expression (FIG. 5A).

Mice were intrauterinely challenged with infectious (Ct), UV-inactivated (UV-Ct) *Chlamydia*, or the new vaccine composition (UV-Ct-cSAPs). 18 or 24 hours after infection, CD45+ MHC-II+ cells were isolated from uteri or lymph nodes, and sorted by fluorescence-activated cell sorting (FACS) according their CD103 and F4/80 expression. *Chlamydia* loads were measured by qPCR per 1,000 sorted antigen-presenting cells. Isolated CD326+ epithelial cells (EC) of the uterus served as positive controls. CD103− dendritic cells have a significantly higher *Chlamydia* loads than F4/80+ macrophages and CD103+ dendritic cells in both uteri (FIG. 5B) and lymph nodes (FIG. 5C), indicating CD103− dendritic cells play important roles in recognizing and presenting *Chlamydia*.

Figure 5D:
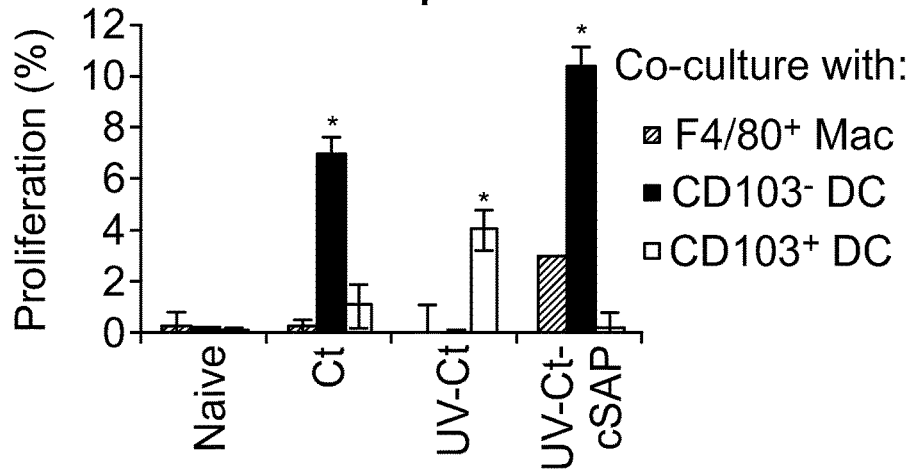
FIGS. 5D and 5E are a set of bar graphs showing CD103$^-$ dendritic cells isolated from uteri of mice immunized with infectious *Chlamydia* (Ct), or the new vaccine composition (UV-Ct-cSAPs), but not the other antigen presenting cells, induced proliferation of *Chlamydia*-specific CD90.1$^+$ CD4$^+$ transgenic T cells (NR1 cells) both in vitro (5D) and in vivo (5E).
Figure 5E:
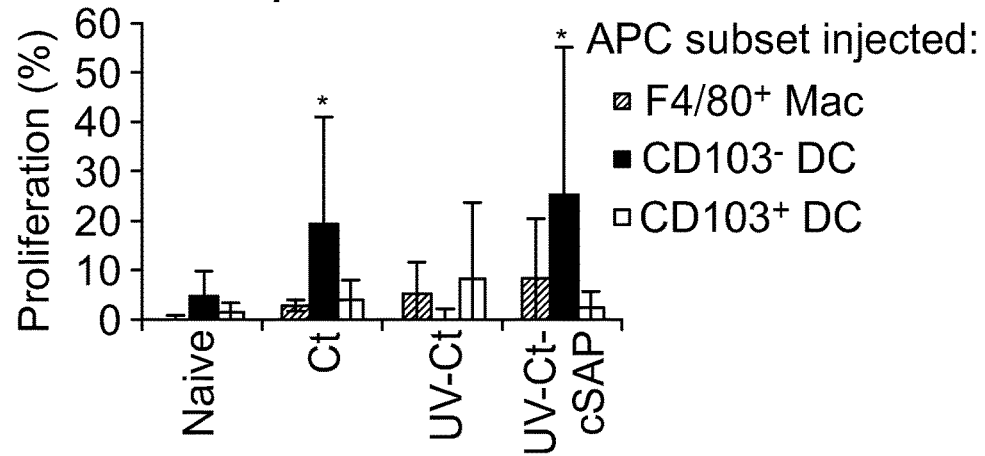
Figure 5F:
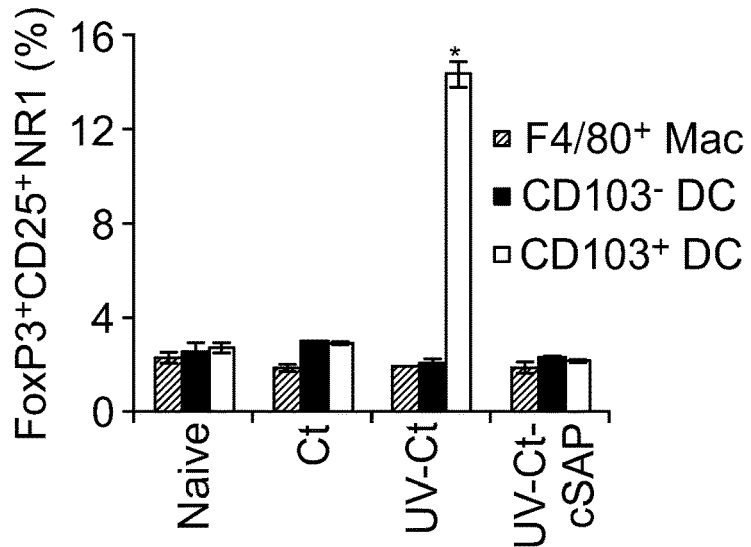
FIG. 5F is a bar graph showing CD103$^+$ dendritic cells increased the number of FoxP3$^+$ CD25$^+$ NR1 cells following UV-Ct immunization.
Figure 6A:
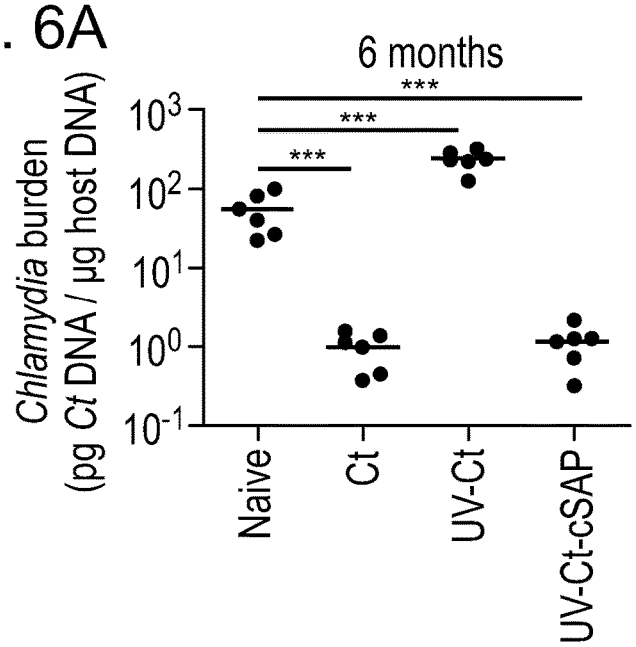
FIG. 6A is a dot plot showing intrauterine immunization with the new vaccine composition or the infectious *Chlamydia*, but not the inactivated *Chlamydia*, resulted in protection against subsequent genital *Chlamydia* infection for six months after immunization.
Figure 6B:
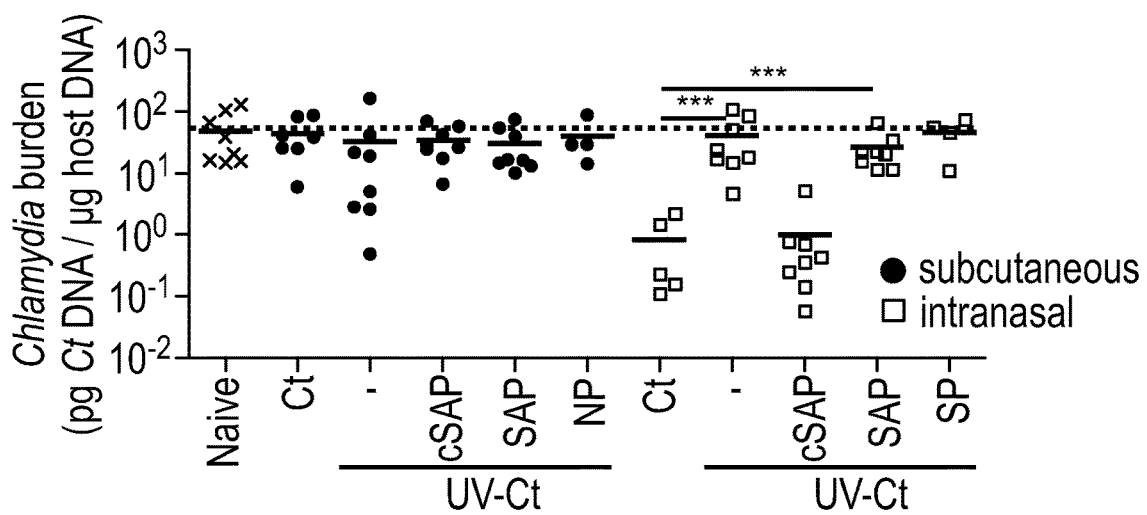
FIG. 6B is a dot plot showing intranasal, but not subcutaneous, immunization with the new vaccine composition resulted in protective immunity against subsequent genital *Chlamydia* infection, indicating that cross-mucosal protective immunity was induced by the new vaccine composition.
Figure 6C:
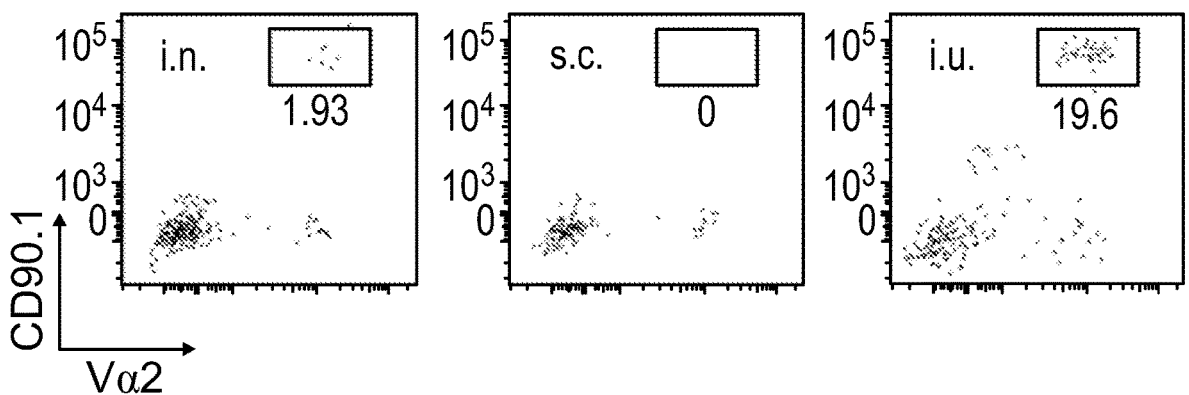
FIG. 6C is a set of flow cytometry graphs showing that tissue homing into the uterus of *Chlamydia*-specific transgenic CD4$^+$ T cells was induced by intrauterine or intranasal, but not subcutaneous immunization.
Figure 6D:
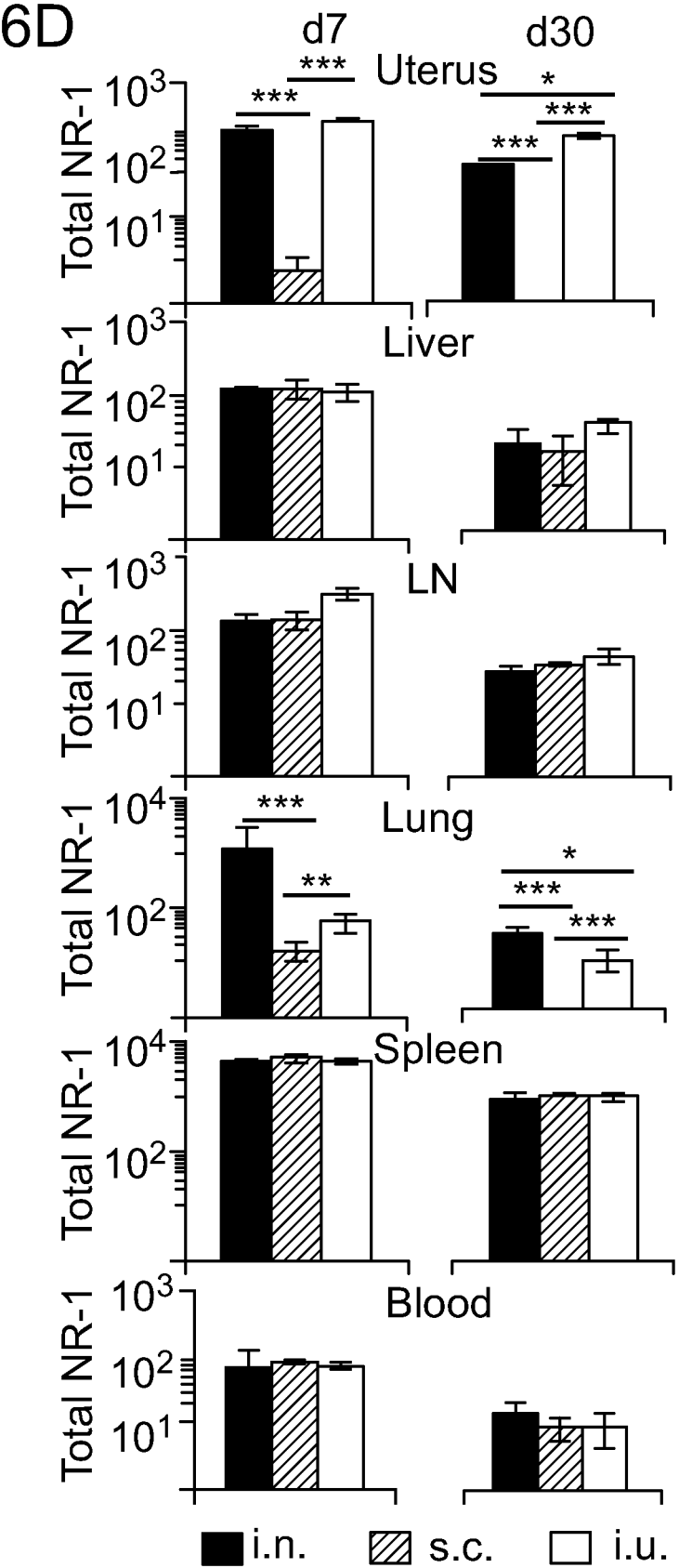
FIG. 6D is a set of bar graphs showing that immunization with UV-Ct-cSAP by either intrauterine (i.u.) or intranasal (i.n.) route, but not by subcutaneous (s.c.) route, induced the recruitment and retention of protective NR1 cells in the genital mucosa and in lung. The numbers of NR1 cells in liver, lymph nodes, spleen, or blood are comparable among the different routes of immunization.
Figure 7A:
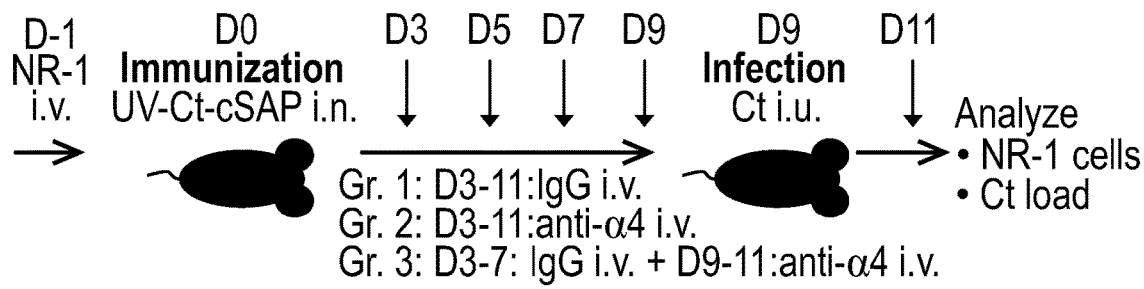
FIG. 7A is a schematic drawing showing the experiment protocol for Example 5.
Figure 7B:
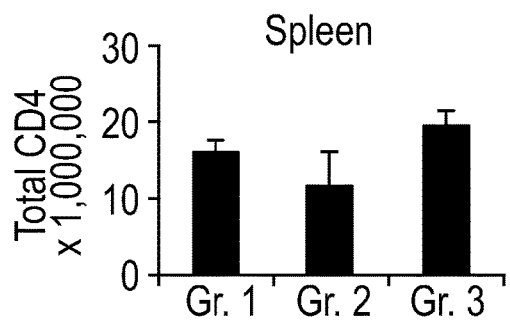
FIGS. 7B-7C are bar graphs showing that blocking alpha 4 integrin efficiently prevented T cell accumulation in uterus (7C), but had no effect on the number of NR1 cells in the spleen (7B).
Figure 7C:
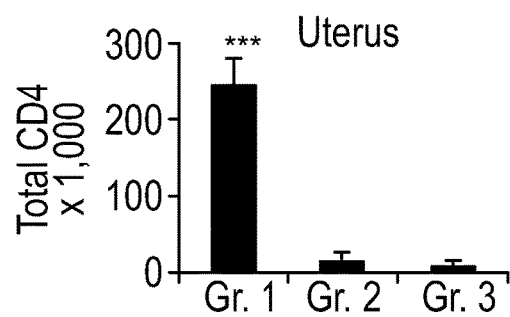
Figure 7D:
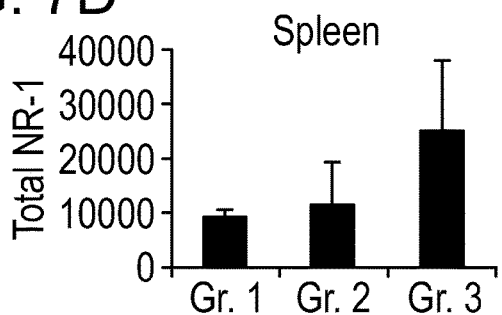
FIG. 7D is a bar graph showing that the systemic NR1 cells present in the spleen were not affected by α4 antibody injections.
Figure 7E:
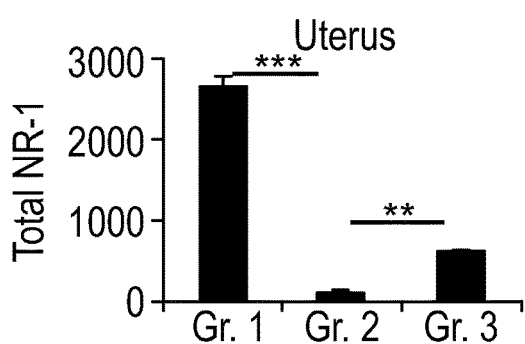
FIG. 7E is a bar graph showing that accumulation of NR1 cells was observed in Gr.1 mice that were treated with IgG, and Gr. 3 mice that were treated with anti-α4 mAb only after the *Chlamydia* challenge, but not in Gr. 2 mice that were treated with anti-α4 mAb after both vaccination and challenge.
Figure 7F:
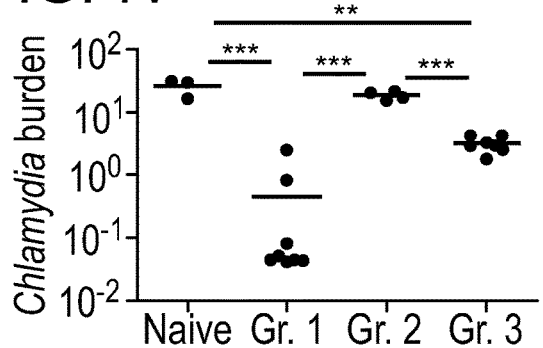
FIG. 7F is a dot plot showing that Gr.3 mice treated with anti-α4 mAb only after the *Chlamydia* challenge (the group containing uterine-resident memory T cells but no additionally recruited circulatory memory cells) were protected against genital *Chlamydia* challenge, compared to the naïve control mice and the Gr. 2 mice treated with anti-α4 mAb after both immunization and challenge.

*Chlamydia*-specific CD4+ transgenic T cells (NR1 cells) were labeled with CFSE and co-cultured for three days with F4/80+ macrophages, CD103− dendritic cells, or CD103+ dendritic cells isolated from the uteri of mice intrauterinely challenged with infectious *Chlamydia* (Ct), UV-inactivated (UV-Ct) *Chlamydia*, or the new vaccine composition (UV-Ct-cSAPs). The proliferation of *Chlamydia*-specific CD4+ transgenic T cells was measured by CFSE dilution. CD103− dendritic cells isolated from uteri of mice immunized with infectious *Chlamydia*, but not the other antigen presenting cells, induce proliferation of *Chlamydia*-specific CD4+ transgenic T cells in vitro (FIG. 5D). The effect of CD103− dendritic cells on *Chlamydia*-specific CD4+ transgenic T cells was then examined in vivo. Wild-type CD90.1+ transgenic CD4+ T cells were labeled with CFSE and transferred into CD90.2 host mice. One day later, recipient mice were injected into the right footpad with isolated F4/80+ macrophages, CD103− dendritic cells, or CD103+ dendritic cells isolated from the uteri of mice immunized with infectious *Chlamydia* (CO, UV-inactivated (UV-Ct) *Chlamydia*, or the new vaccine composition (UV-Ct-cSAPs). Left and right popliteal lymph nodes were analyzed for CFSE-diluted CD90.1+ transgenic CD4+ T cells 3 days after cell injection. Again, CD103− dendritic cells isolated from the uteri of mice immunized with live Ct or UV-Ct-cSAPs, but not other antigen-presenting cells, induce proliferation of *Chlamydia*-specific CD4+ transgenic T cells in right popliteal lymph nodes (FIG. 5E). Thus, CD103− dendritic cells of the uterus induce proliferation of *Chlamydia*-specific T cells both in vitro and in vivo. These data show that CD103− dendritic cells sorted from live *Chlamydia* infected- or UV-Ct-cSAP immunized mice stimulated proliferation of NR1 cells in vitro and in vivo as measured by CFSE dilution (FIG. 5D-5E). CD103+ dendritic cells were able to promote significant NR1 proliferation following UV-Ct immunization only (FIG. 5D) by increasing the number FoxP3+ CD25+ NR1 cells (FIG. 5F). Together these results demonstrate that after *Chlamydia* infection or UV-Ct-cSAP immunization, CD103− dendritic cells from the genital mucosa traffic *Chlamydia* antigens and directly activate *Chlamydia*-specific CD4+ T cells to promote protective immunity. Conversely, UV-Ct is not efficiently taken up by the CD103− dendritic cell population, rather, it is found in CD103+ dendritic cells, leading to the induction of Tregs that might influence the balance between protection and tolerance in the genital mucosa.

Figure 8A:
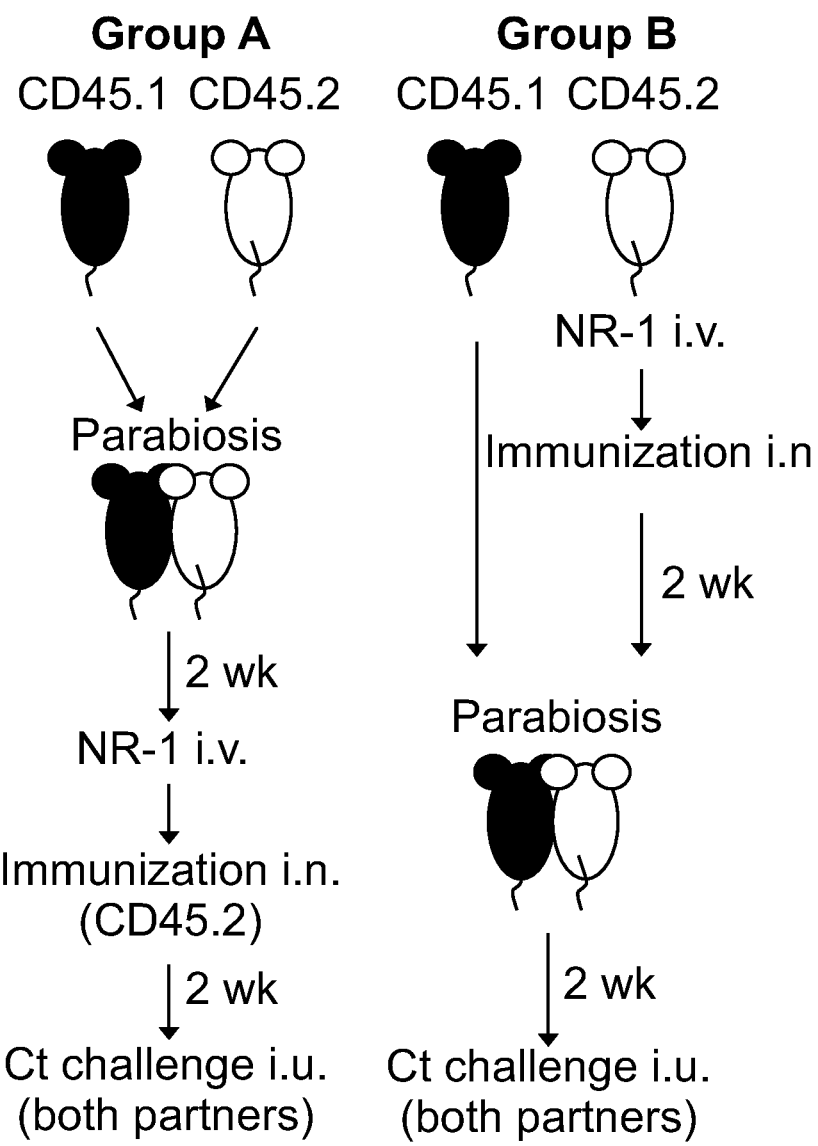
FIG. 8A is a schematic drawing showing the parabiosis experiment protocol for Example 6.
Figure 8B:
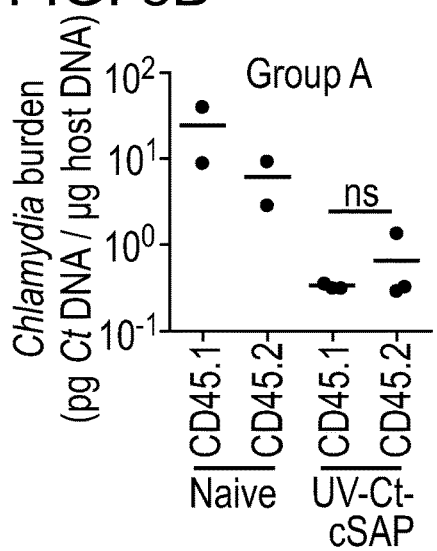
FIGS. 8B-8C are dot plots showing that both partners of the Group A mice were protected against subsequent genital *Chlamydia* challenge (8B); but only the immunized partner (CD45.2), not the other partner (CD45.1) of the Group B mice was protected against subsequent genital *Chlamydia* challenge (8C).
Figure 8C:
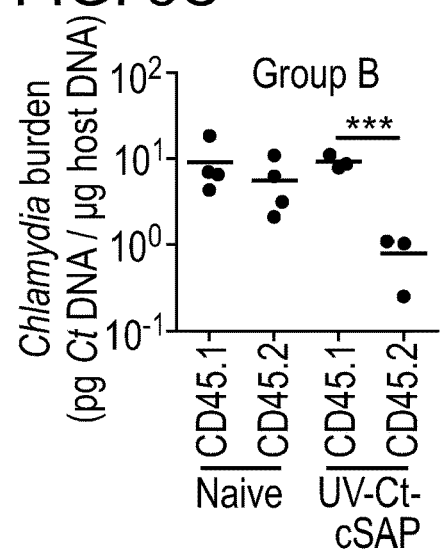
Figure 8D:
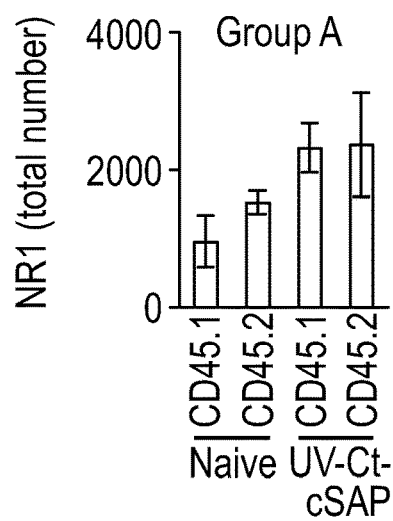
FIGS. 8D-8E are bar graphs showing that more NR-1 cells were present in mice that were protected against subsequent genital *Chlamydia* challenge compared with mice that were not protected.
Figure 8E:
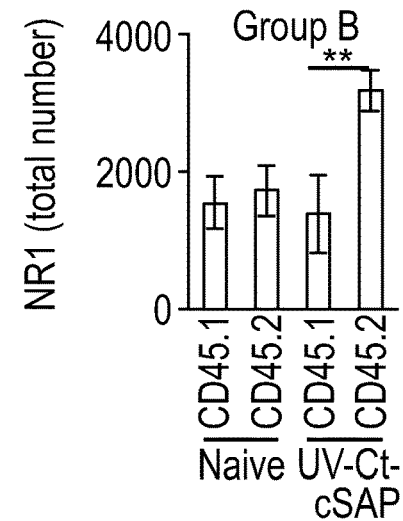
Figure 8F:
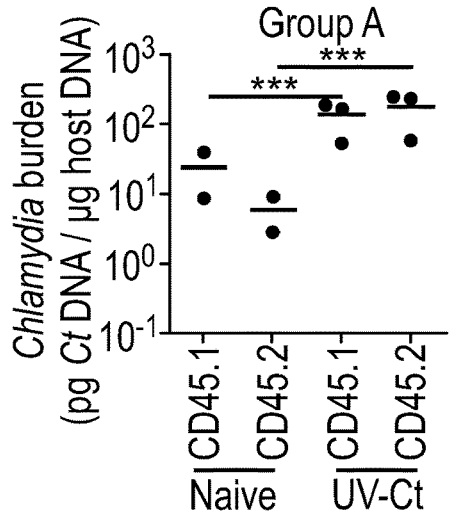
FIGS. 8F-8G are dot plots showing that immunization with UV-Ct induced immune tolerance that are independent of the timing of parabiosis.
Figure 8G:
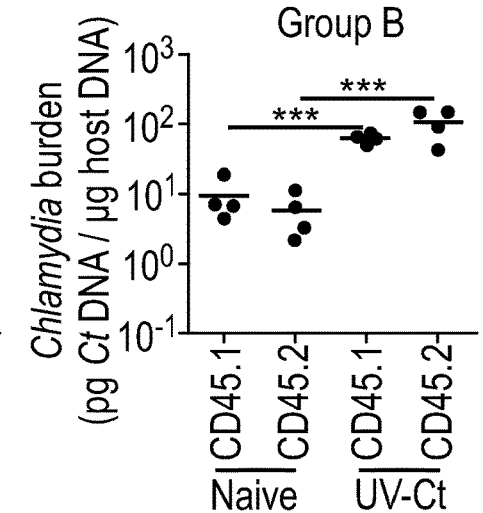

Example 5. Cross-Mucosal Protective Immunity Induced by *Chlamydia trachomatis* Vaccine Compositions The length of the protective immunity induced by the new vaccine compositions was evaluated. Mice were intrauterinely challenged with live *Chlamydia* six months after intrauterine immunization with nothing, infectious or inactivated *Chlamydia*, or the new vaccine composition (UV-Ct-cSAPs). *Chlamydia* loads were determined as described above in Example 1. Intrauterine immunization with the new vaccine composition or the infectious *Chlamydia*, but no the inactivated *Chlamydia*, resulted in protection against subsequent genital *Chlamydia* infection for at least six months after immunization (FIG. 6A), indicating the presence of long-term immunity.

Different routes of vaccine administration were also tested. The new vaccines compositions were administered either through another mucosal interface: intranasal mucosal membrane, or by the traditional route: subcutaneously. For intranasal challenge, mice were anesthetized and a drop of the vaccine compositions was placed on its nostril until it was inhaled. For subcutaneous inoculation, the vaccine compositions were administered under the skin at the base of the tail or flank. Four weeks after immunization, mice were challenged intrauterinely with infectious *Chlamydia*, and *Chlamydia* load were determined Intranasal, but not subcutaneous, immunization with the new vaccine composition (UV-Ct-cSAP) resulted in protective immunity against subsequent genital *Chlamydia* infection (FIG. 6B). Thus, cross-mucosal protective immunity was induced by the new vaccine composition.

Next, wild-type $CD90.1^+$ transgenic $CD4^+$ T cells (NR1) were transferred into CD90.2 host mice one day before they were immunized intrauterinely (i.u.), intranasally (i.n.) or subcutaneously (s.c.) with UV-Ct-cSAPs. At Day 7 following the immunization, the uteri were harvested and analyzed by flow cytometry. The absolute number of *Chlamydia*-specific transgenic $CD4^+$ T cells was enumerated. *Chlamydia*-specific transgenic $CD4^+$ T cells migrated into the genital mucosa tissue by intrauterine or intranasal, but not subcutaneous immunization (FIG. 6C).

Quantitative and/or qualitative differences between the *Chlamydia*-specific T cell response after intranasal immunization and subcutaneous immunization was investigated. Uterus-residing memory cells may be imprinted in the lungs following immunization, then traffic to the genital tract where they mediate protection. To test this hypothesis, mice were injected with NR1 cells and then immunized by different routes with the new vaccine composition UV-Ct-cSAP. The number of NR1 cells was quantified in several organs 7 and 30 days post-vaccination. The induction of circulatory NR1 cells (e.g. in the blood, spleen) as well as the number of NR1 cells in the lymph node and liver was comparable between the different routes of immunization (FIG. 6D).

In contrast, intrauterine immunization led to the highest levels of NR1 recruitment and retention in the genital mucosa while subcutaneous vaccination did not lead to any NR1 retention (FIG. 6D). Interestingly, a significant number of NR1 cells was present in the uterus even 30 days following intranasal immunization (FIG. 6D). The number of NR1 cells in the lungs was reversed to the number of NR1 cells in the uterus for intranasal and intrauterine vaccination (FIG. 6D). These data show that immunization by either intrauterine or intranasal routes is sufficient to induce the recruitment and retention of protective NR1 cells in the genital mucosa.

To dissect the function of mucosal resident and circulation memory T cells, mice were injected intravenously with NR1 cells and then vaccinated intranasally with UV-Ct-cSAP. These immunized mice were divided into three groups and treated with either anti-alpha-4 integrin (α4) monoclonal antibody (mAb) and/or a control IgG as described below. All three groups of mice were challenged with live *Chlamydia* intrauterinely nine days after the immunization (D9). The first group of mice (Gr.1) was treated with the control IgG intravenously from day 3 to day 11 (D3-11). The second group of mice (Gr.2) was treated with anti-α4 mAb during D3-11 to completely block migration of *Chlamydia*-specific T cells. The third group of mice (Gr.3) was treated with the control IgG during D3-9 to allow tissue resident memory T cells to traffic into the genital tissue and then treated with anti-α4 mAb during D9-11 after the *Chlamydia* challenge to block additional recruitment of T cells. Blocking α4 integrin efficiently prevents T cell accumulation in uterus (FIG. 7C), but had no effect on the number of NR1 cells in the spleen (FIG. 7B). The systemic NR1 cells present in the spleen were not affected by α4 antibody injections (FIG. 7D).

FIG. 7E shows that accumulation of NR1 cells was observed in Gr.1 mice that were treated with IgG and Gr. 3 mice that were treated with anti-α4 mAb only after the *Chlamydia* challenge, but not in Gr. 2 mice that were treated with anti-α4 mAb after both vaccination and challenge. FIG. 7F shows that Gr.3 mice treated with anti-α4 mAb only after the *Chlamydia* challenge (the group containing uterine-resident memory T cells but no additionally recruited circulatory memory cells) were significantly protected against genital *Chlamydia* challenge, compared to the naïve control mice and the Gr. 2 mice treated with anti-α4 mAb after both immunization and challenge.

Example 6. Resident Mucosal Memory T Cells are Induced by Immunization at Distant Mucosal Surfaces and Confer Protection Against Subsequent Bacterial Challenges To test the role of resident mucosal memory T cells and recruited circulatory memory T cells in vaccine-induced protection against subsequent bacteria challenges, pairs of parabiotic mice were generated and immunized as shown in FIG. 8A. One of the parabiotic partners (CD45.2) was immunized intranasally with UV-Ct-cSAP or UV-Ct either before (Group B) or after the parabiosis (Group A), while the other partner (CD45.1) was not immunized. Two weeks after parabiosis, the chimerism of lymphocytes was greater than 45% (data not shown). Both partners were challenged with live *Chlamydia* two weeks after the parabiosis or the immunization, whichever occurred later. Level of *Chlamydia* bacteria in the uterus of each mouse was determined by qPCR. Both partners of the Group A mice were protected against subsequent genital *Chlamydia* challenge (FIG. 8B).

When two mice shared blood circulation prior to immunization with UV-Ct-cSAP, the mucosa resident memory cells induced by the immunization can traffic to the uteri of both partners, and confer protection against subsequent bacteria challenge to both mice. For the Group B mice, only the immunized partner (CD45.2), not the other partner (CD45.1) was protected against subsequent genital *Chlamydia* challenge (FIG. 8C). The number of NR-1 cells was higher in mice that were protected against subsequent genital *Chlamydia* challenge when compared with mice that were not protected (FIGS. 8D-8E). Importantly, intrauterine immunization with UV-Ct induced immune tolerance that was independent of the timing of parabiosis (FIGS. 8F-8G).

These data suggest that resident mucosal memory T cells can be induced by immunization with the vaccine composition described herein at a distant mucosal surface and can confer protection against subsequent bacterial challenge. In contrast, immunization with unmodified UV-Ct induces circulating Tregs that influence immune tolerance. Together these data suggest cross-mucosal immunity can be achieved using the *Chlamydia* vaccine compositions described herein.

Example 7. Generation and Evaluation of *Francisella tularensis* Vaccine Composition

*Francisella tularensis* is a Gram-negative intracellular bacterium, which is highly virulent and causes tularemia. Several types of tularemia exist, depending on how and where the bacteria enter the body. The ulceroglandular tularemia is the most common kind of tularemia, where a skin ulcer forms at the site of infection—usually an insect or animal bite. The pneumonic tularemia causes signs and symptoms typical of pneumonia and can be lethal. Due to its low infectious dose, ease of spread by aerosol and high virulence, *Francisella tularensis* is classified as a Class A Select Agent by the U.S. government, along with other potential agents of bioterrorism such as *Yersinia pestis*, Smallpox, and Ebola. There are two different lab strains of *Francisella tularensis*: the attenuated strain LVS and the fully virulent strain SchuS4. LVS is created more than 50 years ago by exhaustive in vitro passage of the bacterium and has been used as a live vaccine. Serious adverse side effects, incomplete immunity, and undefined immunogenic properties make LVS not an ideal vaccine.

Figure 9A:
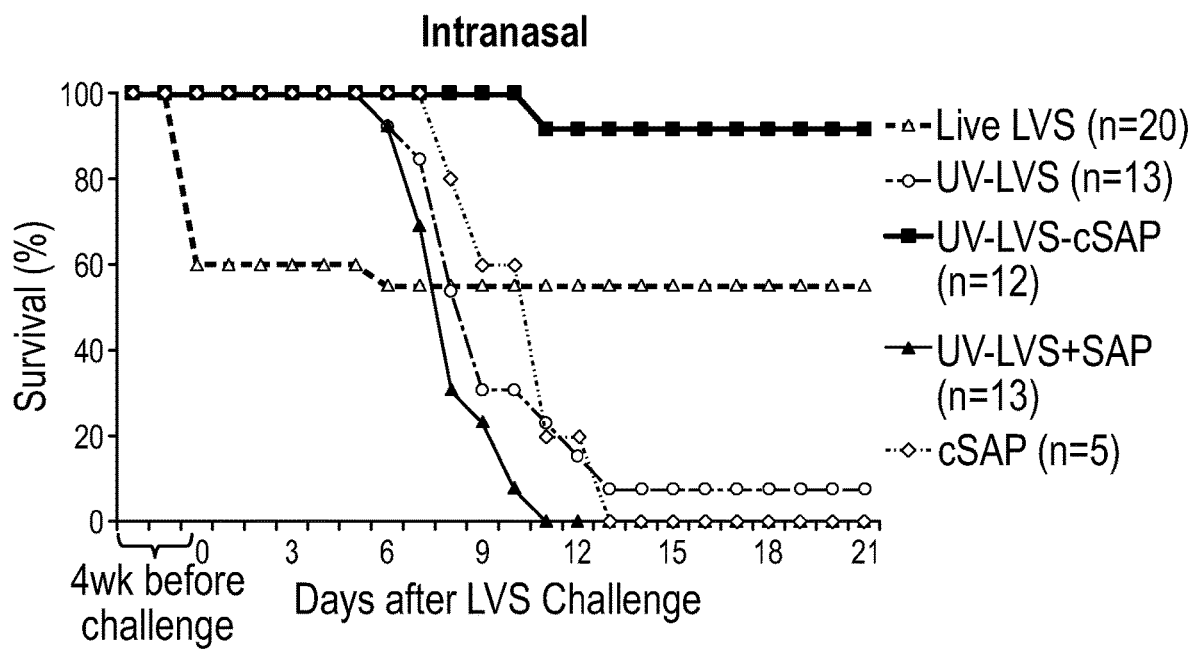
FIG. 9A is a line graph showing that UV-LVS-cSAP-immunized mice were fully protected against subsequent challenge with an attenuated LVS strain of *Francisella tularensis*.

Live LVS bacteria were inactivated by exposure to UV light for 30 minutes. The inactivated LVS bacteria were isolated by infecting human embryonic kidney (HEK) 293 cells to exclude actively proliferating bacteria. R848-loaded nanoparticles were prepared and attached to UV-inactivated *Francisella tularensis* (UV-LVS) as described in Example 2. The vaccine compositions including R848-loaded nanoparticles attached to UV-inactivated LVS (UV-LVS-cSAP) were administered to mice intranasally. Control mice were intranasally administered with live LVS or control particles (cSAP, UV-LVS, UV-LVS+SAP). Four weeks later, the immunized mice and control mice were challenged intranasally with a lethal dose of live LVS, and the survival of these mice were observed for 21 days. FIG. 9A shows that UV-LVS-cSAP-immunized mice were fully protected against subsequent challenge by the attenuated LVS strain of *Francisella tularensis*.

Figure 9B:
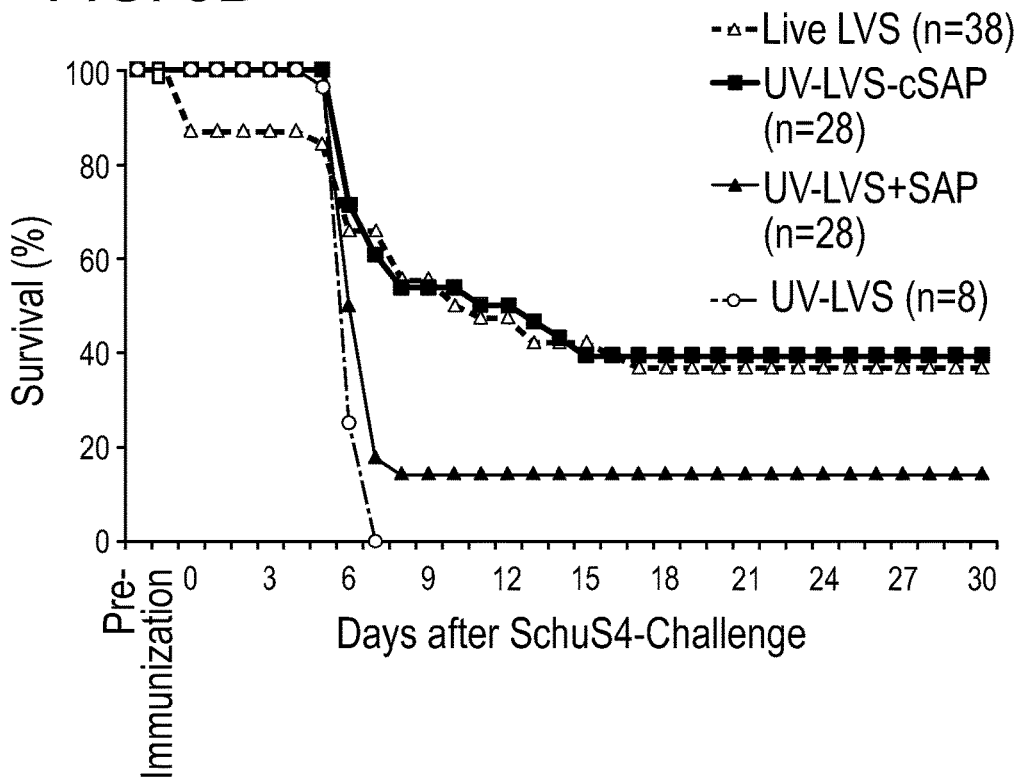
FIG. 9B is a line graph showing that UV-LVS-cSAP-immunized mice were partially protected against subsequent challenge with a fully virulent SchuS4 strain of *Francisella tularensis*.

Protection conferred by the vaccine composition against subsequent challenge by the fully virulent SchuS4 strain of *Francisella tularensis* was investigated. Mice were immunized intranasally with UV-LVS-cSAP, or treated with live LVS, or control particles (UV-LVS or UV-LVS+SAP). Two booster immunizations or treatments with the same composition were performed at two-week intervals. Four weeks later, the immunized mice and control mice were challenged intranasally with the fully virulent SchuS4 strain, and the survival of these mice were observed for 30 days. FIG. 9B shows that UV-LVS-cSAP-immunized mice were partially protected against subsequent challenge by the fully virulent SchuS4 strain of *Francisella tularensis*.

Figure 9C:
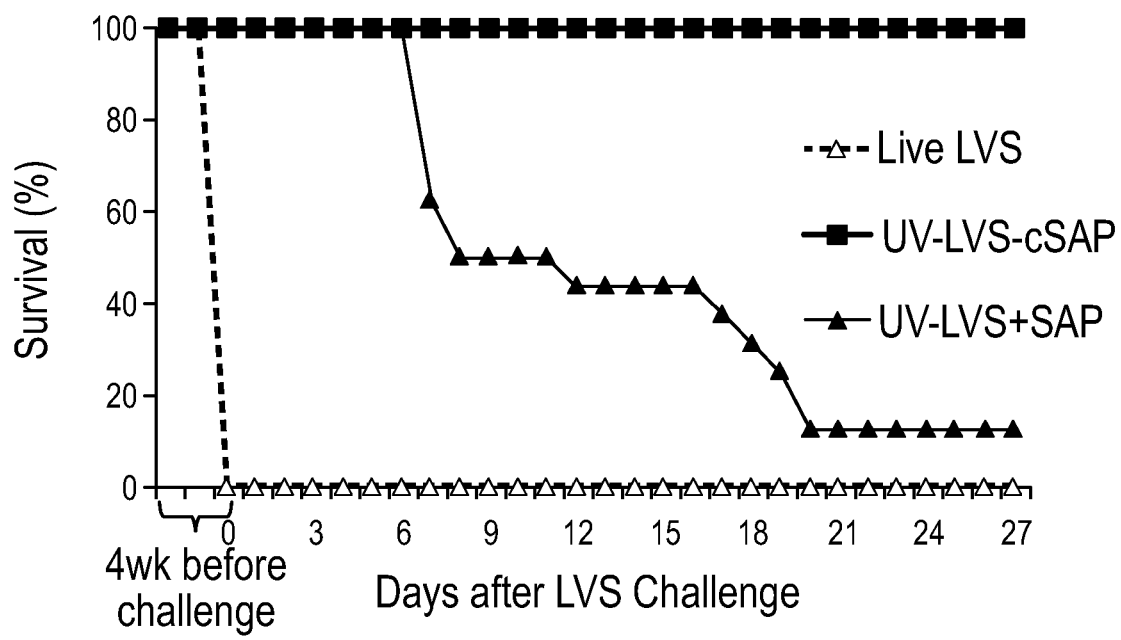
FIGS. 9C-9D are line graphs showing that full protection against subsequent challenge with an attenuated LVS strain of *Francisella tularensis* was obtained after immunization with UV-LVS-cSAP by intraperitoneal route (9C), but not by the subcutaneous route (9D).
Figure 9D:
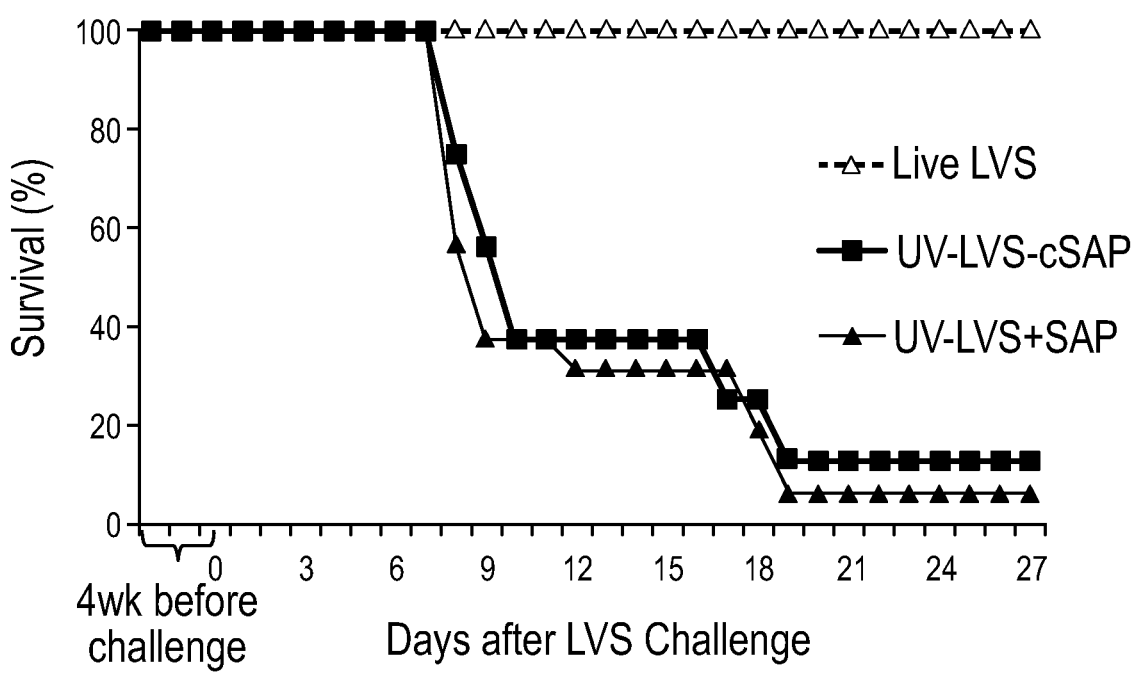

The effect of the administration route on the protective immunity was studied. Mice were treated with UV-LVS-cSAP, live LVS, or UV-LVS+SAP, either subcutaneously or intraperitoneally. Four weeks later, the immunized mice and control mice were challenged intranasally with a lethal dose of live LVS, and the survival of these mice were observed for 21 days. Full protection against subsequent challenge with LVS was obtained after immunization with UV-LVS-cSAP by the intraperitoneal route (FIG. 9C), but not by the subcutaneous route (FIG. 9D).

Figure 9E:
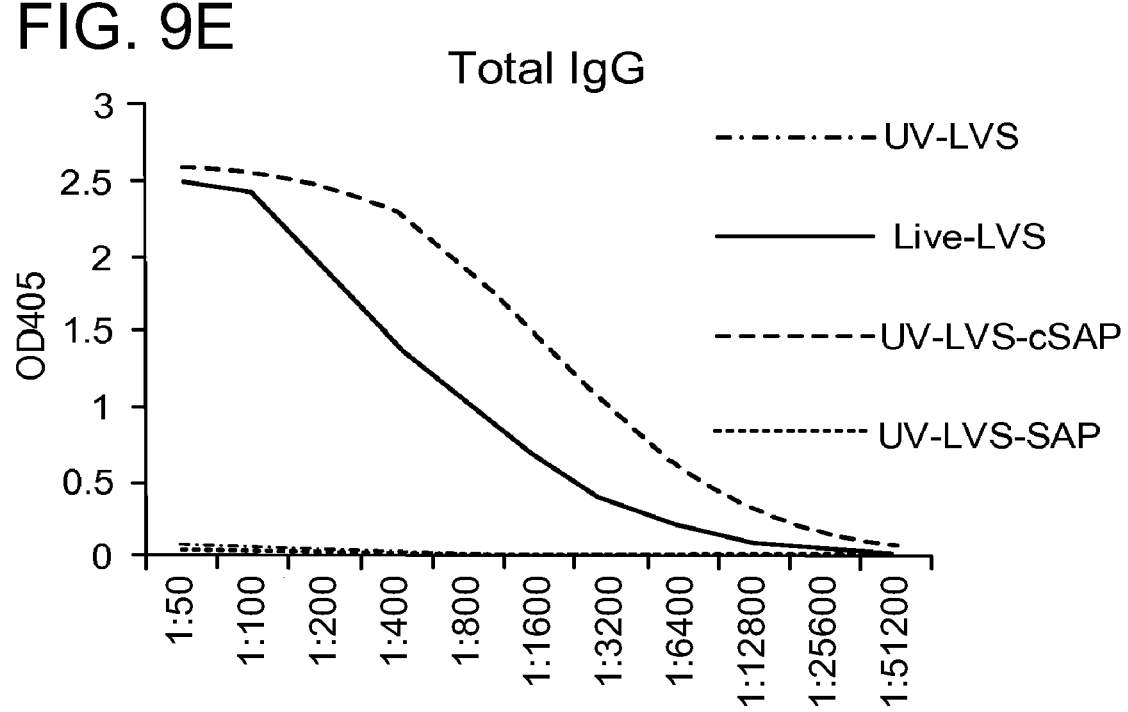
FIGS. 9E-9F are line graphs showing that the levels of induced IgG (9E) and IgM (9F) antibodies were higher in UV-LVS-cSAP-immunized mice than in live LVS-infected mice.
Figure 9F:
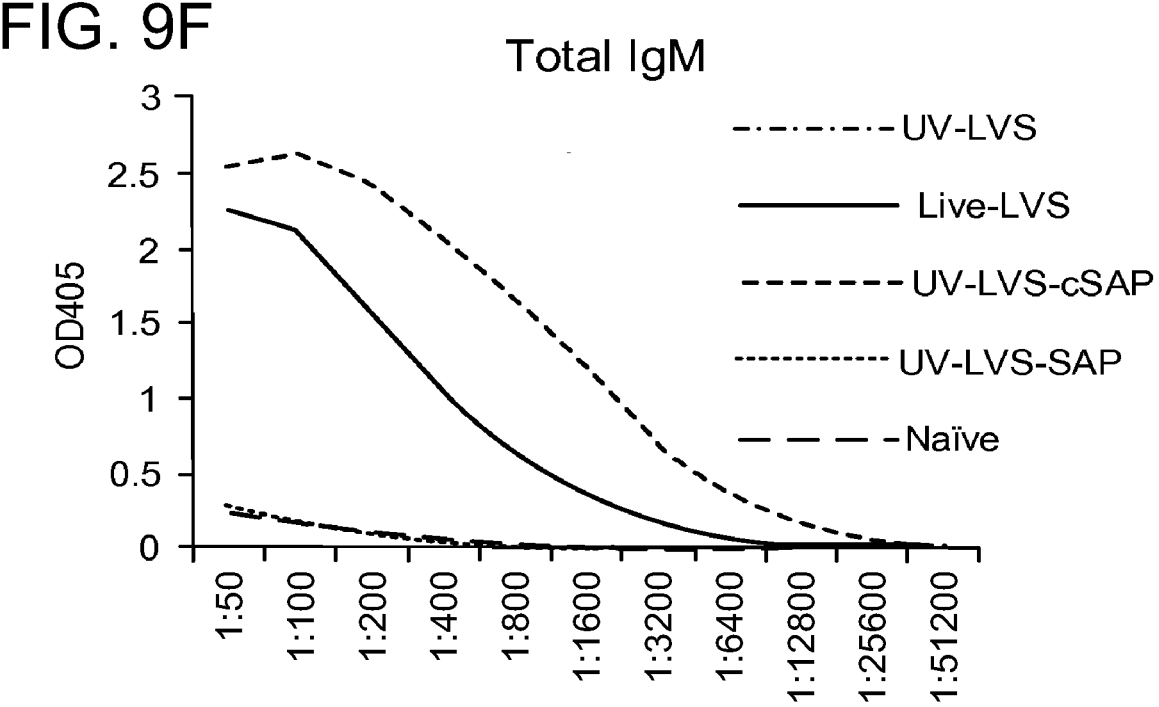

Induction of IgG and IgM antibodies four weeks after UV-LVS-cSAP immunization was studied. The levels of induced IgG (FIG. 9E) and IgM (FIG. 9F) antibodies were higher in UV-LVS-cSAP-immunized mice than in live LVS-infected mice. Treatment with the control particles (UV-LVS+SAP or UV-LVS) did not induce an increase in the IgG or IgM antibodies (FIGS. 9E-9F).

These data suggest that immunization with the *Francisella tularensis* vaccine composition described herein is protective against subsequent *Francisella tularensis* challenges.

Example 8. Generation and Evaluation of *Streptococcus pneumoniae* Vaccine Composition

*Streptococcus pneumoniae*, or *pneumococcus*, is a Gram-positive, alpha-hemolytic, aerotolerant anaerobic bacterium. A significant human pathogenic bacterium, *pneumococcus* is a major cause of pneumonia, and can be isolated in nearly 50% of pneumonia cases. Despite the name, *pneumococcus* can cause many types of pneumococcal infections other than pneumonia, including acute sinusitis, otitis media, meningitis, bacteremia, sepsis, osteomyelitis, septic arthritis, endocarditis, peritonitis, pericarditis, cellulitis, and brain abscess.

Live *pneumococcus* bacteria are inactivated by exposure to UV light for 30 minutes. The inactivated *pneumococcus* bacteria are isolated by infecting human embryonic kidney (HEK) 293 cells to exclude actively proliferating bacteria. R848-loaded nanoparticles are prepared and attached to UV-inactivated *pneumococcus* as described in Example 2. The vaccine compositions including R848-loaded nanoparticles attached to UV-inactivated *pneumococcus* are administered to mice intranasally and evaluated by the methods described in Example 2. A month later, mice immunized with *pneumococcus* vaccine composition and naïve control mice are challenged with live *pneumococcus*, and RNA samples are prepared from mice tissues. *Pneumococcus* loads are measured by qPCR of *pneumococcus* 16s RNA normalized to mouse GAPDH. The *pneumococcus* vaccine composition is determined to be effective when *pneumococcus* load is lower in mice immunized with the vaccine composition than the control mice.

Example 9. Generation and Evaluation of Methicillin-Resistant *Staphylococcus aureus* Vaccine Composition Methicillin-resistant *Staphylococcus aureus* (MRSA) is any strain of *Staphylococcus aureus* that has developed, through the process of natural selection, resistance to beta-lactam antibiotics, including the penicillins (methicillin, dicloxacillin, nafcillin, oxacillin, etc.) and the cephalosporins. Strains unable to resist these antibiotics are classified as methicillin-sensitive *Staphylococcus aureus*, or MSSA. Development of such antibiotic resistance does not cause the bacteria to be more intrinsically toxic than strains of *Staphylococcus aureus* that have no antibiotic resistance, but resistance does make MRSA infection more difficult to treat with standard types of antibiotics and thus more dangerous.

*Staphylococcus aureus* most commonly colonizes the nostrils, other respiratory tract, open wounds, intravenous catheters, or the urinary tract. Healthy individuals may carry MRSA asymptomatically for periods ranging from a few weeks to many years. Patients with compromised immune systems are at a significantly greater risk of symptomatic secondary infection. MRSA is especially troublesome in hospitals, prisons and nursing homes, where patients with open wounds, invasive devices, and weakened immune systems are at greater risk of infection than the general public.

Live MRSA are inactivated by exposure to UV light for 30 minutes. The inactivated MRSA are isolated by infecting human embryonic kidney (HEK) 293 cells to exclude actively proliferating bacteria.

R848-loaded nanoparticles are prepared and attached to UV-inactivated MRSA described in Example 2. The vaccine compositions including R848-loaded nanoparticles attached to UV-inactivated MRSA are administered to mice nasally and evaluated by the methods described in Example 2. A month later, mice immunized with MRSA vaccine composition and naïve control mice are challenged with live MRSA, and RNA samples are prepared from mice tissues. MRSA loads are measured by qPCR of MRSA 16s RNA normalized to mouse GAPDH. The MRSA vaccine composition is determined to be effective when MRSA load is lower in mice immunized with the vaccine composition than the control mice.

Example 10. Generation and Evaluation of Influenza A Virus Vaccine Composition Influenza A virus is a genus of the Orthomyxoviridae family of viruses and can cause influenza in birds and mammals. Some isolates of Influenza A virus causes severe disease both in domestic poultry and in humans. Transmission of Influenza A viruses from wild aquatic birds to domestic poultry can cause an outbreak and give rise to human influenza pandemics.

Live Influenza A viruses are inactivated by exposure to UV light for 30 minutes. The inactivated Influenza A viruses are isolated by infecting human embryonic kidney (HEK) 293 cells to exclude actively proliferating viruses.

R848-loaded nanoparticles are prepared and attached to UV-inactivated Influenza A viruses as described in Example 2. The vaccine compositions including R848-loaded nanoparticles attached to UV-inactivated Influenza A viruses are administered to mice intranasally and evaluated by the methods described in Example 2. A month later, mice immunized with Influenza A viruses vaccine compositions and naïve control mice are challenged with live Influenza A viruses, and RNA samples are prepared from mice blood samples. Influenza A virus loads are measured by qPCR of Influenza A virus RNA normalized to mouse GAPDH. The Influenza A virus vaccine composition is determined to be effective when Influenza A virus load is lower in mice immunized with the vaccine composition than the control mice.

Example 11. Generation and Evaluation of Human Respiratory Syncytial Virus (RSV) Vaccine Composition Human respiratory syncytial virus (RSV) is a virus that causes respiratory tract infections. RSV is a negative-sense, single-stranded RNA virus of the family Paramyxoviridae, which includes common respiratory viruses such as those causing measles and mumps. RSV is a member of the paramyxovirus subfamily Pneumovirinae. It is a major cause of lower respiratory tract infections and hospital visits during infancy and childhood. In the United States, 60% of infants are infected during their first RSV season, and nearly all children will have been infected with the virus by 2-3 years of age. About 2-3% of the patients infected with RSV develop bronchiolitis, necessitating hospitalization.

Live RSV viruses are inactivated by exposure to UV light for 30 minutes. The inactivated RSV viruses are isolated by infecting human embryonic kidney (HEK) 293 cells to exclude actively proliferating virus. An RSV vaccine also can be made using virus-like particles or pseudotyped viruses that contain antigenic RSV proteins.

R848-loaded nanoparticles are prepared and attached to UV-inactivated RSV as described in Example 2. The vaccine compositions including R848-loaded nanoparticles attached to UV-inactivated RSV are administered to mice intranasally and evaluated by the methods described in Example 2. A month later, mice immunized with RSV vaccine composition and naïve control mice are challenged with live RSV, and RNA samples are prepared from mice tissues. RSV loads are measured by qPCR of RSV 16s RNA normalized to mouse GAPDH. The RSV vaccine composition is determined to be effective when RSV load is lower in mice immunized with the vaccine composition than the control mice that are not immunized.

Example 12. Generation and Evaluation of SARS Coronavirus Vaccine Composition Severe acute respiratory syndrome (SARS) is a viral respiratory disease of zoonotic origin caused by the SARS coronavirus (SARS-CoV). Between November 2002 and July 2003, an outbreak of SARS in southern China caused 775 deaths in multiple countries with a fatality rate of about 9.6%, according to the World Health Organization. Initial symptoms are flu-like and may include fever, myalgia, lethargy symptoms, cough, sore throat, and other nonspecific symptoms.

Live SARS-CoV viruses are inactivated by exposure to UV light for 30 minutes. The inactivated SARS-CoV viruses are isolated by infecting human embryonic kidney (HEK) 293 cells to exclude actively proliferating virus.

CpG-loaded nanoparticles are synthesized by encapsulating CpG oligodeoxynucleotide type C into nanoparticles using single or double emulsion process as described in US 2012/0213812. Encapsulation is accomplished by dissolving the CpG oligodeoxynucleotide type C in an aqueous buffer and then using this solution in the single or double emulsion process with the charge-switching copolymers described in Example 2 to form nanoparticles by self-assembly. CpG-loaded nanoparticles are then attached to UV-inactivated SARS-CoV as described in Example 2. The vaccine compositions including CpG-loaded nanoparticles attached to UV-inactivated SARS-CoV are administered to mice intranasally and evaluated by the methods described in Example 2.

A month later, mice immunized with SARS-CoV vaccine composition and naïve control mice are challenged with live SARS-CoV, and RNA samples are prepared from mice tissues. SARS-CoV loads are measured by qPCR of SARS-CoV 16s RNA normalized to mouse GAPDH. The SARS-CoV vaccine composition is determined to be effective when SARS-CoV load is lower in mice immunized with the vaccine composition than the control mice that are not immunized.

Example 13. Generation and Evaluation of Norovirus Vaccine Composition

Norovirus is a genus of genetically diverse single-stranded RNA, non-enveloped viruses in the Caliciviridae family. The viruses are transmitted by fecally contaminated food or water; by person-to-person contact; and via aerosolization of the virus and subsequent contamination of surfaces. Noroviruses are the most common cause of viral gastroenteritis in humans, and affect people of all ages. The known viruses in the genus are all considered to be the variant strains of a single species called Norwalk virus. This species causes approximately 90% of epidemic nonbacterial outbreaks of gastroenteritis around the world and may be responsible for 50% of all foodborne outbreaks of gastroenteritis in the United States. Norovirus infection is characterized by nausea, forceful vomiting, watery diarrhea, and abdominal pain, and in some cases, loss of taste. General lethargy, weakness, muscle aches, headache, and low-grade fever may occur.

Live Noroviruses are inactivated by exposure to UV light for 30 minutes. The inactivated Noroviruses are isolated by infecting human embryonic kidney (HEK) 293 cells to exclude actively proliferating virus.

CpG-loaded nanoparticles are synthesized as described in Example 12. CpG-loaded nanoparticles are then attached to UV-inactivated Noroviruses as described in Example 2. The vaccine compositions including CpG-loaded nanoparticles attached to UV-inactivated Noroviruses are administered to mice intranasally and evaluated by the methods described in Example 2.

A month later, mice immunized with Norovirus vaccine composition and naïve control mice are challenged with live Noroviruses, and RNA samples are prepared from mice tissues. Noroviruse loads are measured by qPCR of Norovirus 16s RNA normalized to mouse GAPDH. The Norovirus vaccine composition is determined to be effective when Norovirus load is lower in mice immunized with the vaccine composition than the control mice that are not immunized.

Example 14. Generation and Evaluation of Human Immunodeficiency Virus (HIV) Vaccine Composition The human immunodeficiency virus (HIV) is a lentivirus that causes the acquired immunodeficiency syndrome (AIDS), a condition in humans in which progressive failure of the immune system allows life-threatening opportunistic infections and cancers to thrive. Infection with HIV occurs by the transfer of blood, semen, vaginal fluid, pre-ejaculate, or breast milk. Within these bodily fluids, HIV is present as both free virus particles and virus within infected immune cells. HIV infects vital cells in the human immune system such as helper T cells (specifically CD4+ T cells), macrophages, and dendritic cells, killing those cells.

HIV viruses are inactivated by exposure to UV light for 30 minutes. The inactivated HIV viruses are isolated by infecting human embryonic kidney (HEK) 293 cells to exclude actively proliferating virus.

Monophosphoryl lipid A (MPLA)-loaded nanoparticles are synthesized by encapsulating MPLA into nanoparticles using single or double emulsion process. MPLA-loaded nanoparticles are then attached to UV-inactivated HIV as described in Example 2. The vaccine compositions including MPLA-loaded nanoparticles attached to UV-inactivated HIV are administered to mice intranasally and evaluated by the methods described in Example 2.

A month later, mice immunized with HIV vaccine composition and naïve control mice are challenged with live HIV, and RNA samples are prepared from mice tissues. HIV loads are measured by qPCR of HIV 16s RNA normalized to mouse GAPDH. The HIV vaccine composition is determined to be effective when HIV load is lower in mice immunized with the vaccine composition than the control mice that are not immunized.

Example 15. Generation and Evaluation of Tuberculosis Vaccine Composition

Tuberculosis (TB) is an infectious disease caused by various strains of mycobacteria, usually *Mycobacterium tuberculosis*. Tuberculosis typically attacks the lungs, but can also affect other parts of the body. It is spread through the air when people who have an active TB infection cough, sneeze, or otherwise transmit respiratory fluids through the air. Most infections do not have symptoms, known as latent tuberculosis. About one in ten latent infections eventually progresses to active disease which, if left untreated, kills more than 50% of those infected. The classic symptoms of active TB infection are a chronic cough with blood-tinged sputum, fever, night sweats, and weight loss. Infection of other organs causes a wide range of symptoms. Treatment is difficult and requires administration of multiple antibiotics over a long period of time. Antibiotic resistance is a growing problem in multiple drug-resistant tuberculosis (MDR-TB) infections.

*Mycobacterium tuberculosis* are inactivated by exposure to UV light for 30 minutes. The inactivated *Mycobacterium tuberculosis* are isolated by infecting human embryonic kidney (HEK) 293 cells to exclude actively proliferating virus.

Monophosphoryl lipid A (MPLA)-loaded nanoparticles are synthesized as described in Example 14. MPLA-loaded nanoparticles are then attached to UV-inactivated *Mycobacterium tuberculosis* as described in Example 2. The vaccine compositions including MPLA-loaded nanoparticles attached to UV-inactivated *Mycobacterium tuberculosis* are administered to mice intranasally and evaluated by the methods described in Example 2.

A month later, mice immunized with *Mycobacterium tuberculosis* vaccine composition and naïve control mice are challenged with live *Mycobacterium tuberculosis*, and RNA samples are prepared from mice tissues. *Mycobacterium tuberculosis* loads are measured by qPCR of *Mycobacterium tuberculosis* 16s RNA normalized to mouse GAPDH. The *Mycobacterium tuberculosis* vaccine composition is determined to be effective when *Mycobacterium tuberculosis* load is lower in mice immunized with the vaccine composition than the control mice that are not immunized.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of stimulating a resident mucosal memory T cell immune response against *Chlamydia trachomatis* in a subject in need thereof, the method comprising administering to the subject through a mucosal route an effective amount of a composition comprising a negatively charged inactivated *Chlamydia trachomatis*, and one or more adjuvant-loaded polymeric nanoparticles having a positive charge, wherein the one or more adjuvant-loaded polymeric nanoparticles are each attached to the inactivated *Chlamydia trachomatis* through electrostatic attraction, and the one or more adjuvant-loaded nanoparticles comprise poly(lactic-co-glycolic acid)-block-poly(L-histidine)-block-poly(ethylene glycol) (PLGA-PLH-PEG) triblock copolymers, thereby stimulating a resident mucosal memory T cell immune response against *Chlamydia trachomatis* in the subject.

2. The method of claim 1, wherein the one or more adjuvant-loaded polymeric nanoparticles comprise an adjuvant that targets an endosomal membrane.

3. The method of claim 1, wherein the one or more adjuvant-loaded polymeric nanoparticles comprise a Toll-like receptor agonist.

4. The method of claim 1, wherein the one or more adjuvant-loaded polymeric nanoparticles comprise biodegradable polymers.

5. The method of claim 1, wherein the one or more adjuvant-loaded polymeric nanoparticles comprise R848-polylactic acid.

6. The method of claim 1, wherein the composition is administered to the subject by an intranasal route.

7. The method of claim 1, wherein the composition is administered to the subject by an intrauterine route.

* * * * *